United States Patent
Anderson et al.

(10) Patent No.: US 12,168,682 B2
(45) Date of Patent: Dec. 17, 2024

(54) DIAGNOSTIC, PROGNOSTIC, THERAPEUTIC AND SCREENING PROTOCOLS

(71) Applicant: The MacFarlane Burnet Institute for Medical Research and Public Health Ltd, Melbourne (AU)

(72) Inventors: David Andrew Anderson, Melbourne (AU); Mary Louise Garcia, Melbourne (AU); Nadine Carmel Barnes, Melbourne (AU); Khayriyyah Mohd Hanafiah, Melbourne (AU); Alan Lee Landay, Melbourne (AU)

(73) Assignee: The MacFarlane Burnet Institute for Medical Research and Public Health Ltd, Melbourne (AU)

( * ) Notice: Subject to any disclaimer, the term of this patent is extended or adjusted under 35 U.S.C. 154(b) by 1359 days.

(21) Appl. No.: 16/271,588

(22) Filed: Feb. 8, 2019

(65) Prior Publication Data

US 2019/0359679 A1  Nov. 28, 2019

Related U.S. Application Data

(63) Continuation of application No. 14/441,606, filed as application No. PCT/AU2013/001291 on Nov. 8, 2013, now abandoned.

(30) Foreign Application Priority Data

Nov. 8, 2012 (AU) .............................. 2012904887

(51) Int. Cl.
C07K 14/705 (2006.01)
G01N 33/569 (2006.01)
G01N 33/68 (2006.01)

(52) U.S. Cl.
CPC . *C07K 14/70503* (2013.01); *G01N 33/56983* (2013.01); *G01N 33/6854* (2013.01); *C07K 2319/00* (2013.01); *G01N 2333/08* (2013.01); *G01N 2333/10* (2013.01); *G01N 2333/16* (2013.01); *G01N 2333/70535* (2013.01); *G01N 2469/20* (2013.01); *G01N 2800/06* (2013.01)

(58) Field of Classification Search
None
See application file for complete search history.

(56) References Cited

U.S. PATENT DOCUMENTS

| | | |
|---|---|---|
| 6,596,476 B1 | 7/2003 | Lesniewski et al. |
| 2002/0055186 A1 | 5/2002 | Barry et al. |
| 2003/0003599 A1 | 1/2003 | Wagner et al. |
| 2003/0161809 A1 | 8/2003 | Houston et al. |

FOREIGN PATENT DOCUMENTS

| | | |
|---|---|---|
| WO | 91/16061 | 10/1991 |
| WO | 96/18734 | 6/1996 |
| WO | 1999039210 A1 | 8/1999 |
| WO | 2001079849 A2 | 10/2001 |
| WO | 2002039120 A1 | 5/2002 |
| WO | 2002059601 A1 | 8/2002 |
| WO | 2002090579 A1 | 11/2002 |
| WO | 2003062444 A2 | 7/2003 |
| WO | 2003077851 A2 | 9/2003 |
| WO | 2004044236 A1 | 5/2004 |

OTHER PUBLICATIONS

Mantis, N., Rol, N. & Corthésy, B. Secretory IgA's complex roles in immunity and mucosal homeostasis in the gut. Mucosal Immunol 4, 603-611 (2011). https://doi.org/10.1038/mi.2011.41 (Year: 2011).*
Bonner, A., Almogren, A., Furtado, P et al. Location of secretory component on the Fc edge of dimeric IgA1 reveals insight into the role of secretory IgA1 in mucosal immunity. Mucosal Immunol 2, 74-84 (2008). https://doi.org/10.1038/mi.2008.68 (Year: 2008).*
Rindisbacher et al. Production of Human Secretory Component with Dimeric IgA Binding Capacity Using Viral Expression Systems. The Journal of Biological Chemistry, vol. 270, No. 23, Issue of Jun. 9, pp. 14220-14228, (1995). (Year: 1995).*
Mestecky J, Russell MW, Elson CO Intestinal IgA: novel views on its function in the defense of the largest mucosal surface Gut 1999;44:2-5, published Jan. 1, 1999. (Year: 1999).*
Akahonai et al., "IgA Anti-HAV Antibody in Serum From Patients With Hepatitis A", Protides of the Biological Fluids, 32:331-334, 1985.
Anderson et al., "Diagnostic applications of dimeric IgA", Clinical and Experimental Pharmacology and Physiology, Oct. 2013, vol. 40, Supplement 1, p. 35, Abstract P07-12 (4th Meeting of the Australia Chinese Association for Biomedical Sciences Inc., ACABS 2013).
Asano and Komiyama, "Polymeric immunoglobulin receptor", Journal of Oral Science, 53(2):147-156, 2011.
Bakos et al., "Expression and purification of biologically active domain I of the human polymeric immunoglobulin receptor", Molecular Immunology, 31(2):165-168, 1994.

(Continued)

*Primary Examiner* — Nancy J Leith
*Assistant Examiner* — Jessica D Parisi
(74) *Attorney, Agent, or Firm* — Greenberg Traurig LLP; Melissa Hunter-Ensor; Nicholas R. Ballor

(57) ABSTRACT

The specification describes an antibody capture process comprising (i) obtaining a biological sample comprising antibodies, (ii) contacting the biological sample with recombinant pIgR or a dIgA-binding variant, wherein the pIgR or variant binds dIgA and forms a pIgR-dIgA complex. The process may further comprise (iii) directly or indirectly assessing the level of the pIgR-dIgA complex or the level of a complex between pIgR-dIgA and an antigen of interest. There is also an antibody capture process for determining gut wall integrity in a test subject, wherein the level or ratio of SIgA to dIgA is compared to a corresponding level or ratio from a control subject. The specification provides kits embodying the process and recombinant pIgR when used for, or for use, in capturing or detecting dIgA and/or IgM.

9 Claims, 42 Drawing Sheets

Figure 1:
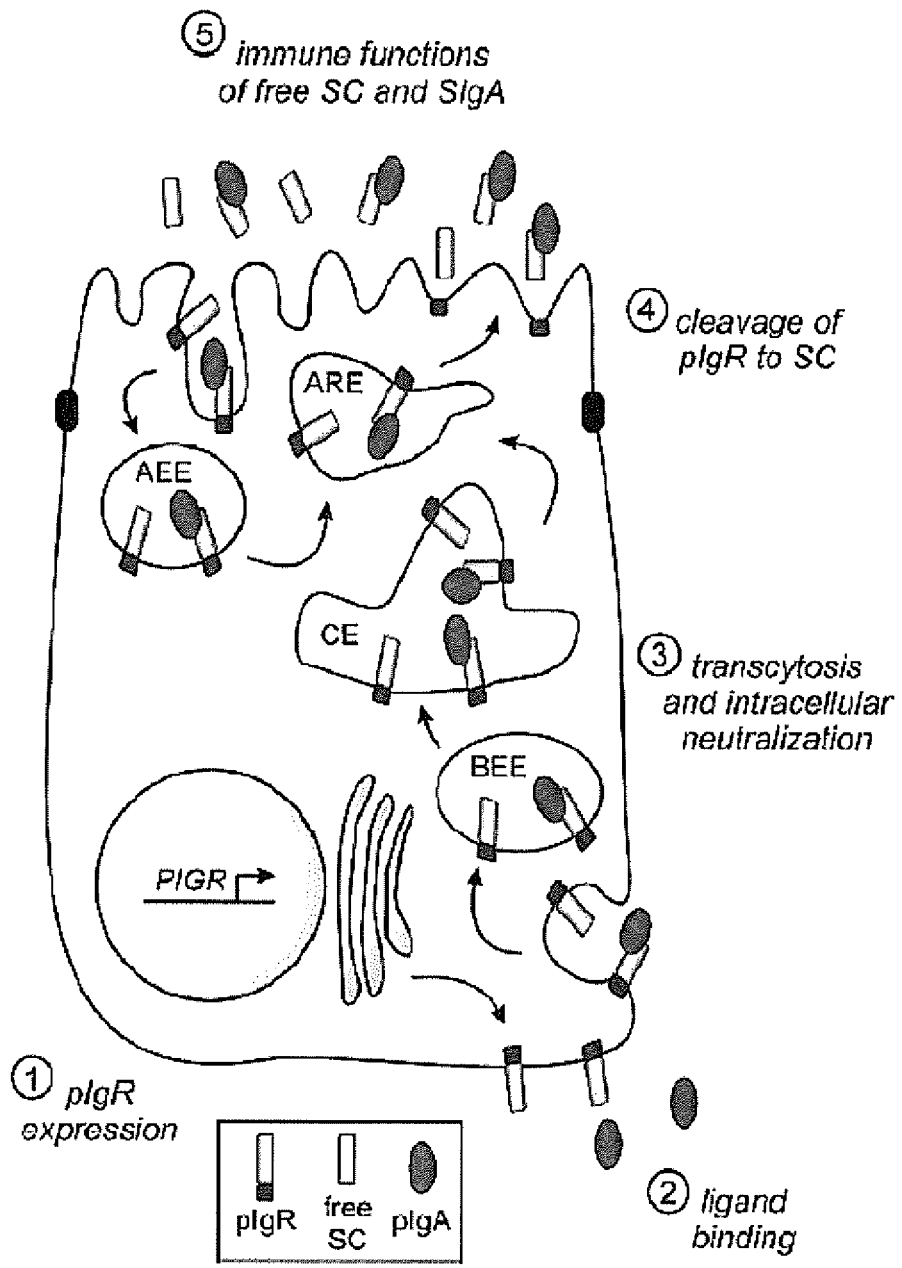

Specification includes a Sequence Listing.

(56) References Cited

OTHER PUBLICATIONS

Bartholomeusz et al., "Assays for total and antigen-specific polymeric IgA in serum based on binding to secretory component", Journal of Immunologic Methods, 117:247-255, 1989.
Brandtzaeg, "Secretory IgA: designed for anti-microbial defense", Frontiers in Immunology, vol. 4, Article 222, 2013.
Brown et al., "Tolerance of single, but not multiple, amino acid replacements in antibody VH CDR 2: a means of minimizing B cell wastage from somatic hypermutation?", Journal of Immunology, 156:3285-3291, 1996.
Colman, "Effects of amino acid sequence changes on antibody-antigen interactions", Research in Immunology, 145 (1):33-36, 1994.
Crottet and Corthésy, "Secretory Component Delays the Conversion of Secretory IgA into Antigen-Binding Competent F(ab')2: A Possible Implication for Mucosal Defense", The Journal of Immunology, 161:5445-5453, 1998.
Crottet et al., "Expression, purification and biochemical characterization of recombinant murine secretory component: a novel tool in mucosal immunology", Biochem. J., 341:299-306, 1999.
Dotzauer et al., "IgA-coated particles of Hepatitis A virus are translocalized antivectorially from the apical to the basolateral site of polarized epithelial cells via the polymeric Immunoglobulin receptor", Journal of General Virology, 86:2747-2751, 2005.
Harlow et al., Antibodies: A Laboratory Manual, Cold Spring Harbor Laboratory Press, Cold Spring Harbor, NY. pp. 23-26, 553 and 578-581, 1988.
Hexham et al., "A Human Immunoglobin (Ig)A Co3 Domain Motif Directs Polymeric Ig Receptor-mediated Secretion", Journal of Experimental Medicine, 189(4):747-751, 1999.
Lederman et al., "A single amino acid substitution in a common African allele of the CD4 molecule ablates binding of the monoclonal antibody, OKT4", Molecular Immunology, 28(11):1171-1181, 1991.
Norderhaug et al., "Domain deletions in the human polymeric Ig receptor disclose differences between its dimeric IgA and pentameric IgM interaction", European Journal of Immunology, 29:3401-3409, 1999.
Røe et al., "Fine Specificity of Ligand-Binding Domain 1 in the Polymeric Ig Receptor: Importance of CDR2-Containing Region for IgM Interaction", The Journal of Immunology, 162:6046-6052, 1999.
Supplementary European Search Report dated May 4, 2016 (7 pages).
Written Opinion and International Search Report for PCT/AU2013/001291 dated Feb. 12, 2014 (13 pages).
Brenchley et al., "Microbial translocation is a cause of systemic immune activation in chronic HIV infection," Nature Medicine, Dec. 2006, vol. 12, No. 12, pp. 1365-1371.
Cahill, Dolores J., "Protein arrays: a high-throughput solution for proteomics research?" Proteomics: A Trends Guide, Trends in Biotechnology, Jul. 2000, vol. 18, pp. 47-51.
Cohen et al., "An artificial cell-cycle inhibitor isolated from a combinatorial library," Proceedings of the National Academy of Sciences of the United States of America, Nov. 1998, vol. 95, pp. 14272-14277.
Crago et al., "Distribution of IgA1-, IgA2-, and J Chain-Containing Cells in Human Tissues," The Journal of Immunology, Jan. 1984, vol. 132, No. 1, pp. 16-18.
Craik et al., "Redesigning Trypsin: Alteration of Substrate Specificity," Science, Apr. 19, 1985, vol. 228, No. 4697, pp. 291-297.
Cronin et al., "Role of Arginine-292 in the Substrate Specificity of Aspartate Aminotransferase as Examined by Site-Directed Mutagenesis," Biochemistry, 1988, vol. 27, No. 12, pp. 4572-4579.
French et al., "Serum Immune Activation Markers Are Persistently Increased in Patients with HIV Infection after 6 Years of Antiretroviral Therapy despite Suppression of Viral Replication and Reconstitution of CD4+ T Cells," The Journal of Infectious Diseases, Oct. 15, 2009, vol. 200, pp. 1212-1215.
Ge, Hui, "UPA, a universal protein array system for quantitative detection of protein-protein, protein-DNA, protein-RNA and protein-ligand interactions," Nucleic Acids Research, 2000, vol. 28, No. 2, e3, pp. i-vii.
Gerlt, John A., "Relationships between Enzymatic Catalysis and Active Site Structure Revealed by Applications of Site-Directed Mutagenesis," Chemical Reviews, 1987, vol. 87, No. 5, pp. 1079-1105.
He et al., "Intestinal Bacteria Trigger T Cell-Independent Immunoglobulin A2 Class Switching by Inducing Epithelial-Cell Secretion of the Cytokine APRIL," Immunity, Jun. 2007, vol. 26, pp. 812-826.
Iacobelli et al., "Measurement of a breast cancer associated antigen detected by monoclonal antibody SP-2 in sera of cancer patients," Breast Cancer Research and Treatment, 1988, vol. 11, pp. 19-30.
Kaetzel et al., "Epithelial Transport of IgA by the Polymeric Immunoglobulin Receptor," Mucosal Immune Defense: Immunoglobulin A, 2007, pp. 43-89.
Knowles, Jeremy R., "Tinkering with Enzymes: What Are We Learning?," Science, Jun. 5, 1987, vol. 236, No. 4806, pp. 1252-1258.
Leatherbarrow et al., "Protein engineering," Protein Engineering, Design and Selection, 1986, vol. 1, No. 1, pp. 7-16.
Lopez et al., "Protein micro- and macroarrays: digitizing the proteome," Journal of Chromatography B, 2003, vol. 787, pp. 19-27.
Nilssen et al., "Intestinal B cell hyperactivity in AIDS is controlled by highly active antiretroviral therapy," Gut, 2004, vol. 53, pp. 487-493.
Phillips-Quagliata et al., "The IgA/IgM Receptor Expressed on a Murine B Cell Lymphoma Is Poly-Ig Receptor," The Journal of Immunology, 2000, vol. 165, pp. 2544-2555.
Potyrailo et al., "Adapting Selected Nucleic Acid Ligands (Aptamers) to Biosensors," Analytical Chemistry, Aug. 15, 1998, vol. 70, No. 16, pp. 3419-3425.
Roberts et al., "RNA-peptide fusions for the in vitro selection of peptides and proteins," Proceedings of the National Academy of Sciences of the United States of America, Nov. 1997, vol. 94, pp. 12297-12302.
Shaw, William V., "Protein engineering: The design, synthesis and characterization of factitious proteins," Biochemical Journal, 1987, vol. 246, pp. 1-17.
Wilks et al., "A Specific, Highly Active Malate Dehydrogenase by Redesign of a Lactate Dehydrogenase Framework," Science, Dec. 16, 1988, vol. 242, pp. 1541-1544.
Woof et al., "Structure and function relationships in IgA," Mucosal Immunology, Nov. 2011, vol. 4, No. 6, pp. 590-597.
Zhang et al., "The level of serum secretory IgA of patients with IgA nephropathy is elevated and associated with pathological phenotypes," Nephrology Dialysis Transplantation, 2008, vol. 23, pp. 207-212.

\* cited by examiner

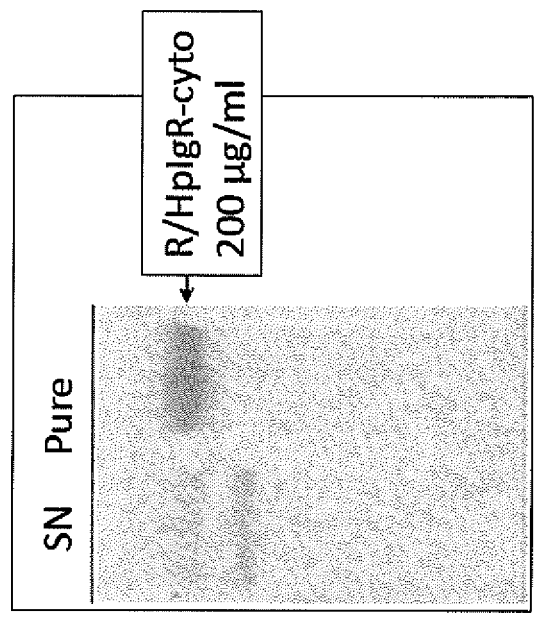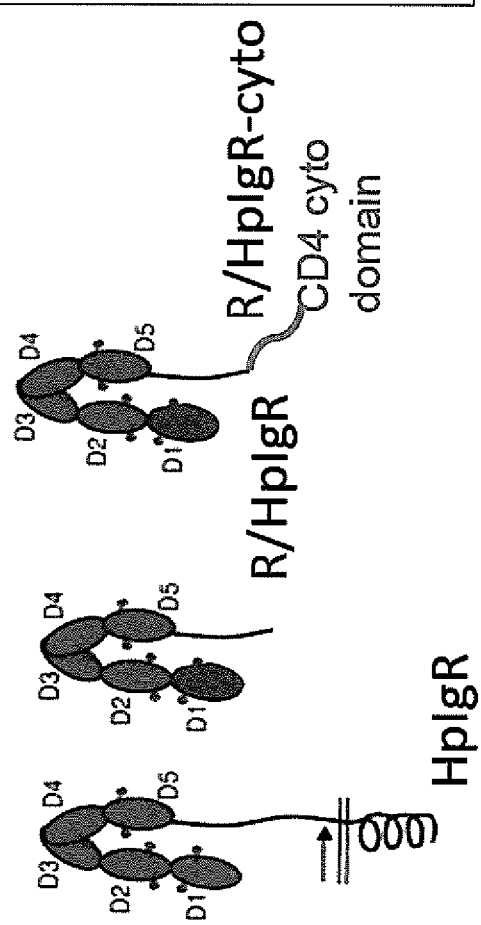
FIGURE 3

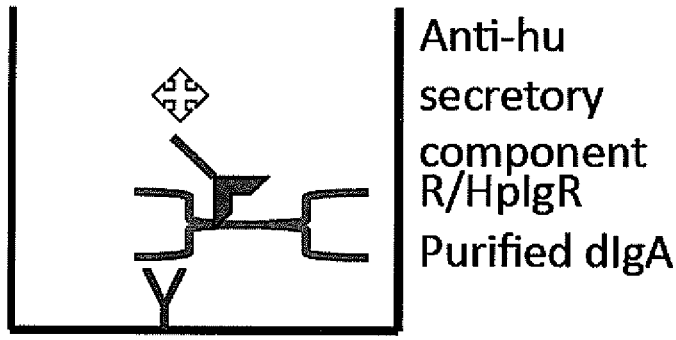
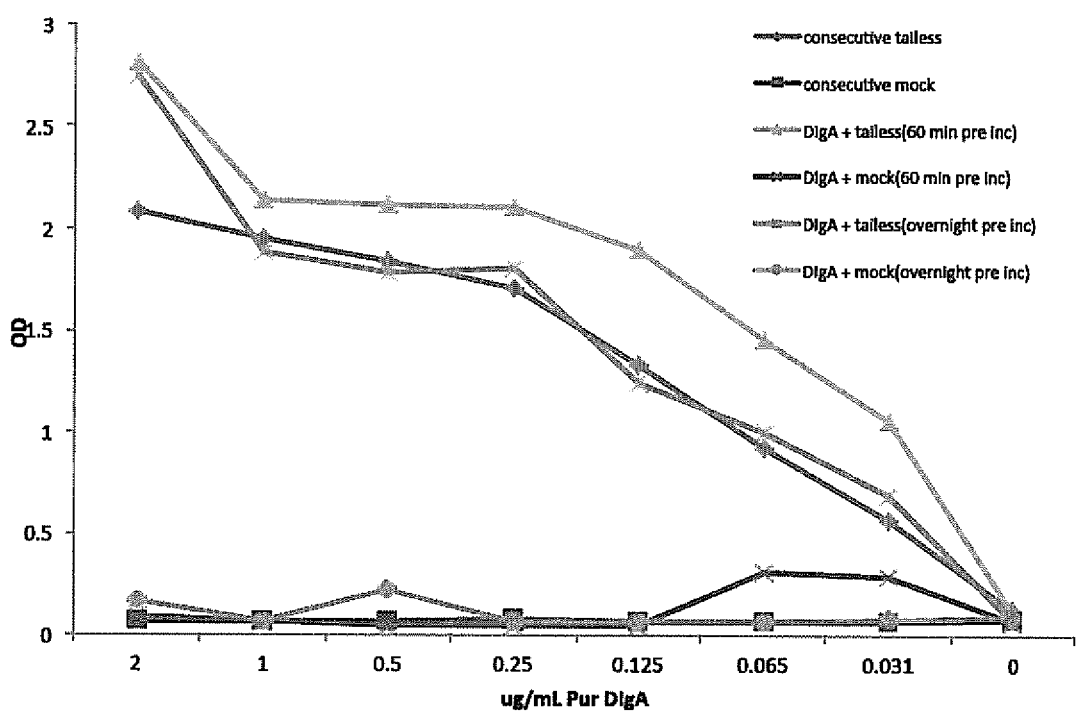
FIGURE 9

FIGURE 15 (CONTINUED)

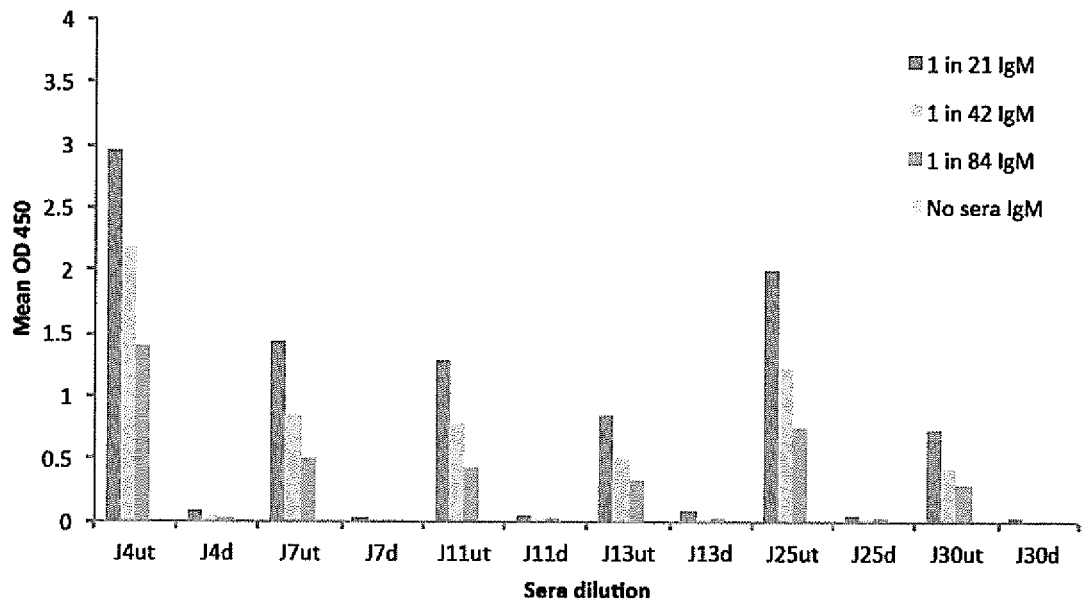
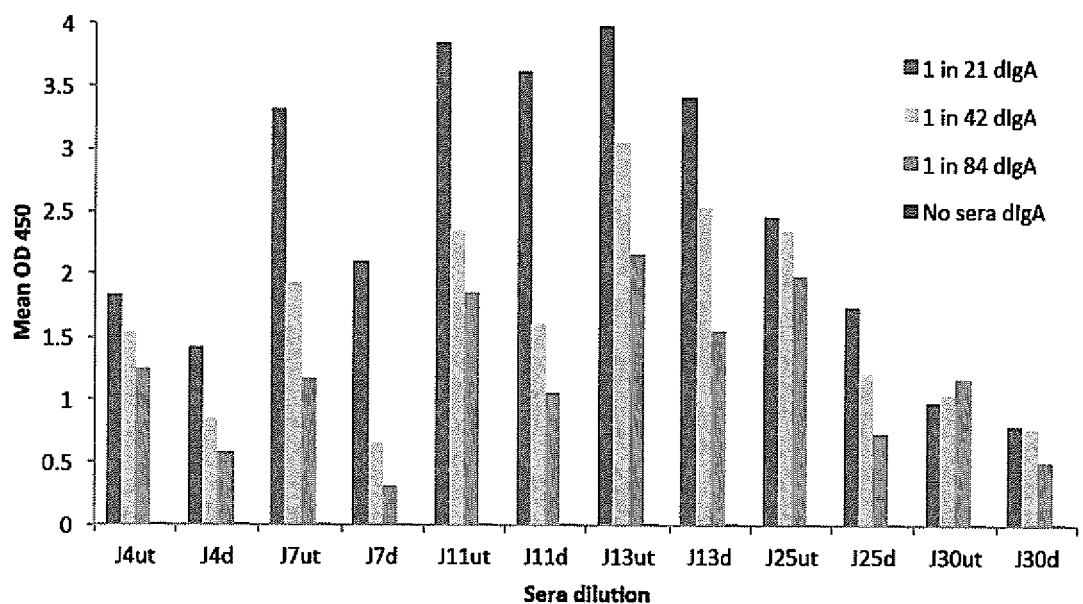
FIGURE 18

A

B

```
atggctctcttcttgctcacctgcctgctggctgtcttttcagcggccacggcacaaagc
 M  A  L  F  L  L  T  C  L  L  A  V  F  S  A  A  T  A  Q  S
tccttattgggtcccagctccatatttggtccgggggaggtgaatgttttggaaggcgac
 S  L  L  G  P  S  S  I  F  G  P  G  E  V  N  V  L  E  G  D
tcggtgtccatcacatgctactacccaacaacctccgtcacccggcacagccggaagttc
 S  V  S  I  T  C  Y  Y  P  T  T  S  V  T  R  H  S  R  K  F
tggtgccgggaagaggagagcggccgctgcgtgacgcttgcctcgaccggctacacgtcc
 W  C  R  E  E  E  S  G  R  C  V  T  L  A  S  T  G  Y  T  S
caggaatactccgggagaggcaagctcaccgacttccctgataaaggggagtttgtggtg
 Q  E  Y  S  G  R  G  K  L  T  D  F  P  D  K  G  E  F  V  V
actgttgaccaactcacccagaacgactcagggagctacaagtgtggcgtgggagtcaac
 T  V  D  Q  L  T  Q  N  D  S  G  S  Y  K  C  G  V  G  V  N
ggccgtggcctggacttcggtgtcaacgtgctggtcagccagaagccagagctcctaaat
 G  R  G  L  D  F  G  V  N  V  L  V  S  Q  K  P  E  L  L  N
gacactaaagtctacacagtggacctgggcagaacggtgaccatcaactgcccttttcaag
 D  T  K  V  Y  T  V  D  L  G  R  T  V  T  I  N  C  P  F  K
actgagaatgctcaaaagaggaagtccttgtacaagcagataggcctgtaccctgtgctg
 T  E  N  A  Q  K  R  K  S  L  Y  K  Q  I  G  L  Y  P  V  L
gtcatcgactccagtggttatgtaaatcccaactatacaggaagaatacgccttgatatt
 V  I  D  S  S  G  Y  V  N  P  N  Y  T  G  R  I  R  L  D  I
cagggtactggccagttactgttcagcgttgtcatcaaccaactcaggctcagcgatgct
 Q  G  T  G  Q  L  L  F  S  V  V  I  N  Q  L  R  L  S  D  A
ggcagtatctctgccaggctggggatgattccaatagtaataagaagaatgctgacctc
 G  Q  Y  L  C  Q  A  G  D  D  S  N  S  N  K  K  N  A  D  L
caagtgctaaagcccgagcccgagctggtttatgaagacctgaggggctcagtgaccttc
 Q  V  L  K  P  E  P  E  L  V  Y  E  D  L  R  G  S  V  T  F
cactgtgccctgggccctgaggtggcaaacgtggccaaattctgtgccgacagagcagt
 H  C  A  L  G  P  E  V  A  N  V  A  K  F  L  C  R  Q  S  S
ggggaaaactgtgacgtggtcgtcaacaccctggggaagagggccccagcctttgagggc
 G  E  N  C  D  V  V  V  N  T  L  G  K  R  A  P  A  F  E  G
aggatcctgctcaaccccaggacaaggatggctcattcagtgtggtgatcacaggcctg
 R  I  L  L  N  P  Q  D  K  D  G  S  F  S  V  V  I  T  G  L
aggaaggaggatgcagggcgctacctgtgtggagcccattcggatggtcagctgcaggaa
 R  K  E  D  A  G  R  Y  L  C  G  A  H  S  D  G  Q  L  Q  E
ggctcgcctatccaggcctggcaactcttcgtcaatgaggagtccacgattccccgcagc
 G  S  P  I  Q  A  W  Q  L  F  V  N  E  E  S  T  I  P  R  S
cccactgtggtgaaggggggtggcaggaggctctgtggccgtgctctgcccctacaaccgt
 P  T  V  V  K  G  V  A  G  G  S  V  A  V  L  C  P  Y  N  R
aaggaaagcaaaagcatcaagtactggtgtctctgggaaggggcccagaatggccgctgc
 K  E  S  K  S  I  K  Y  W  C  L  W  E  G  A  Q  N  G  R  C
cccctgctggtggacagcgaggggtgggttaaggcccagtacgagggccgcctctccctg
 P  L  L  V  D  S  E  G  W  V  K  A  Q  Y  E  G  R  L  S  L
```

FIGURE 33

```
ctggaggagccaggcaacggcaccttcactgtcatcctcaaccagctcaccagccgggac
 L   E   E   P   G   N   G   T   F   T   V   I   L   N   Q   L   T   S   R   D
gccggcttctactggtgtctgaccaacggcgatactctctggaggaccaccgtggagatc
 A   G   F   Y   W   C   L   T   N   G   D   T   L   W   R   T   T   V   E   I
aagattatcgaaggagaaccaaacctcaaggtaccagggaatgtcacggctgtgctggga
 K   I   I   E   G   E   P   N   L   K   V   P   G   N   V   T   A   V   L   G
gagactctcaaggtcccctgtcactttccatgcaaattctcctcgtacgagaaatactgg
 E   T   L   K   V   P   C   H   F   P   C   K   F   S   S   Y   E   K   Y   W
tgcaagtggaataacacgggctgccaggccctgcccagccaagacgaaggccccagcaag
 C   K   W   N   N   T   G   C   Q   A   L   P   S   Q   D   E   G   P   S   K
gccttcgtgaactgtgacgagaacagccggcttgtctccctgaccctgaacctggtgacc
 A   F   V   N   C   D   E   N   S   R   L   V   S   L   T   L   N   L   V   T
agggctgatgagggctggtactggtgtggagtgaagcagggccacttctatggagagact
 R   A   D   E   G   W   Y   W   C   G   V   K   Q   G   H   F   Y   G   E   T
gcagccgtctatgtggcagttgaagagaggaaggcagcggggtcccgcgatgtcagccta
 A   A   V   Y   V   A   V   E   E   R   K   A   A   G   S   R   D   V   S   L
gcgaaggcagacgctgctcctgatgagaaggtgctagactctggttttcgggagattgag
 A   K   A   D   A   A   P   D   E   K   V   L   D   S   G   F   R   E   I   E
aacaaagccattcaggatcccaggcttttgcagaggaaaaggcggtggcagatacaaga
 N   K   A   I   Q   D   P   R   L   F   A   E   E   K   A   V   A   D   T   R
gatcaagccgatgggagcagagcatctgtggattccggcagctctgaggaacaaggtgga
 D   Q   A   D   G   S   R   A   S   V   D   S   G   S   S   E   E   Q   G   G
agctccagaaggtgccggcaccgaaggcgccaagcagagcggatgtctcagatcaagaga
 S   S   R   R   C   R   H   R   R   R   Q   A   E   R   M   S   Q   I   K   R
ctcctcagtgagaagaagacctgccagtgcctcaccggtttcagaagacatgtagcccc
 L   L   S   E   K   K   T   C   Q   C   P   H   R   F   Q   K   T   C   S   P
atttga
 I   -
```

FIGURE 33 (CONTINUED)

```
atggctctcttcttgctcacctgcctgctggctgtcttttcagcggccacggcacaaagc
 M  A  L  F  L  L  T  C  L  L  A  V  F  S  A  A  T  A  Q  S
tccttattgggtcccagctccatatttggtccggggaggtgaatgttttggaaggcgac
 S  L  L  G  P  S  S  I  F  G  P  G  E  V  N  V  L  E  G  D
tcggtgtccatcacatgctactacccaacaacctccgtcacccggcacagccggaagttc
 S  V  S  I  T  C  Y  Y  P  T  T  S  V  T  R  H  S  R  K  F
tggtgccgggaagaggagagcggccgctgcgtgacgcttgcctcgaccggctacacgtcc
 W  C  R  E  E  S  G  R  C  V  T  L  A  S  T  G  Y  T  S
caggaatactccgggagaggcaagctcaccgacttccctgataaaggggagtttgtggtg
 Q  E  Y  S  G  R  G  K  L  T  D  F  P  D  K  G  E  F  V  V
actgttgaccaactcacccagaacgactcagggagctacaagtgtggcgtgggagtcaac
 T  V  D  Q  L  T  Q  N  D  S  G  S  Y  K  C  G  V  G  V  N
ggccgtggcctggacttcggtgtcaacgtgctggtcagccagaagccagagctcctaaat
 G  R  G  L  D  F  G  V  N  V  L  V  S  Q  K  P  E  L  L  N
gacactaaagtctacacagtggacctgggcagaacggtgaccatcaactgccctttcaag
 D  T  K  V  Y  T  V  D  L  G  R  T  V  T  I  N  C  P  F  K
actgagaatgctcaaaagaggaagtccttgtacaagcagataggcctgtaccctgtgctg
 T  E  N  A  Q  K  R  K  S  L  Y  K  Q  I  G  L  Y  P  V  L
gtcatcgactccagtggttatgtaaatcccaactatacaggaagaatacgccttgatatt
 V  I  D  S  S  G  Y  V  N  P  N  Y  T  G  R  I  R  L  D  I
cagggtactggccagttactgttcagcgttgtcatcaaccaactcaggctcagcgatgct
 Q  G  T  G  Q  L  L  F  S  V  V  I  N  Q  L  R  L  S  D  A
gggcagtatctctgccaggctggggatgattccaatagtaataagaagaatgctgacctc
 G  Q  Y  L  C  Q  A  G  D  D  S  N  S  N  K  K  N  A  D  L
caagtgctaaagcccgagcccgagctggtttatgaagacctgaggggctcagtgaccttc
 Q  V  L  K  P  E  P  E  L  V  Y  E  D  L  R  G  S  V  T  F
cactgtgccctgggccctgaggtggcaaacgtggccaaattctgtgccgacagagcagt
 H  C  A  L  G  P  E  V  A  N  V  A  K  F  L  C  R  Q  S  S
ggggaaaactgtgacgtggtcgtcaacaccctggggaagagggccccagcctttgagggc
 G  E  N  C  D  V  V  V  N  T  L  G  K  R  A  P  A  F  E  G
aggatcctgctcaaccccaggacaaggatggctcattcagtgtggtgatcacaggcctg
 R  I  L  L  N  P  Q  D  K  D  G  S  F  S  V  V  I  T  G  L
aggaaggaggatgcagggcgctacctgtgtggagcccattcggatggtcagctgcaggaa
 R  K  E  D  A  G  R  Y  L  C  G  A  H  S  D  G  Q  L  Q  E
ggctcgcctatccaggcctggcaactcttcgtcaatgaggagtccacgattccccgcagc
 G  S  P  I  Q  A  W  Q  L  F  V  N  E  E  S  T  I  P  R  S
cccactgtggtgaaggggggtggcaggaggctctgtggccgtgctctgcccctacaaccgt
 P  T  V  V  K  G  V  A  G  G  S  V  A  V  L  C  P  Y  N  R
aaggaaagcaaaagcatcaagtactggtgtctctgggaaggggcccagaatggccgctgc
 K  E  S  K  S  I  K  Y  W  C  L  W  E  G  A  Q  N  G  R  C
cccctgctggtggacagcgaggggtgggttaaggcccagtacgagggccgcctctccctg
 P  L  L  V  D  S  E  G  W  V  K  A  Q  Y  E  G  R  L  S  L
```

FIGURE 34

```
ctggaggagccaggcaacggcaccttcactgtcatcctcaaccagctcaccagccgggac
 L   E   E   P   G   N   G   T   F   T   V   I   L   N   Q   L   T   S   R   D
gccggcttctactggtgtctgaccaacggcgatactctctggaggaccaccgtggagatc
 A   G   F   Y   W   C   L   T   N   G   D   T   L   W   R   T   T   V   E   I
aagattatcgaaggagaaccaaacctcaaggtaccagggaatgtcacggctgtgctggga
 K   I   I   E   G   E   P   N   L   K   V   P   G   N   V   T   A   V   L   G
gagactctcaaggtcccctgtcactttccatgcaaattctcctcgtacgagaaatactgg
 E   T   L   K   V   P   C   H   F   P   C   K   F   S   S   Y   E   K   Y   W
tgcaagtggaataacacgggctgccaggccctgcccagccaagacgaaggccccagcaag
 C   K   W   N   N   T   G   C   Q   A   L   P   S   Q   D   E   G   P   S   K
gccttcgtgaactgtgacgagaacagccggcttgtctccctgaccctgaacctggtgacc
 A   F   V   N   C   D   E   N   S   R   L   V   S   L   T   L   N   L   V   T
agggctgatgagggctggtactggtgtggagtgaagcagggccacttctatggagagact
 R   A   D   E   G   W   Y   W   C   G   V   K   Q   G   H   F   Y   G   E   T
gcagccgtctatgtggcagttgaagagaggaaggcagcggggtcccgcgatgtcagccta
 A   A   V   Y   V   A   V   E   E   R   K   A   A   G   S   R   D   V   S   L
gcgaaggcagacgctgctcctgatgagaaggtgctagactctggttttcgggagattgag
 A   K   A   D   A   A   P   D   E   K   V   L   D   S   G   F   R   E   I   E
aacaaagccattcaggatcccaggcttttgcagaggaaaaggcggtggcagatacaaga
 N   K   A   I   Q   D   P   R   L   F   A   E   E   K   A   V   A   D   T   R
gatcaagccgatgggagcagagcatctgtggattccggcagctctgaggaacaaggtgga
 D   Q   A   D   G   S   R   A   S   V   D   S   G   S   S   E   E   Q   G   G
agctccagaaggTGA
 S   S   R   R   -
```

Figure 35:
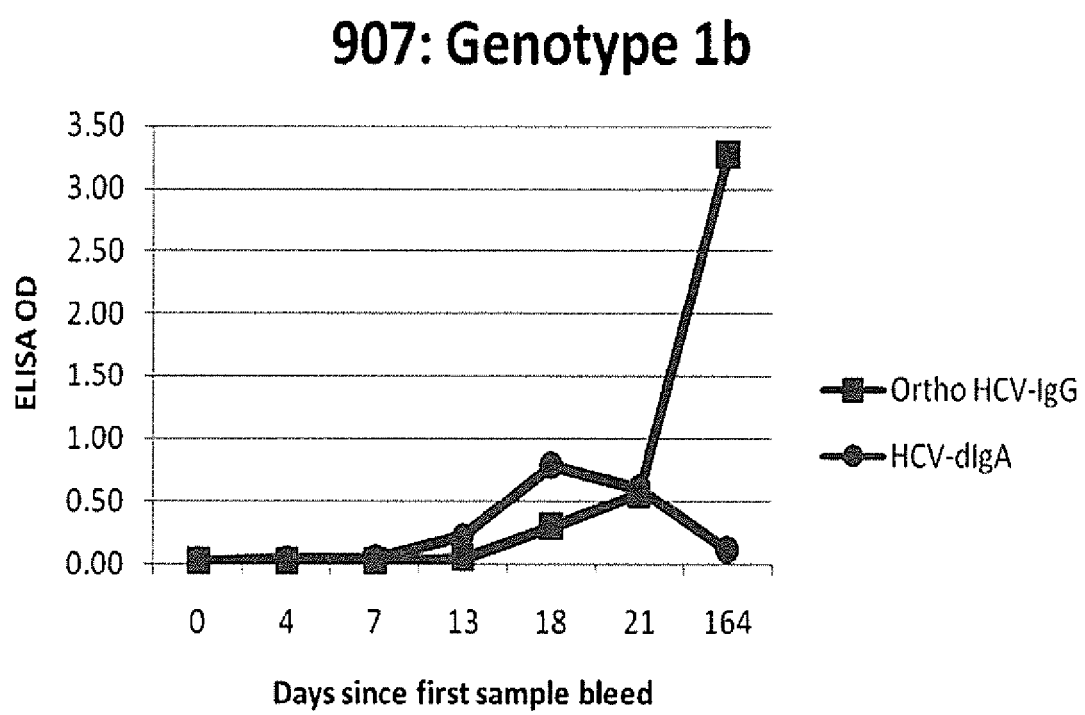

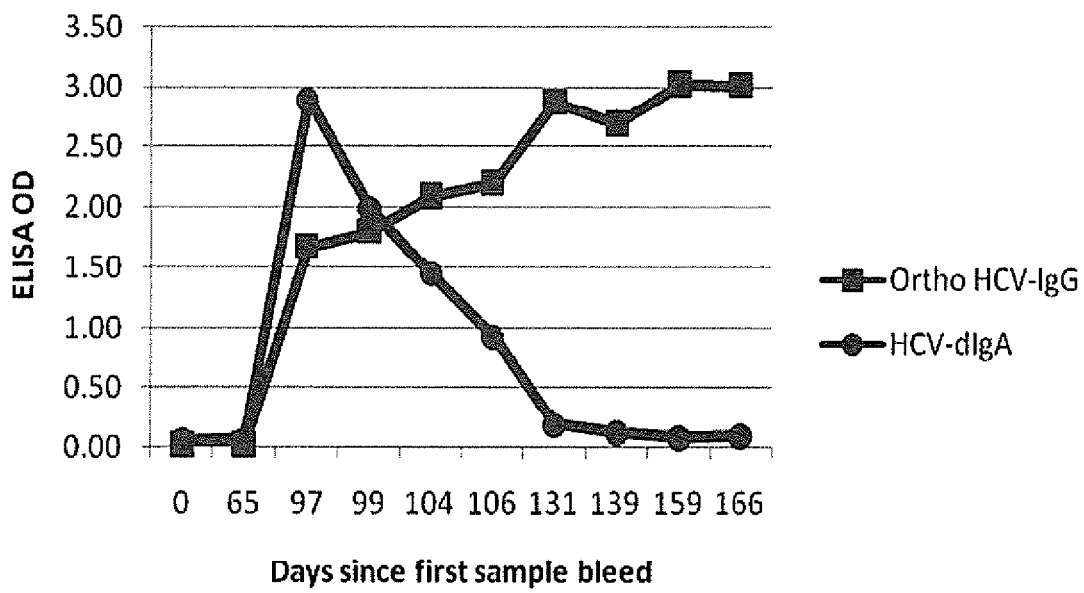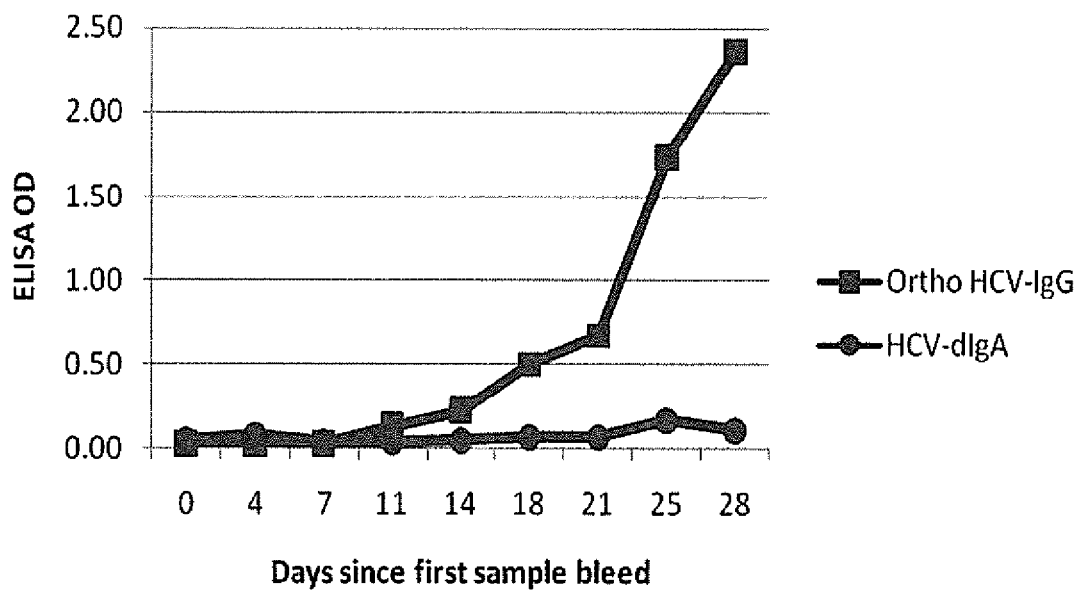
FIGURE 35

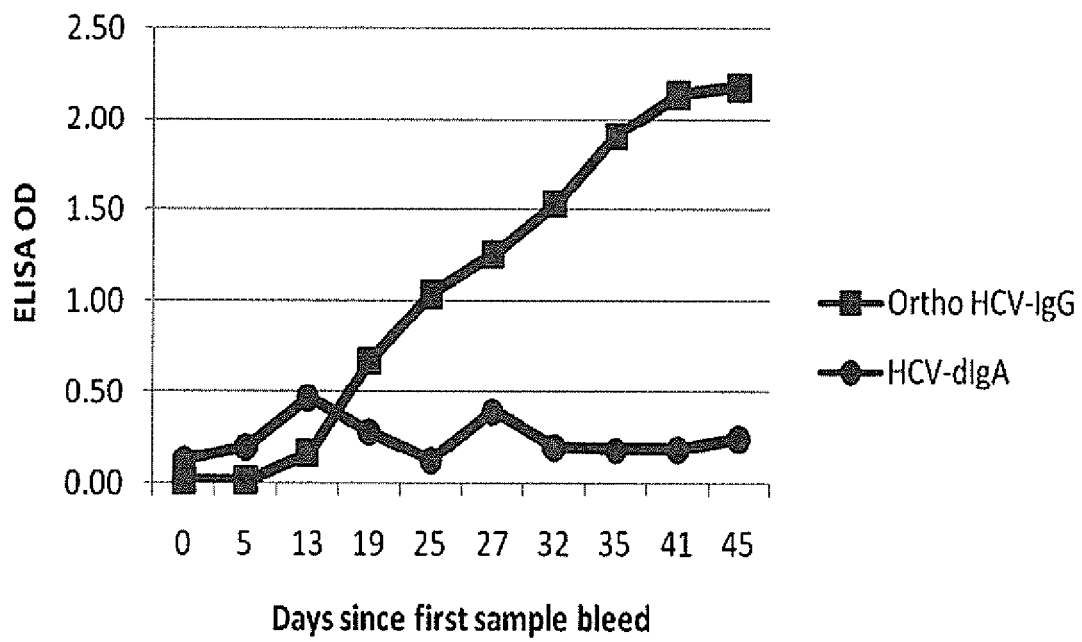
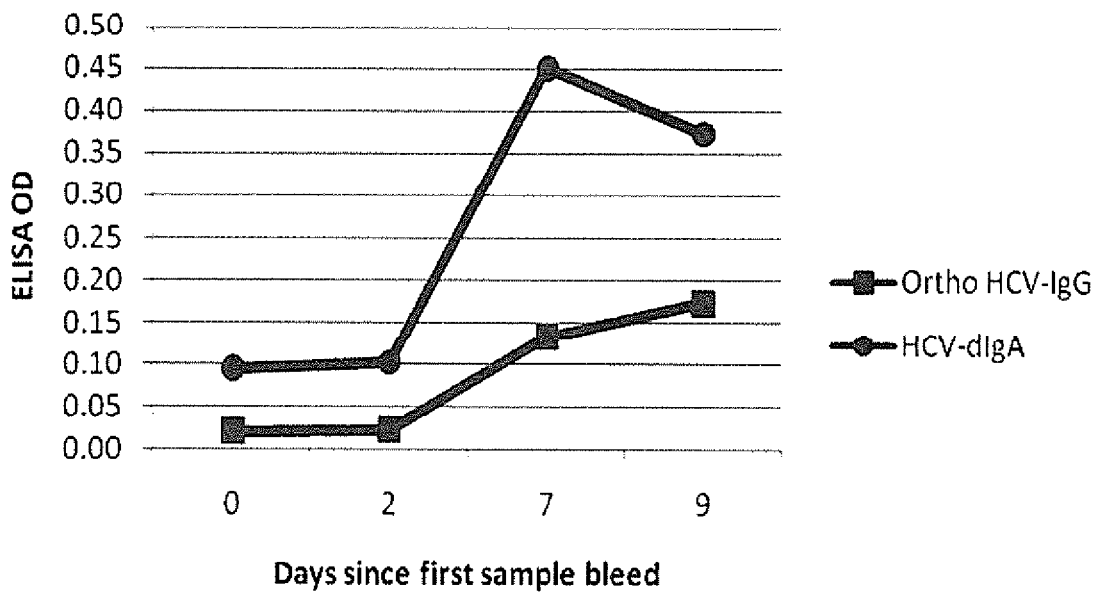
FIGURE 35 (CONTINUED)

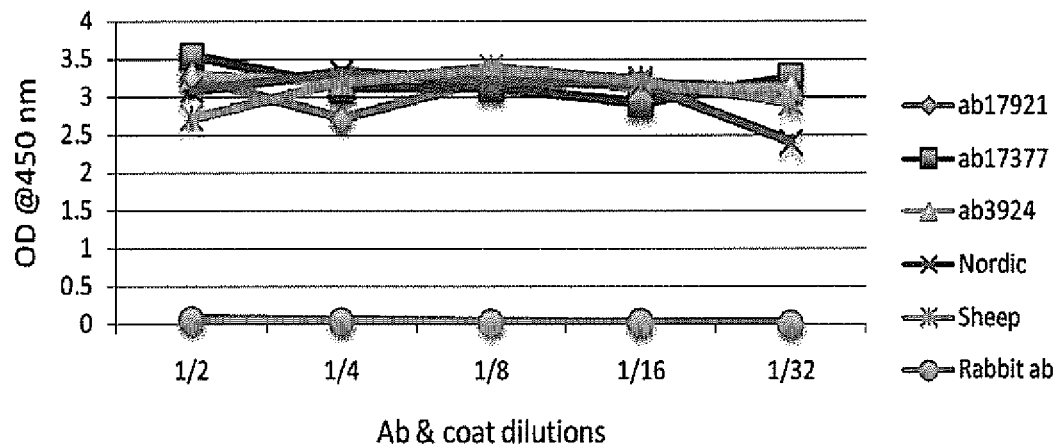
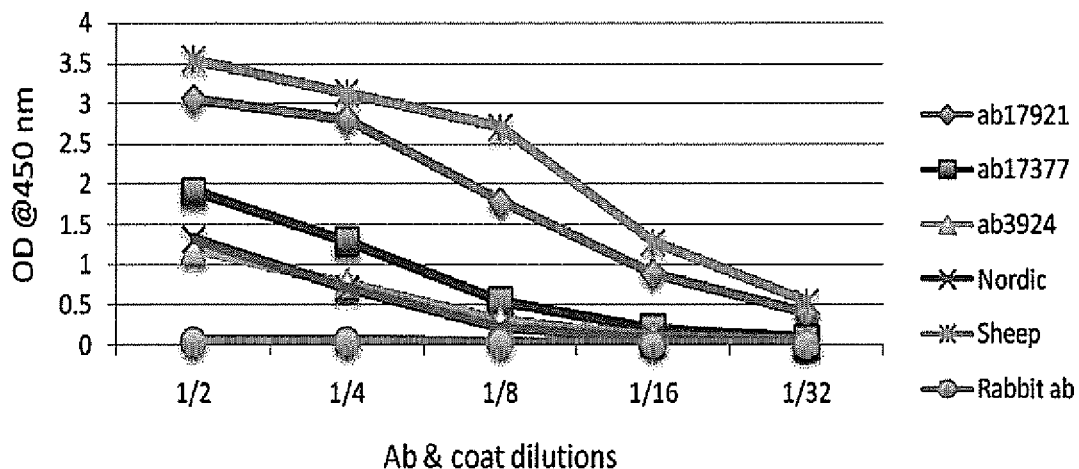
FIGURE 36

DIAGNOSTIC, PROGNOSTIC, THERAPEUTIC AND SCREENING PROTOCOLS

CROSS-REFERENCE TO RELATED APPLICATIONS

The present application is a continuation of U.S. Ser. No. 14/441,606, filed 8 May 2015, which is a 35 U.S.C. § 371 U.S. National phase application of International Patent Application No. PCT/AU2013/001291, filed 8 Nov. 2013, which claims priority from Australian Provisional Patent Application No. 2012904887 filed 8 Nov. 2012, the disclosures of all of the above applications are incorporated by reference herein in their entireties.

SEQUENCE LISTING

This application incorporates by reference in its entirety the Sequence Listing entitled "35209830 seq list_ST25.txt", which is 68,688 bytes in size, filed electronically herewith.

FIELD

The present specification relates generally to the fields of diagnostic, prognostic and therapeutic protocols with respect to infectious agents or other conditions associated with immune activation and particularly mucosal immune activation. More particularly, the specification relates to the use of antibodies as biomarkers for immune activation and/or for diagnosis, prognosis and treatment of conditions associated with immune activation. The present protocols are proposed for ready translation into both laboratory and point of care formats to reach target populations worldwide.

BACKGROUND

Bibliographic details references referred to in this specification are listed at the end of the specification.

The reference to any prior art is not and should not be taken as an acknowledgment or any form of suggestion that this prior art forms part of the common general knowledge in any country.

The detection of specific antibody (immunoglobulin (Ig)) classes is recognized as an important step in diagnostic and research methods for human and animal diseases. For example, detection of antigen-specific IgM-class antibodies is widely used as a diagnostic test for infection with viruses such as hepatitis A virus, hepatitis E virus, West Nile virus, dengue viruses, measles virus, rubella virus; and for infection with bacteria such as syphilis (*Treponema pallidum*), because IgM class antibodies are typically made in the body of an infected host during the acute phase of infection and are detectable for only a few months.

Conversely, IgG-class antibodies commonly persist for life and may indicate either current or past infection with a specific agent. For chronic infections such as the human immunodeficiency virus (HIV) where patients do not spontaneously clear the virus, detection of IgG-class antibodies is diagnostic for infection, whereas for others such as hepatitis C virus (HCV) where a proportion of patients do clear the virus either spontaneously or following treatment, the detection of antigen-specific IgG is not diagnostic of current or ongoing infection. IgG-class antibodies are also primarily responsible for antibody-mediated immunity within the plasma compartment of the body.

IgA-class antibodies have also been used to aid diagnosis of infections including hepatitis E virus, hepatitis A virus, and dengue viruses, as well as in the study of vaccines and immunity to infections. IgA is attractive for diagnostic purposes, because it is predominantly made during the acute phase of infection, and high levels of antigen-specific IgA can provide a marker of current infection, with or without the concurrent detection of IgM. In addition, because IgA is the predominant antibody class that is secreted at mucosal epithelial surfaces, its presence is considered as a marker of mucosal immunity. The role of different IgA structural forms as biomarkers for infection, such as specifically dIgA, is not understood. The role of SIgA in infection and antigens that engender SIgA responses have not been explored nor have diagnostic and prognostic protocols been developed that are designed to rapidly and conveniently assess these responses in patient sera.

In most animals, IgA is synthesized almost exclusively as dimeric or higher polymeric forms, here described collectively as dIgA, which are able to interact with the polymeric Ig receptor (pIgR). This interaction results in secretion of large amounts of secretory IgA (SIgA) into the lumen of epithelial tissues (see FIGS. 1 and 2). However, in humans and higher primates the dIgA is only a minor fraction of the total IgA, with monomeric IgA (mIgA) representing around 90% of the total IgA, and dimeric or higher polymeric forms of IgA representing around 10% of the total IgA.

Detection of IgA, IgM, IgG and other antibody classes or isotypes is usually performed using antibody reagents prepared in another species, for example rabbit antibodies specific for human IgM, or mouse monoclonal antibodies specific for human IgA, or monoclonal antibodies specific for individual antibody subclasses such as IgA1, IgA2 or IgG1, IgG2a, IgG2b, IgG3, IgG4. Antibody based capture assay are associated with levels of non-specific binding which is minimised through optimisation protocols.

There is a need for improved serological protocols for monitoring infections associated with mucosal surfaces and mucosal immune responses in a subject, and for agents that can be used to assess dimeric or polymeric antibody production and or for dimeric or polymeric antibody purification.

SUMMARY OF EMBODIMENTS

In one embodiment, therefore, the specification provides an antibody capture process comprising (i) obtaining a biological sample comprising antibodies, (ii) contacting the biological sample with recombinant pIgR or a dIgA-binding variant, wherein the pIgR or variant binds dIgA and forms a pIgR-dIgA complex. Once the complex has been formed, the complex may be quantified. In some embodiments, dIgA may be released from the pIgR and further processed. In one embodiment, the process is employed for the purification of dIgA antibodies as an alternative to existing processes which employ jacalin agarose. Detection of complexes uses routine methods and agents known in the art such as ELISA or other immunoassay based methods.

In one embodiment, the process further comprises (iii) directly or indirectly assessing the level of the pIgR-sIgA complex or the level of a complex between pIgR-dIgA and an antigen of interest.

In one embodiment, the pIgR or a dIgA-binding variant binds dIgA and substantially fails to bind IgM or wherein the pIgR or variant binds dIgA and IgM. Processes for detecting antigen specific IgM and dIgA may be used in conjunction with tests for total IgA, IgG and other individual isotypes, subclasses and structural forms and combinations of two or more of these.

In one embodiment, the biological sample is a blood or serum sample. Alternative biological samples include samples comprising cells expressing dIgA. Thus, in some embodiments, the process may be used to detect individual B-cells that express dIgA in the screening or isolation of immortalized B-cells.

In another embodiment, the biological sample is obtained from a subject. The subject is human or primate in some embodiments, and a mammalian or avian animal species other than a primate or human species in another embodiment. Various forms of recombinant pIgR are selected based on the target antibody of interest and species from which the antibody is derived.

As illustrated herein in one embodiment, the pIgR is recombinant HpIgA or RpIgR. Conveniently, in one embodiment, the recombinant pIgR or dIgA-binding variant has the transmembrane domain and/or the cytoplasmic domain deleted. In other embodiments, the recombinant pIgR comprises a heterologous detection or binding domain. In another embodiment, the recombinant pIgR or IgA-binding variant is recombinantly produced in a glycan deficient cell, such as a CHO cell.

In exemplary embodiments of the process, the recombinant pIgR is bound to a solid support.

In one embodiment, the biological sample is depleted of IgM or dIgA antibodies prior to use in the process. This allows the pIgR which binds to IgM and dIgA to be employed in assays to specifically detect dIgA. Similarly, depletion of dIgA (using, for example, R/HpIgR) facilitates the use of HpIgR in assays to specifically detect IgM. In some embodiments, IgG is depleted prior to sample use in order to reduce competition with dIgA. However, as competing antibodies are washed away in the present antibody/isotype capture formats, lack of such competition is an advantage of the process.

Any antigen of interest may be employed and in one non-limiting embodiments, the antigen of interest is an antigen of an infectious agent or an antigen associated with a condition of a subject that affects a mucosal surface or associated tissues. For example, infective agents include HIV, leprosy, syphilis, hepatitis, dengue virus, measles and rubella.

In one embodiment, the process further comprises contacting the biological sample with an anti-SC binding agent or anti-SC antibody wherein the anti-SC binding agent or anti-SC antibody binds SIgA and forms an SIgA-binding agent/antibody complex. In another embodiment, the process further comprises contacting a sample comprising the pIgR-dIgA complex with a denaturing solution to remove any SIgA from the complex and measuring the ratio of SIgA and dIgA in the biological sample.

In another aspect, the specification enables an antibody capture process for determining gut wall integrity in a test subject, the process comprising (i) obtaining a biological sample comprising antibodies from the test subject, (ii) contacting the biological sample with recombinant pIgR or a dIgA-binding variant, wherein the pIgR or variant binds dIgA and forms a pIgR-dIgA complex, and (iii) contacting the biological sample with a specific anti-SIgA binding agent or anti-SC binding agent/antibody wherein the anti-SIgA binding agent or anti-SC binding agent/antibody binds SIgA and forms an SIgA-binding agent/antibody complex, and (iv) measuring and comparing the level of the complex formed in (ii) with the level of the complex formed in (iii), wherein the ratio of SIgA to dIgA is compared to a corresponding level or ratio from a control subject and provides a measure of gut integrity/leakage.

In one embodiment of the process, the level or ratio of SIgA2/dIgA2 and/or SIgA1/dIgA1 are determined.

In another embodiment, the antibody capture process comprises (i) obtaining a biological sample comprising antibodies, (ii) contacting the biological sample with recombinant pIgR or a dIgA or IgM-binding variant, wherein the pIgR or variant binds IgM and/or IgA and forms a pIgR-IgM and/or pIgR-dIgA complex.

Alternatively, the antibody capture process may comprise (i) obtaining a biological sample comprising antibodies, (ii) contacting the biological sample with recombinant pIgR wherein the pIgR or variant binds IgM and forms a pIgR-IgM complex.

In another illustrated embodiment, a process is enabled for detecting the presence of antigen-specific dIgA in a subject, the process comprising (i) obtaining a biological sample comprising antibodies from a subject, (ii) contacting the sample with R/HpIgR and antigen and (iii) measuring the level of antigen-specific dIgA.

In another embodiment, a process is described for detecting the presence of antigen-specific IgM in a subject, the process comprising (i) obtaining a biological sample comprising antibodies from a subject, (ii) contacting the sample with a HpIgR and antigen and (iii) measuring the level of antigen-specific IgM.

In one embodiment, the process is for detecting the presence of antigen-specific IgM and dIgA in a subject, the process comprising (i) obtaining a biological sample comprising antibodies from a subject, (ii) contacting the sample with HpIgR and R/HpIgR and antigen and (iii) measuring the level of antigen-specific IgM and antigen specific dIgA.

In yet another aspect, the present specification enables a kit for assessing immune status in a subject, the kit comprising, (a) an immunographic device comprising a porous membrane operably connected to a sample portion, a test portion, and optionally a control portion; and further comprising a sucker portion, portion comprising a recombinant pIgR molecule or dIgA-binding variant thereof, a portion comprising an antigen of interest and optionally a conjugate portion; and b) instructions for using the immunographic device to detect the presence of antigen specific dIgA antibody in a biological sample obtained from the subject.

As described herein in relation to the process, in some embodiments of the kit, the pIgR is HpIgR and/or R/HpIgR. In some embodiments, the recombinant pIgR or dIgA-binding variant has the transmembrane domain and/or the cytoplasmic domain deleted. In one embodiment, the recombinant pIgR comprises a heterologous detection or binding domain. In yet another embodiment, the recombinant pIgR or IgA-binding variant is recombinantly produced in a glycan deficient cell.

In one embodiment, the recombinant pIgR is bound to a solid support.

In one embodiment, the biological sample is depleted of IgM or dIgA antibodies prior to use in the process. The kits and reagents contained therein of the present invention are for use ex vivo.

Any antigen may be employed however in one embodiment, the antigen of interest is an antigen of an infectious agent or an antigen associated with a condition of a subject that affects a mucosal surface or associated tissues. Illustrative infectious agents are selected from HIV, leprosy, syphilis, hepatitis, dengue virus, measles and rubella. The detection of elevated levels of antigen specific dIgA recombinant pIgR relative to control levels facilitates diagnosis and the selection and treatment options. In some embodiments, a method of treatment is contemplated comprising requesting a test for antigen-specific dIgA levels and administered treatment to the diagnosed subject if the test is positive for an infection or condition.

In another embodiment, the kit further comprises an anti-SIgA binding agent/antibody or anti-SC antibody, wherein the anti-SIgA binding agent/antibody or anti-SC antibody binds SIgA and forms an SIgA-binding agent/antibody complex.

In another aspect, recombinant pIgR is provided which is suitable for use in capturing or detecting dIgA and/or IgM. Illustrative recombinant pIgRs include R/HpIgR or HpIgR or a dIgA and/or IgM binding variant of R/HpIgR or HpIgR. Illustrative amino acid and nucleotide sequences are set out in SEQ ID NO:1 to 20, bearing in mind that some of these sequence encode or provide a CD4 cytoplasmic domain which is entirely optional and may be deleted, modified, supplemented or replaced with other binding or detection molecules known in the art. Once the subject invention is contemplated, useful variants of recombinant pIgR will be apparent to the skilled person and readily made and tested.

DETAILED DESCRIPTION OF THE FIGURES SUPPORTING AND DESCRIBING THE SUBJECT PROCESSES AND KITS

If figures contain colour representations or entities, coloured versions of the figures are available from the Patentee upon request or from an appropriate Patent Office. A fee may be imposed if obtained from a Patent Office.

FIG. 1 provides a schematic of the production of dIgA and its secretion at mucosal surfaces as SIgA. Most dIgA produced in the submucosal tissues is subsequently bound to pIgR and transcytosed to the mucosal surface, where pIgR is cleaved to produce SIgA (or free SC), with SIgA constituting a first layer of defense against pathogens. pIgR binding is dependent on the presence of J-chain in polymeric Ig, and binding occurs to both IgM and dIgA in humans.

Figure 2:
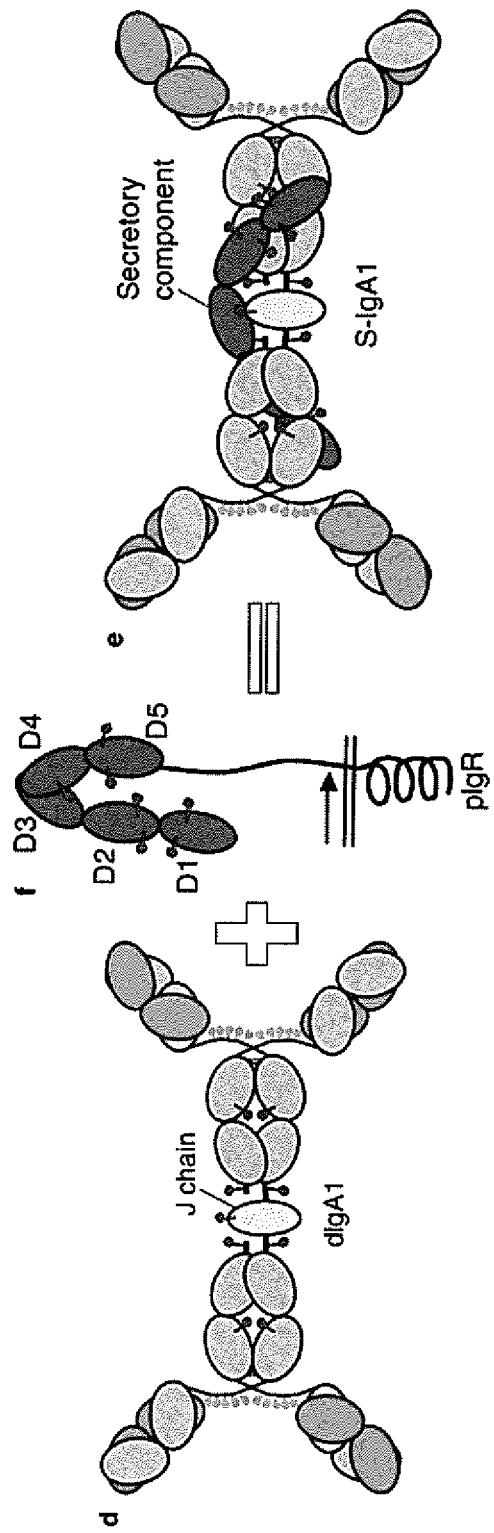

FIG. 2 provides a representation of the structure of dIgA1 and its interaction with pIgR which is then cleaved to give SIgA1. The associated Secretory component portion of pIgR interacts with both J-chain and the Fc domains of both individual IgA molecules.

FIG. 3 provides a representation of the structure of chimeric R/HpIgR relative to human (HpIgR), and the R/HpIgR that is fused to the cytoplasmic domain of human CD4 at its C-terminus. The R/HpIgR and other forms are expressed and secreted at high levels in 293T cells, shown by the detection of R/HpIgR using coomassie brilliant blue staining of SDS-PAGE gel of the crude supernatant (SN) from transiently transfected cells. R/HpIgR-cyto is readily purified to homogeneity and high concentration by affinity chromatography with an immobilised matrix of monoclonal antibody 4B4 directed against the cytoplasmic domain of CD4 (Pure). Either pure pIgR or crude SN can be used in detection or binding of dIgA as preferred.

Figure 4:
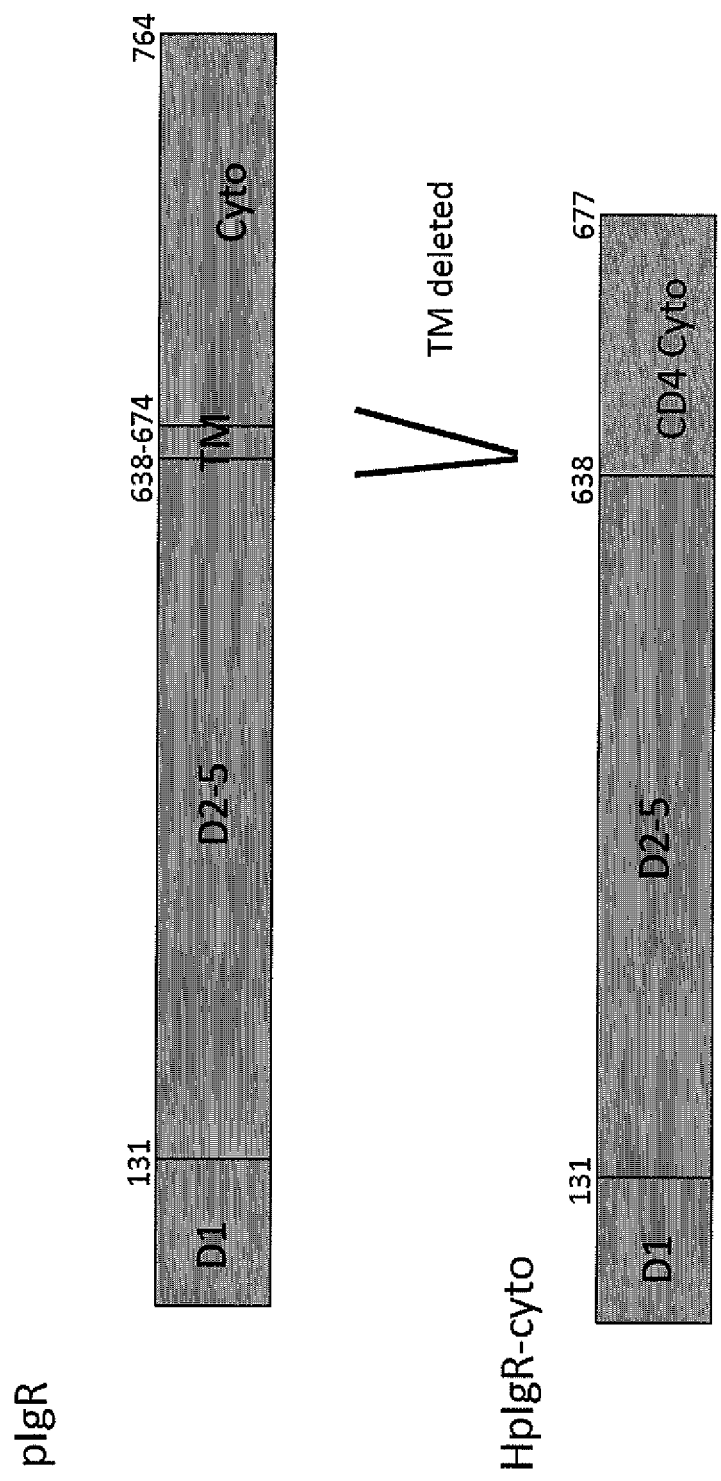

FIG. 4 provides a schematic representation of the structure of full-length (native) pIgR (TOP), relative to the recombinant form HpIgR-cyto (bottom), in which the transmembrane domain (TM) and cytoplasmic domain (cyto) of pIgR have been replaced with the cytoplasmic domain of human CD4. Because of the deletion of the TM domain, the product is secreted from cells rather than being retained at the cell surface.

Figure 5:
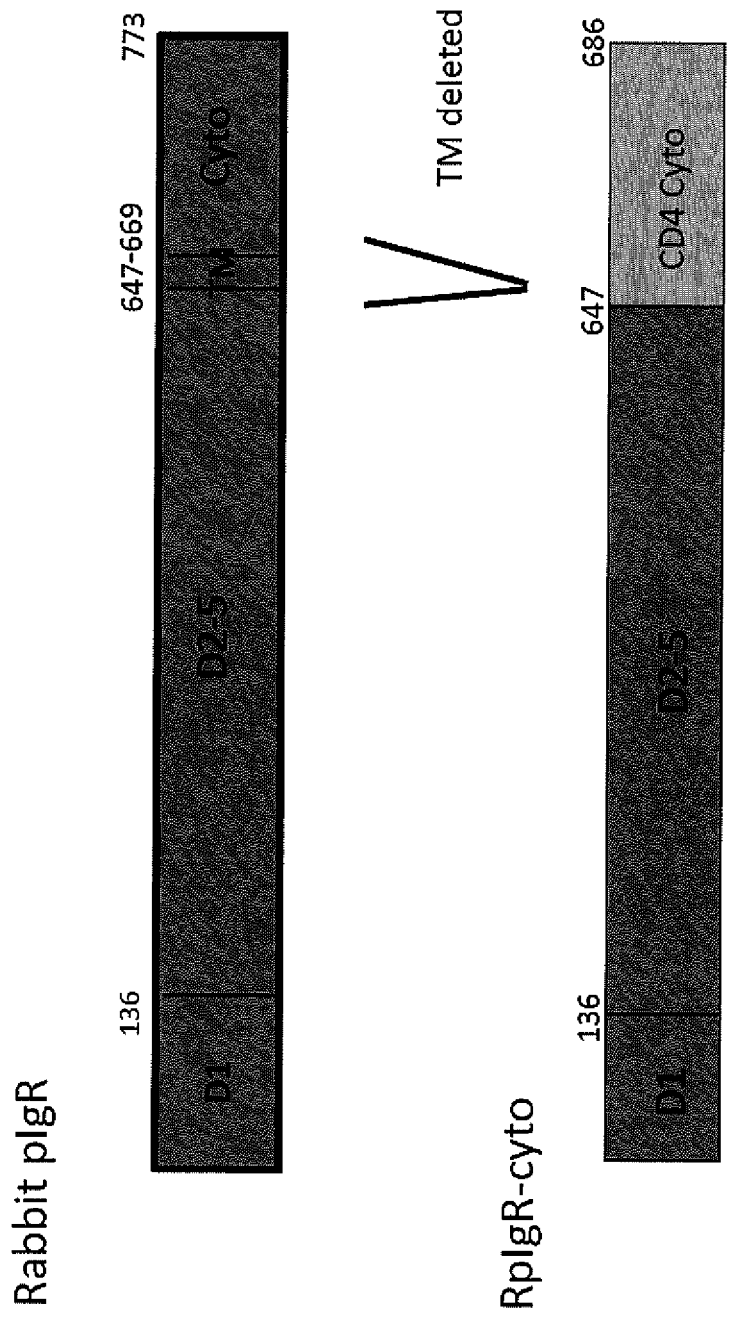

FIG. 5 provides a schematic of the structure of full-length (native) rabbit pIgR (TOP), relative to the recombinant form RpIgR-cyto (bottom), in which the transmembrane domain (TM) and cytoplasmic domain (cyto) of rabbit pIgR have been replaced with the cytoplasmic domain of human CD4. Because of the deletion of the TM domain, the product is secreted from cells rather than being retained at the cell surface.

Figure 6:
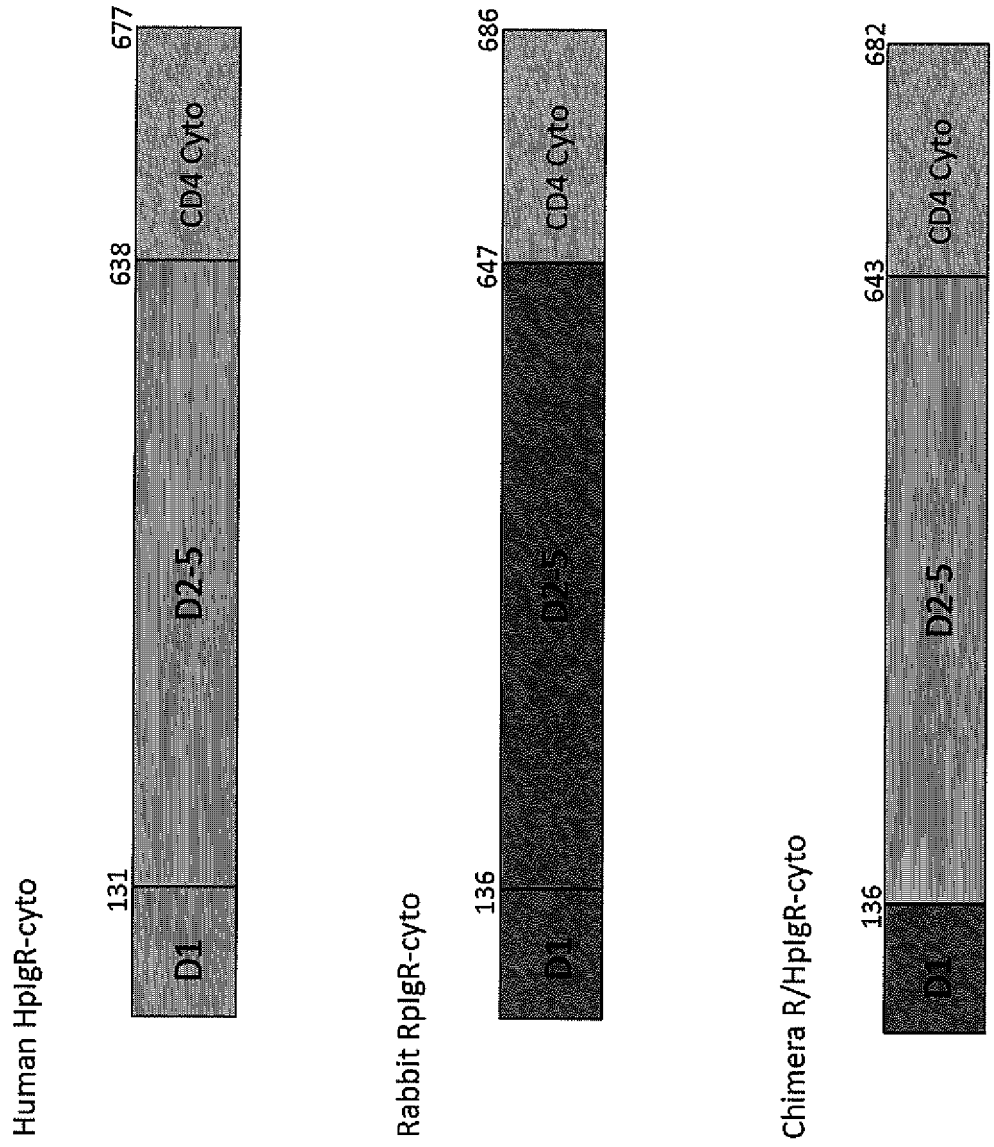

FIG. 6 provides a schematic of the structure HpIgR cyto, RpIgR-cyto, and chimeric R/HpIgR-cyto. These forms of pIgR demonstrate highly efficient binding to solid surfaces such as polystyrene ELISA plates (Nunc IMMULON® or similar) through interaction of the CD4 cyto domain with the plastic or other solid surfaces.

Figure 7:
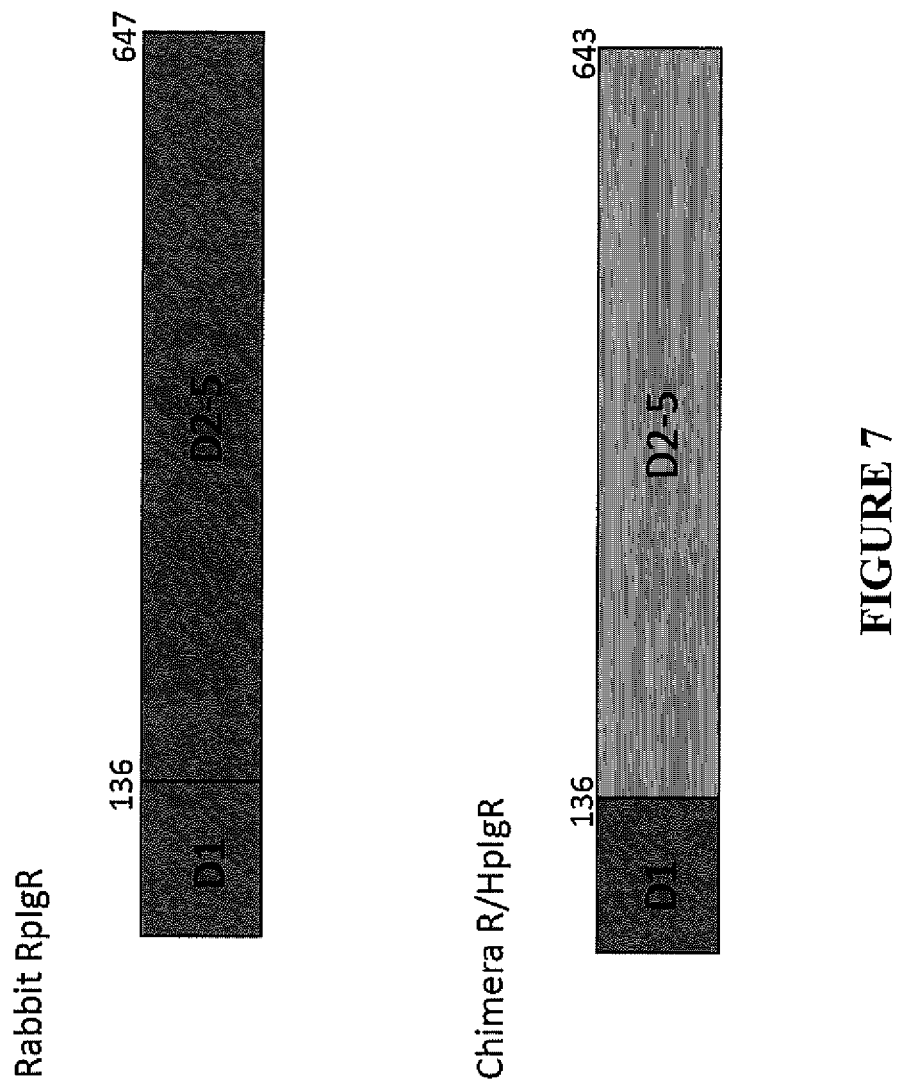

FIG. 7 provides a schematic of the structure RpIgR and chimeric R/HpIgR. In the absence of the CD4 cyto domain, the RpIgR can be detected by reactivity with antibodies against the rabbit pIgR, and the chimera R/HpIgR can be detected by reactivity with antibodies against the rabbit (domain 1) and/or human (domain 2-5) pIgR. The preferred antibodies must be able to interact with pIgR when it is bound to dIgA, not only to free pIgR.

Figure 8:
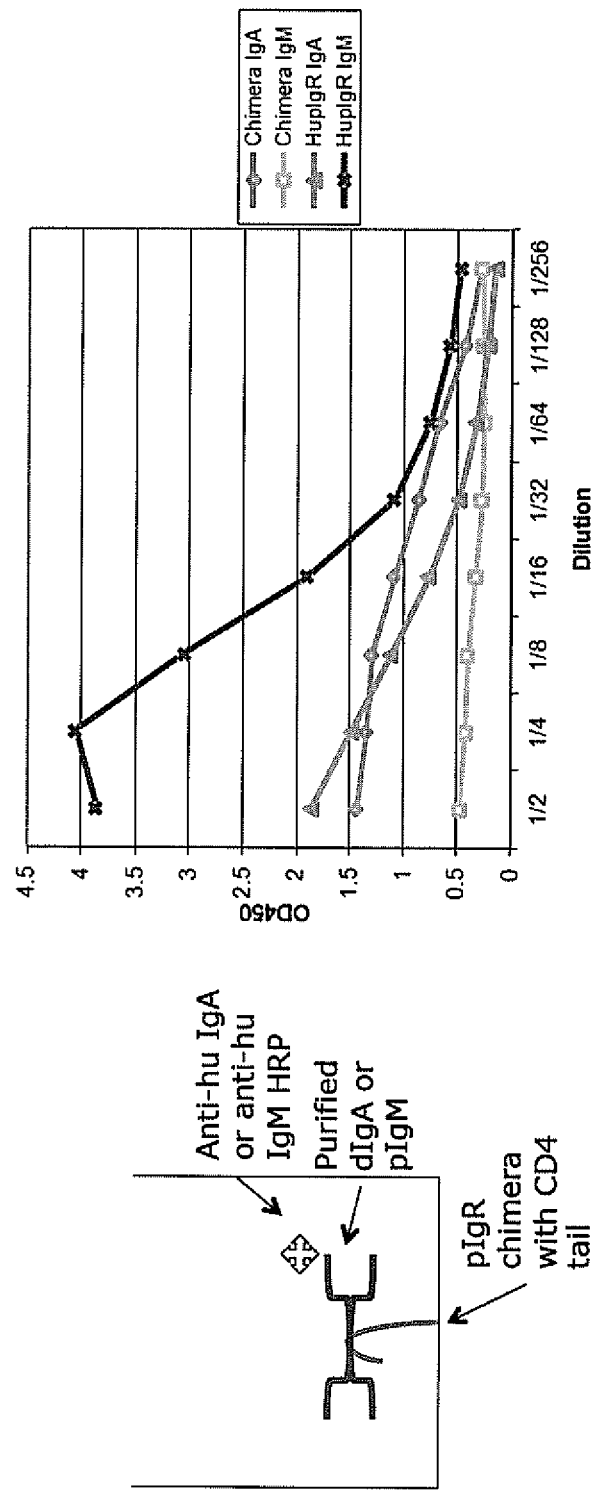

FIG. 8 provides the results of ELISA comparing the binding of HpIgR and R/HpIgR to human IgM and dIgA. HpIgR or R/HpIgR were immobilised on 96-well Nunc IMMULON® plates overnight at 4° C. Dilutions of purified human IgM or dIgA in PBS were bound to the immobilised pIgR forms overnight. After washing, the captured IgM or dIgA were detected using anti-IgM or anti-IgA conjugated to horseradish peroxidase (HRP) and colorimetric substrate TMB. The results demonstrate that HpIgR shows preferential binding to IgM (magenta) as well as binding to dIgA (green), whereas R/HpIgR shows greatly reduced binding to IgM (yellow) but retains strong binding to dIgA (blue).

FIG. 9 provides the results of ELISA comparing the detection of immobilised dIgA using R/HpIgR. Dilutions of purified dIgA or no dIgA (mock) were immobilised on 96-well Nunc IMMULON® plates that were previously coated with anti-IgA, so that the dIgA was bound to the plate by antibody-antigen interaction rather than passive absorption. The dIgA was detected using R/HpIgR ("tailless") or no pIgR ("mock"), anti-secretory component and anti-mouse HRP and TMB substrate. The results demonstrate R/HpIgR is able to detect dIgA at the lowest concentration tested (31 ng/ml) with strong signal in ELISA with negligible background.

Figure 10:
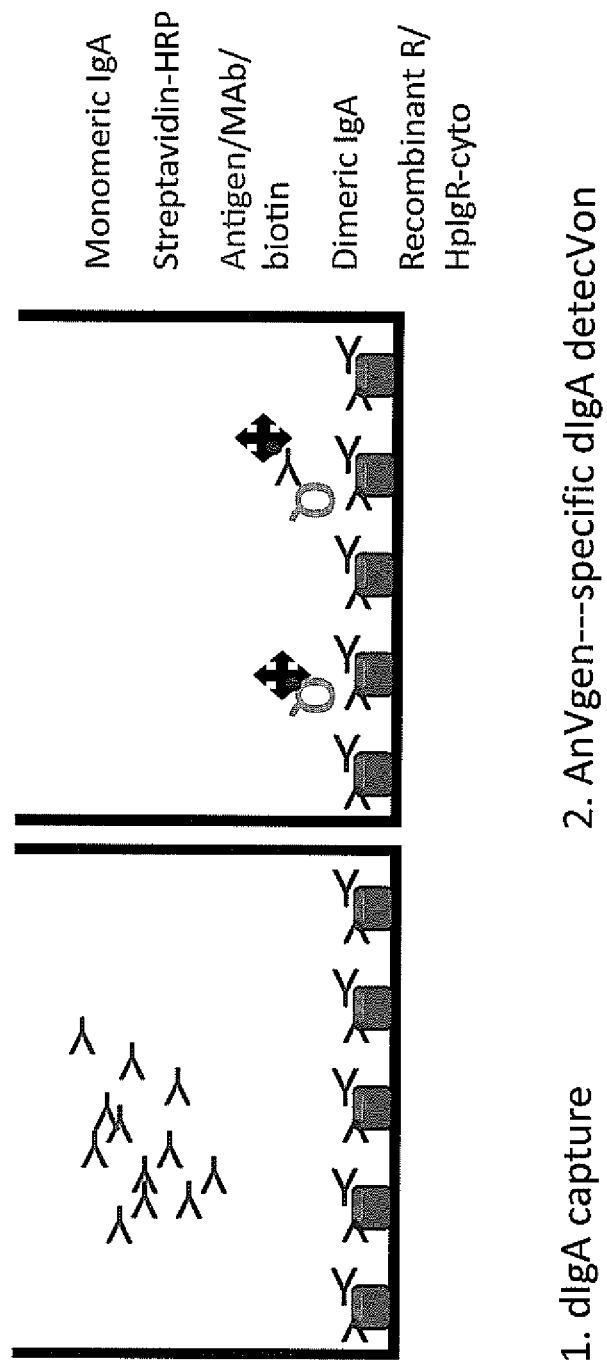

FIG. 10 is a schematic of one preferred experimental approach for detecting the presence of antigen-specific dIgA in a sample such as human serum or plasma. Recombinant R/HpIgR-cyto is immobilised on the ELISA plate, and incubated with serum or other samples. Dimeric IgA is captured on the solid phase, and after washing to remove other sample components (such as IgA and IgG that are not captured, left), the presence of antigen-specific dIgA is detected by sequential addition of antigen that is either biotinylated, or reacted with a biotinylated monoclonal antibody against the antigen, and streptavidin-HRP. In this way, any antigen that is immobilised by reaction with antigen-specific dIgA will give a signal through the biotin-streptavidin interaction.

Figure 11:
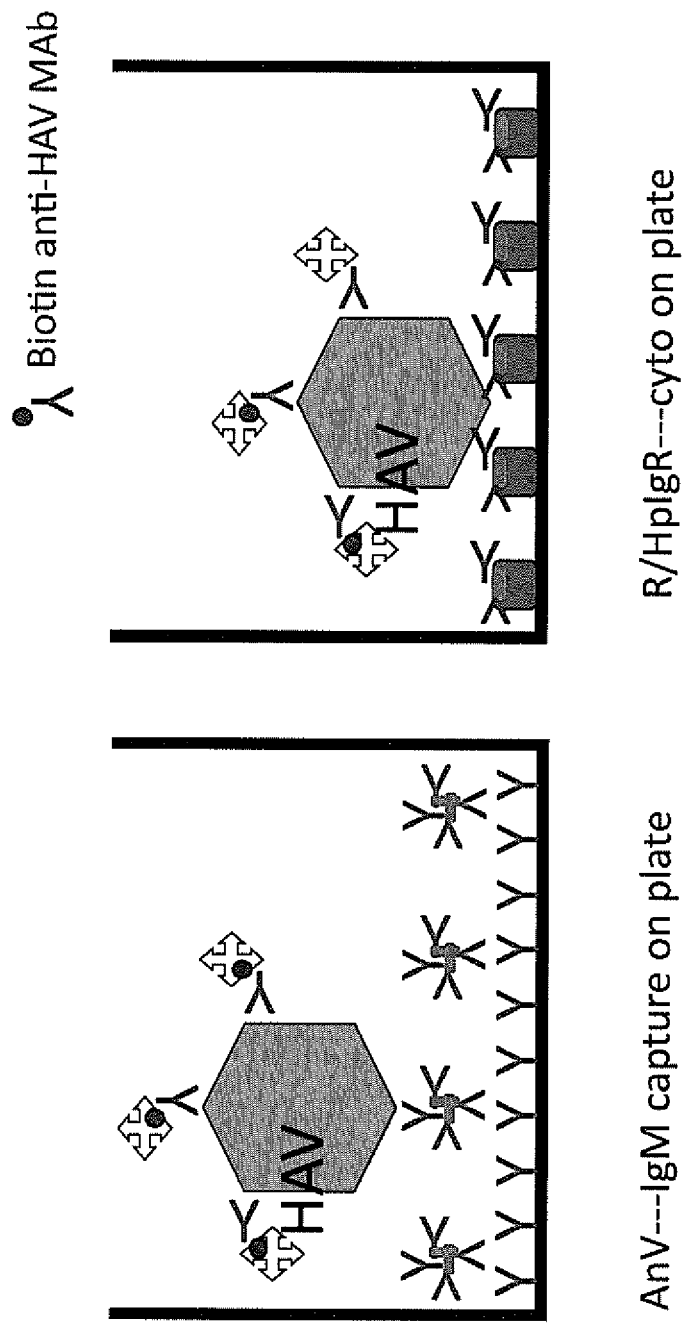

FIG. 11 is a schematic of one preferred experimental approach for detecting the presence of hepatitis A virus-specific dIgA in serum (right), compared to detection of HAV-specific IgM using the standard method of anti-IgM capture (left).

Figure 12:
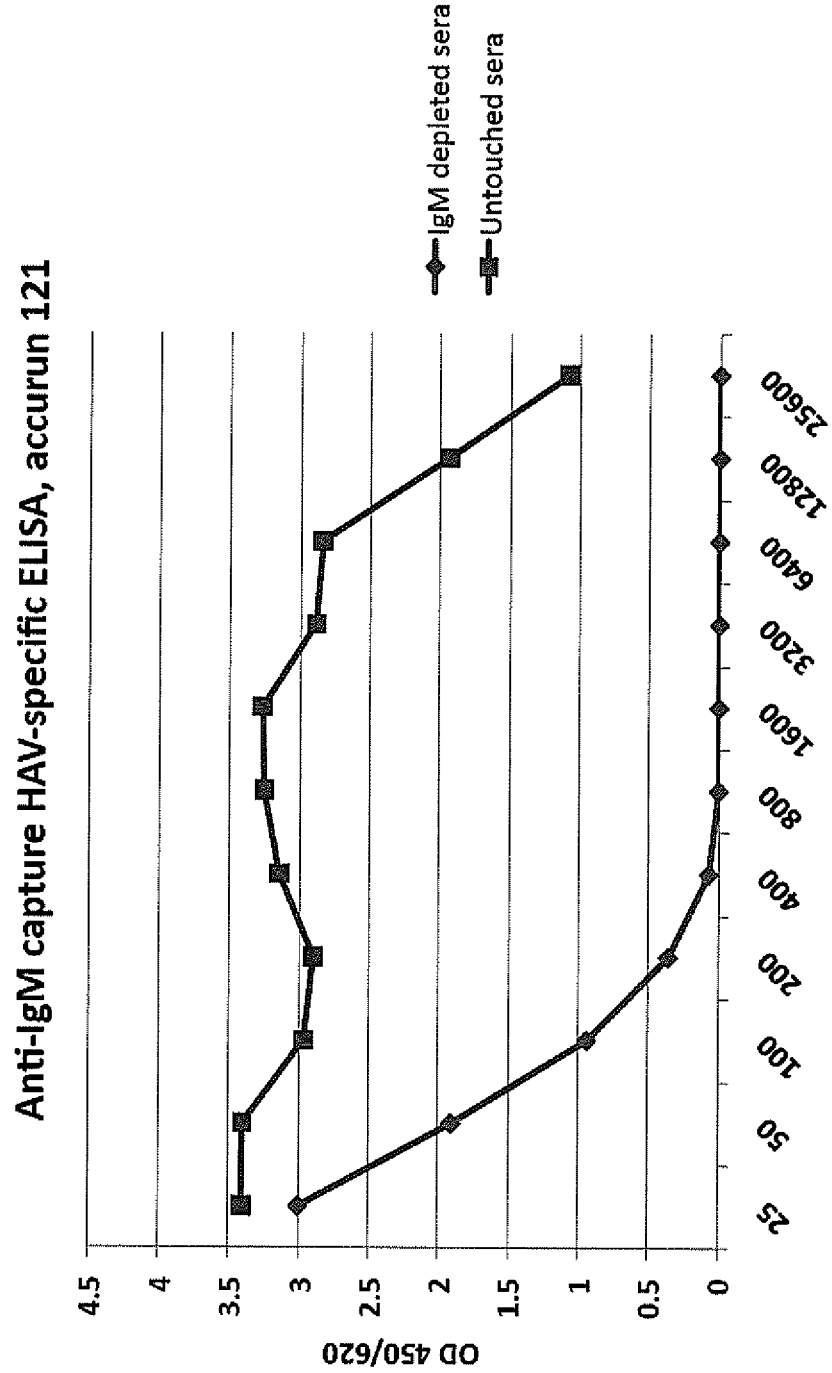

FIG. 12 provides the results of ELISA demonstrating the detection of HAV-specific IgM in IgM capture, using serial dilutions of serum from a patient with acute HAV infection (ACCURUN® HAV panel sample 121). The serum sample is either untouched before dilution (untouched, purple) or substantially depleted of IgM using Capture-Select IgM (BAC) (red). The results show that this IgM depletion method reduces the level of HAV-specific IgM in the sample by around 256-fold compared to untouched serum.

Figure 13:
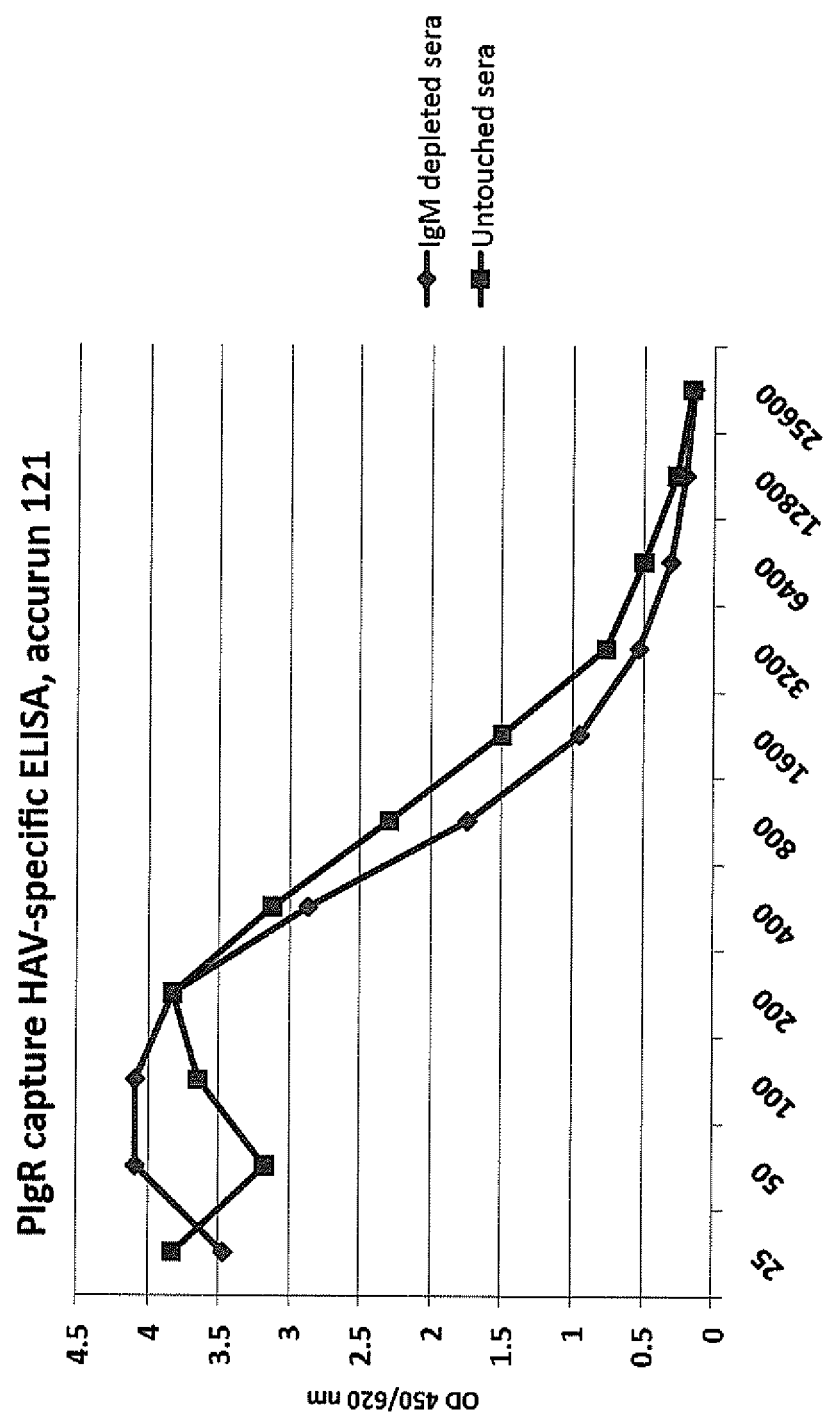

FIG. 13 provides the results of ELISA demonstrating the detection of HAV-specific dIgA in R/HpIgR capture, using serial dilutions of serum from a patient with acute HAV infection (ACCURUN® HAV panel sample 121). The serum sample is either untouched before dilution (untouched, purple) or substantially depleted of IgM using Capture-Select IgM (BAC) (red). The results show firstly the strong signal that is obtained demonstrating the detection of HAV-specific dIgA, and secondly that this signal is specific for dIgA not IgM because the IgM depletion method did not substantially reduce the level of HAV-specific reactivity compared to untouched serum, in contrast to the results shown in FIG. 12 for IgM detection.

Figure 14:
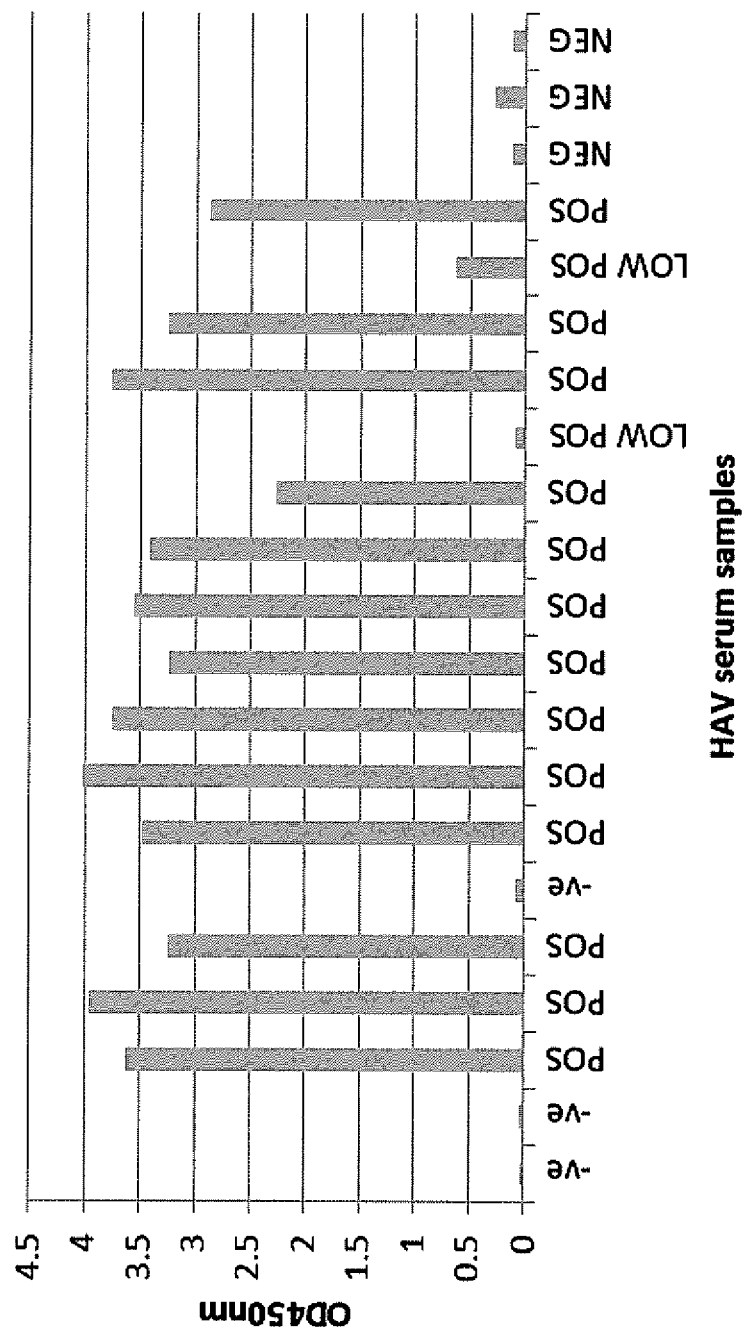

FIG. 14 provides the results of ELISA demonstrating the detection of HAV-specific dIgA in R/HpIgR capture, using sera from patients with or without acute HAV infection (ACCURUN® HAV panel, positive (POS), low positive (LOW POS), or negative (NEG)). The results show the strong detection of HAV-specific dIgA in all POS samples and in one of two LOW POS samples, with minimal background reactivity in NEG samples, demonstrating the utility of R/HpIgR capture of antigen-specific dIgA for the diagnosis of acute HAV infection.

Figure 15:
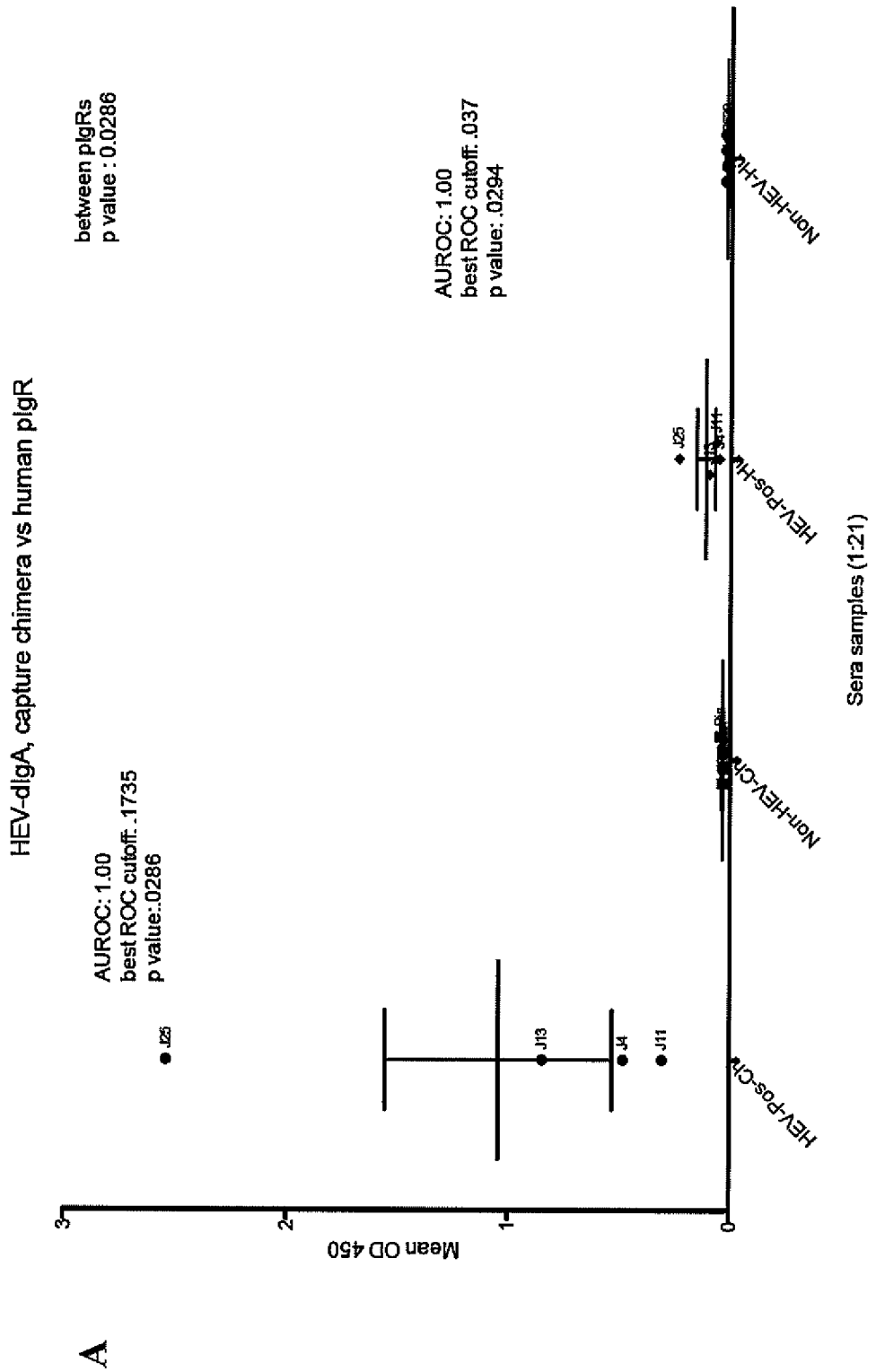

FIG. 15 provides the results of ELISAs demonstrating the detection of hepatitis E virus (HEV)-specific dIgA in R/HpIgR capture or HpIgR capture, using sera from patients with or without acute HEV infection. On the left, the ELISA OD of individual samples is shown, demonstrating the utility of R/HpIgR capture of antigen-specific dIgA for the diagnosis of acute HEV infection, with lower but still significant utility of HpIgR capture for this purpose, and negligible background reactivity in either example. On the right, the reactivity of serial dilutions of each serum sample is shown, confirming the utility of R/HpIgR capture and lower utility of HpIgR capture for diagnosis of acute HEV infection. It is likely that the lower utility of HpIgR capture in these examples is due to the much higher overall concentration of IgM in serum versus dIgA, resulting in only a low proportion of the IgM captured by HpIgR being specific for HEV.

Figure 16:
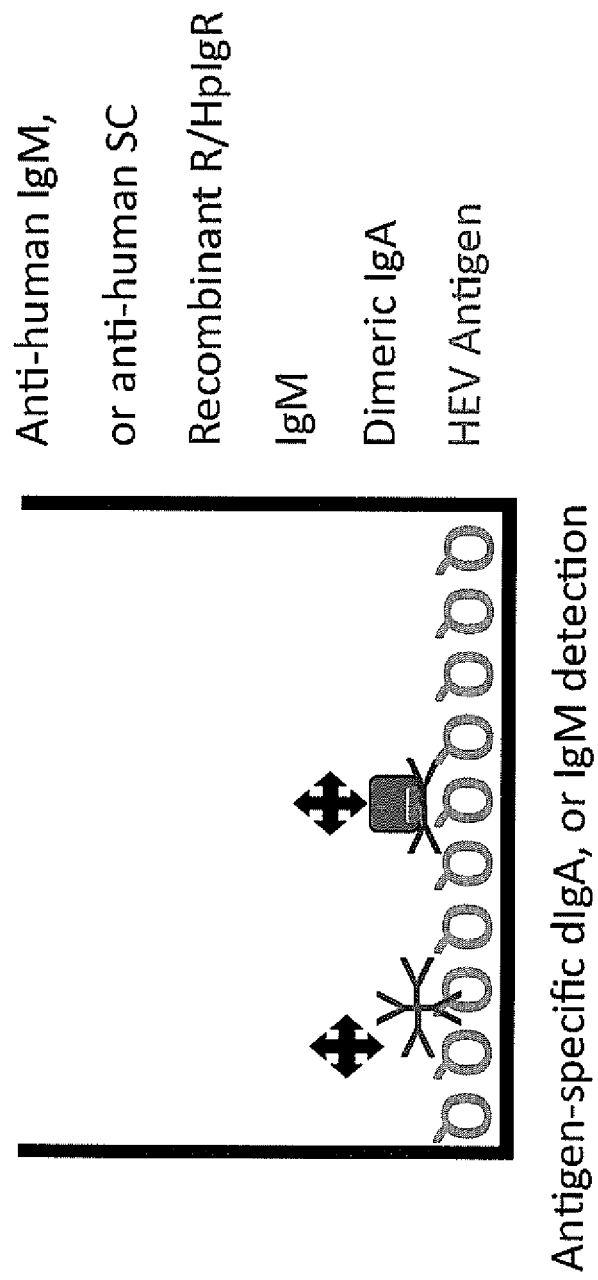

FIG. 16 is a schematic of a second preferred method for detection of antigen-specific dIgA (or IgM), in which antigen is coated directly onto the ELISA plate (in this case, hepatitis E virus (HEV) antigen). Serum samples are applied to the plate and antigen-specific antibodies, including IgM and dIgA, bind to the antigens and are then detected with either anti-IgM HRP, or R/HpIgR and anti-human SC HRP. After final washing, signal is generated with TMB substrate.

Figure 17:
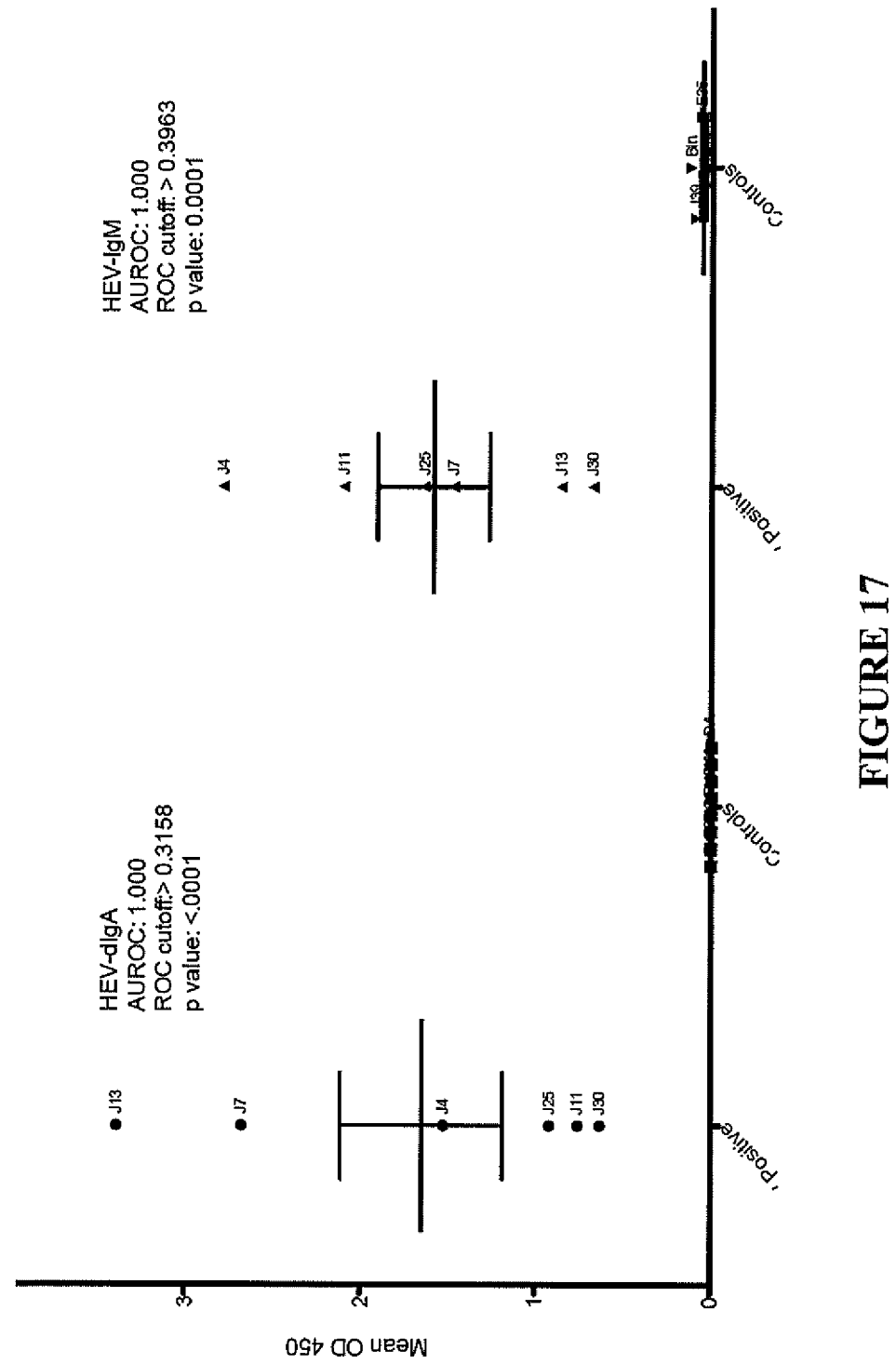

FIG. 17 provides the results of a comparison of HEV-specific dIgA versus HEV-specific IgM. Both methods are able to detect all HEV-infected patients with strong ELISA signals, compared to extremely low background for control (HEV-negative) patients in the dIgA assay, and low background in the IgM assay. Notably, some samples show higher levels of dIgA compared to IgM (sample J13, J7), while others show higher levels of IgM compared to dIgA (J4, J11). This demonstrates that the dIgA and IgM responses in patients are independent, and suggests that a combination of both IgM and dIgA detection may be useful in some desirable assay formats.

FIG. 18 provides the results of a comparison of HEV-specific dIgA versus HEV-specific IgM using sera that are either untouched, or substantially depleted of IgM using Capture-Select IgM, and then serially diluted. The results confirm that the IgM assay is specific for IgM, because the reactivity is ablated by IgM depletion, whereas the dIgA assay is predominantly specific for dIgA and not IgM, because the reactivity is only slightly affected by IgM depletion.

Figure 19:
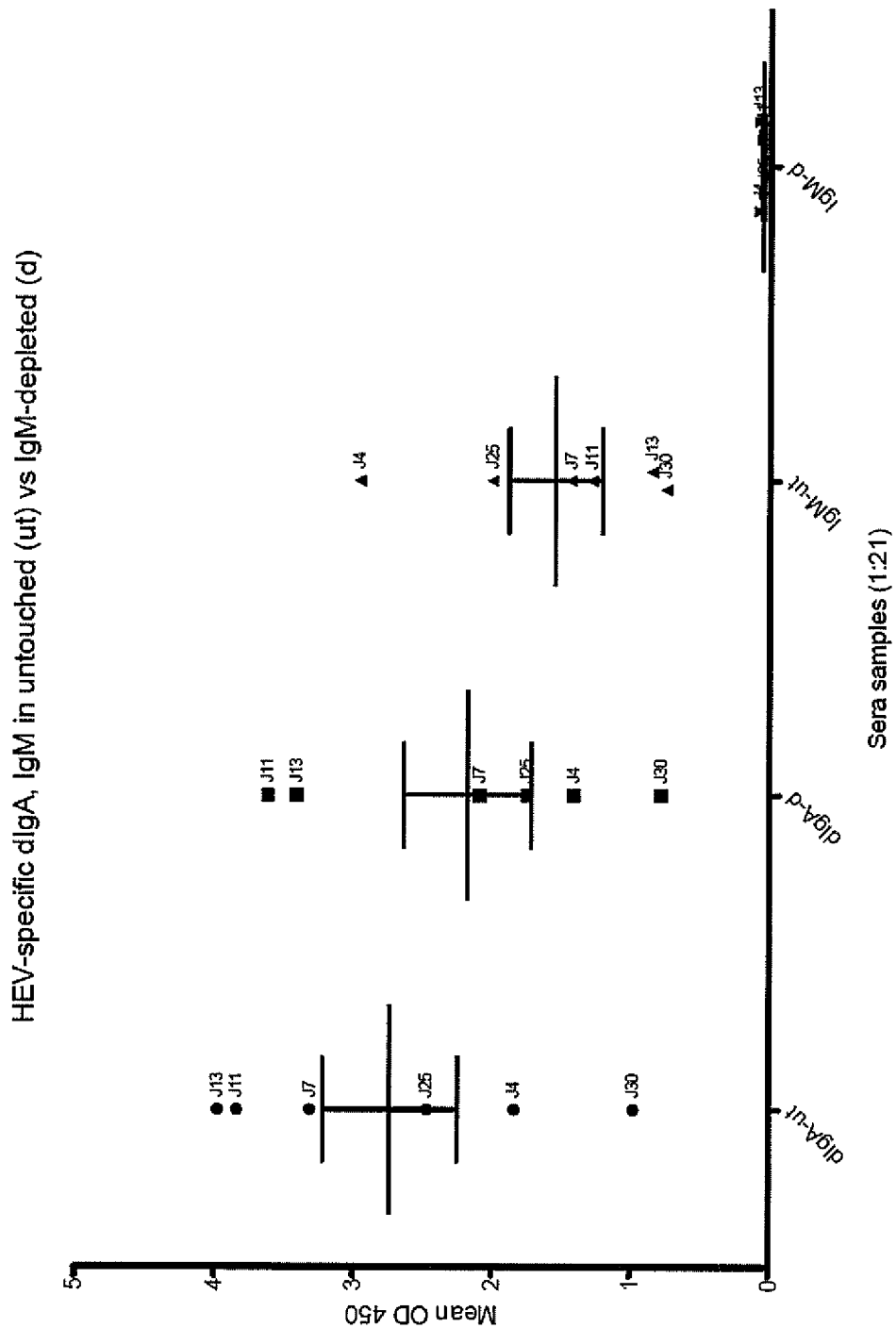

FIG. 19 provides the results of a comparison of HEV-specific dIgA versus HEV-specific IgM using sera that are either untouched, or substantially depleted of IgM using Capture-Select IgM. The results confirm that the IgM assay is specific for IgM, because the reactivity is ablated by IgM depletion, whereas the dIgA assay is predominantly specific for dIgA and not IgM, because the reactivity is only slightly affected by IgM depletion.

Figure 20:
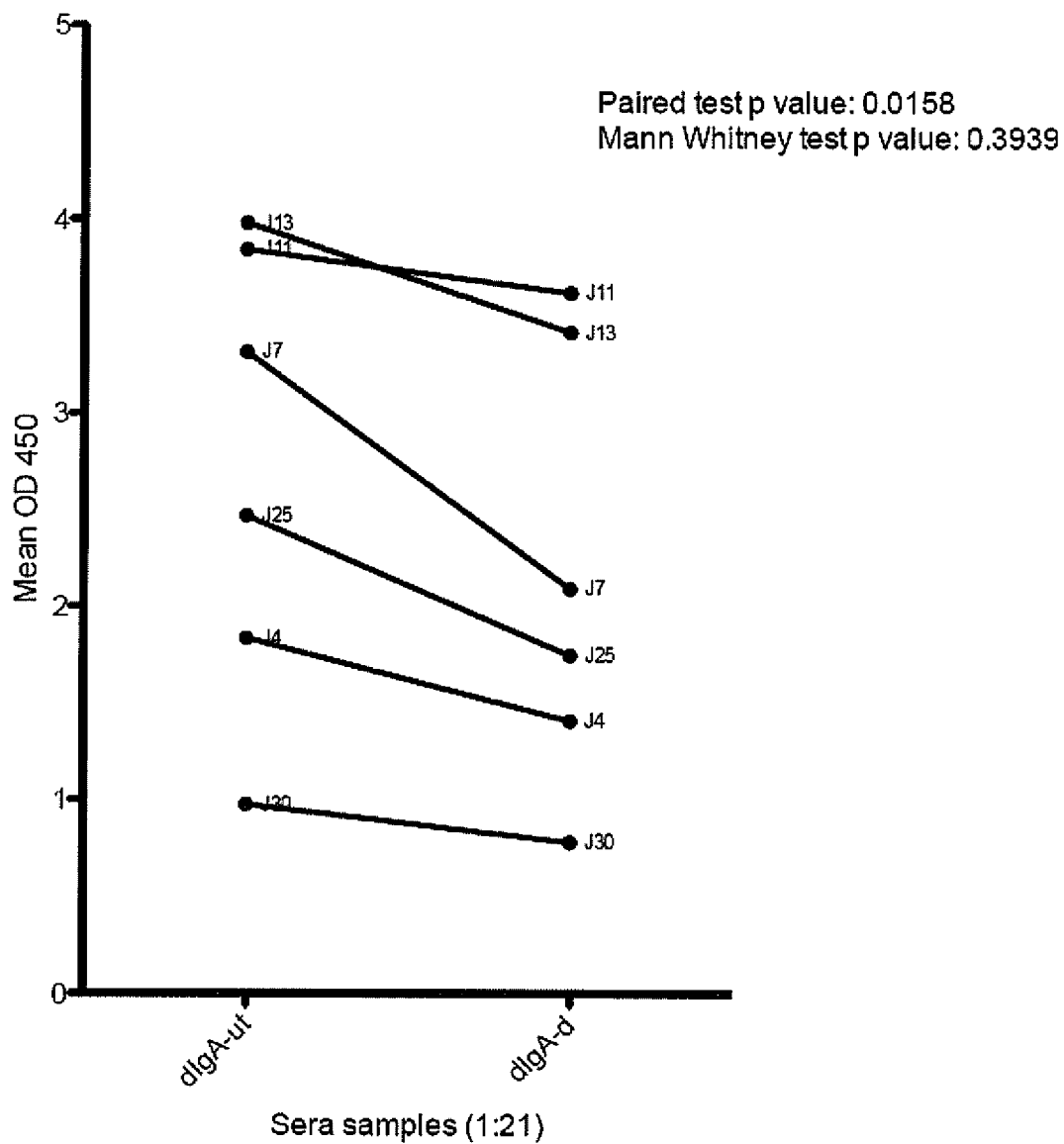
Figure 20:
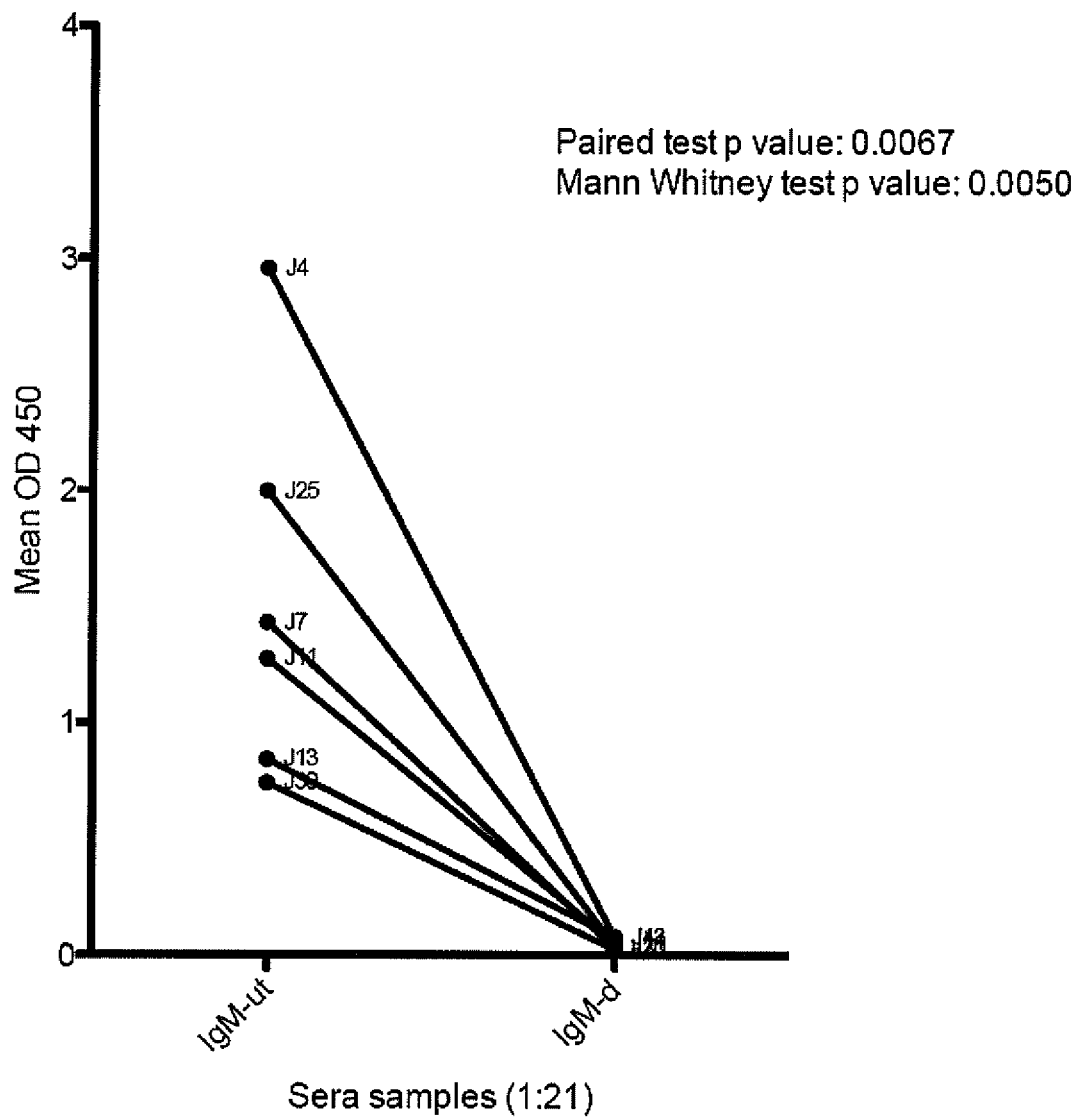

FIG. 20 provides the results of comparison of HEV-specific dIgA versus HEV-specific IgM using sera that are either untouched, or substantially depleted of IgM using Capture-Select IgM. The results confirm that the IgM assay is specific for IgM, because the reactivity is ablated by IgM depletion, whereas the dIgA assay is predominantly specific for dIgA and not IgM, because the reactivity is only slightly affected by IgM depletion. The reduction in dIgA activity following IgM depletion is statistically significant when using a paired T-test to compare samples before and after depletion, but is not significant when using a Mann-Whitney test to compare the overall sample sets before and after depletion.

Figure 21:
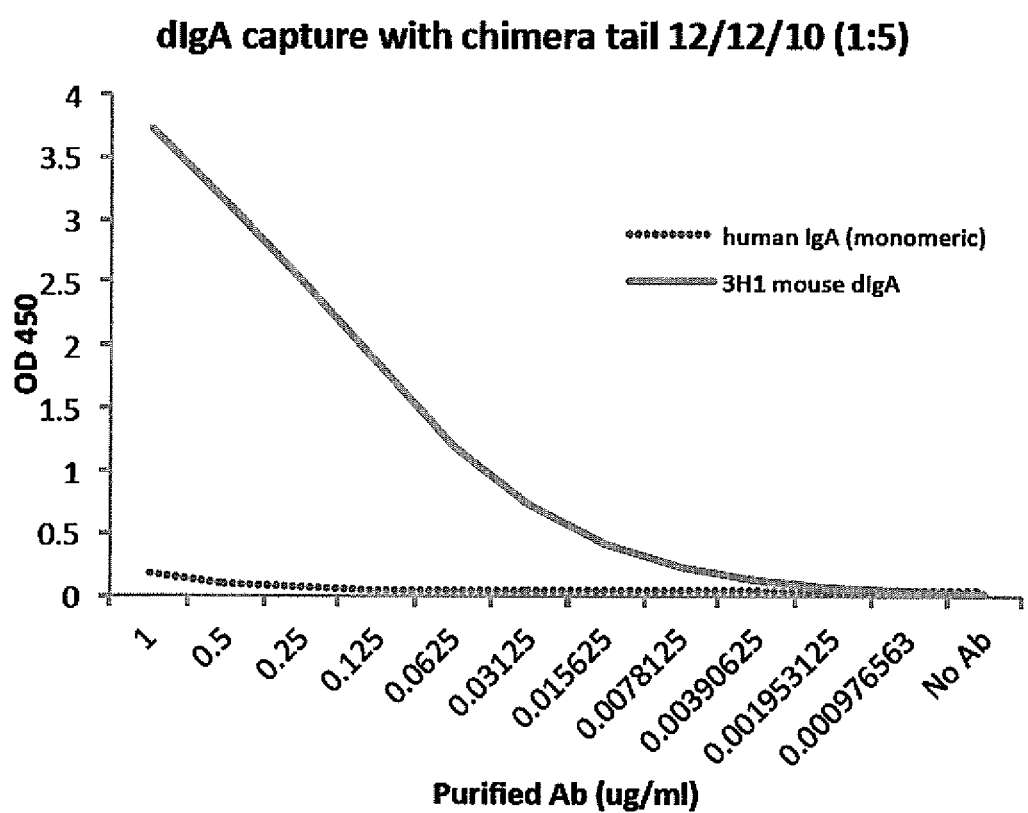
Figure 21:
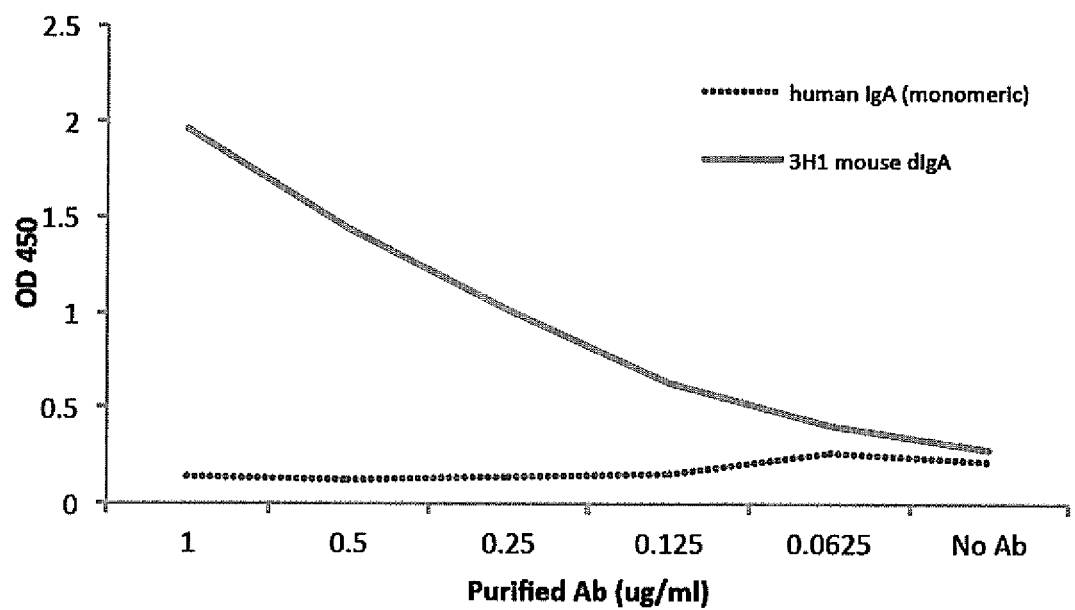

FIG. 21 provides the results of ELISA demonstrating that the R/HpIgR can be used in both capture (A) and detection (B) of mouse dimeric IgA, with negligible background reactivity to monomeric (human) IgA. A. Dilutions of purified mouse IgA monoclonal antibody 3H1 (anti-HAV) or purified monomeric human IgA were coated on plates and detected with R/HpIgR and anti-SC antibodies. B. R/HpIgR was coated on plates and dilutions of purified mouse IgA monoclonal antibody 3H1 or purified monomeric human IgA were allowed to bind overnight, then detected with anti-mouse IgA or anti-human IgA. The binding of IgA from diverse species to human or rabbit pIgR is known in the art, and this demonstrates that the novel pIgR strategy described herein has utility for diagnosis of infection in other species. It is also useful for purification of dIgA from other species—e.g., purification of mouse, rabbit or rate IgA monoclonal antibodies versus jacalin agarose.

Figure 22:
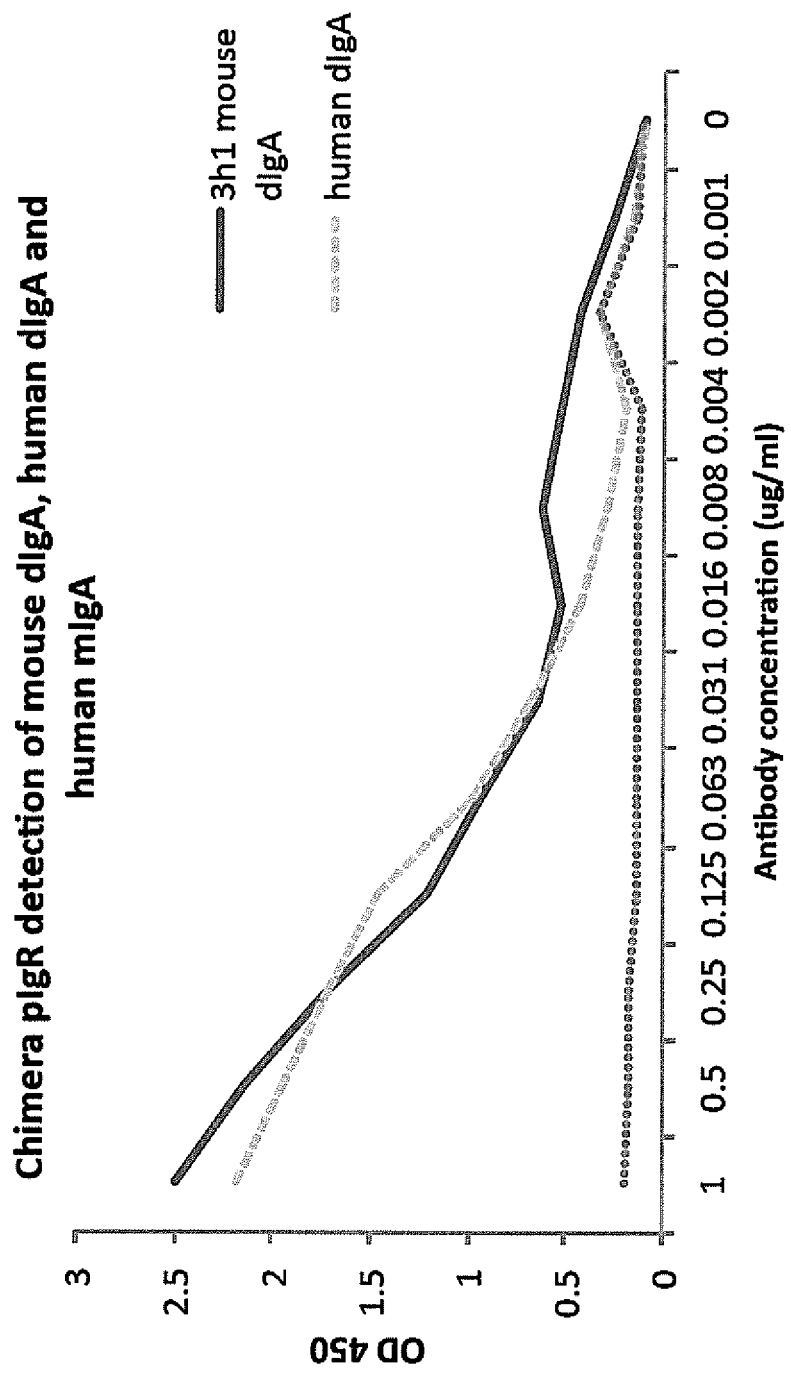

FIG. 22 provides the results of ELISA demonstrating that the R/HpIgR is equally effective for detection of mouse dimeric IgA and human dimeric IgA, with negligible background reactivity to monomeric human IgA. A. Dilutions of purified mouse IgA monoclonal antibody 3H1 (anti-HAV) or purified dimeric or monomeric human IgA were coated on plates and detected with R/HpIgR and anti-SC antibodies.

Figure 23:
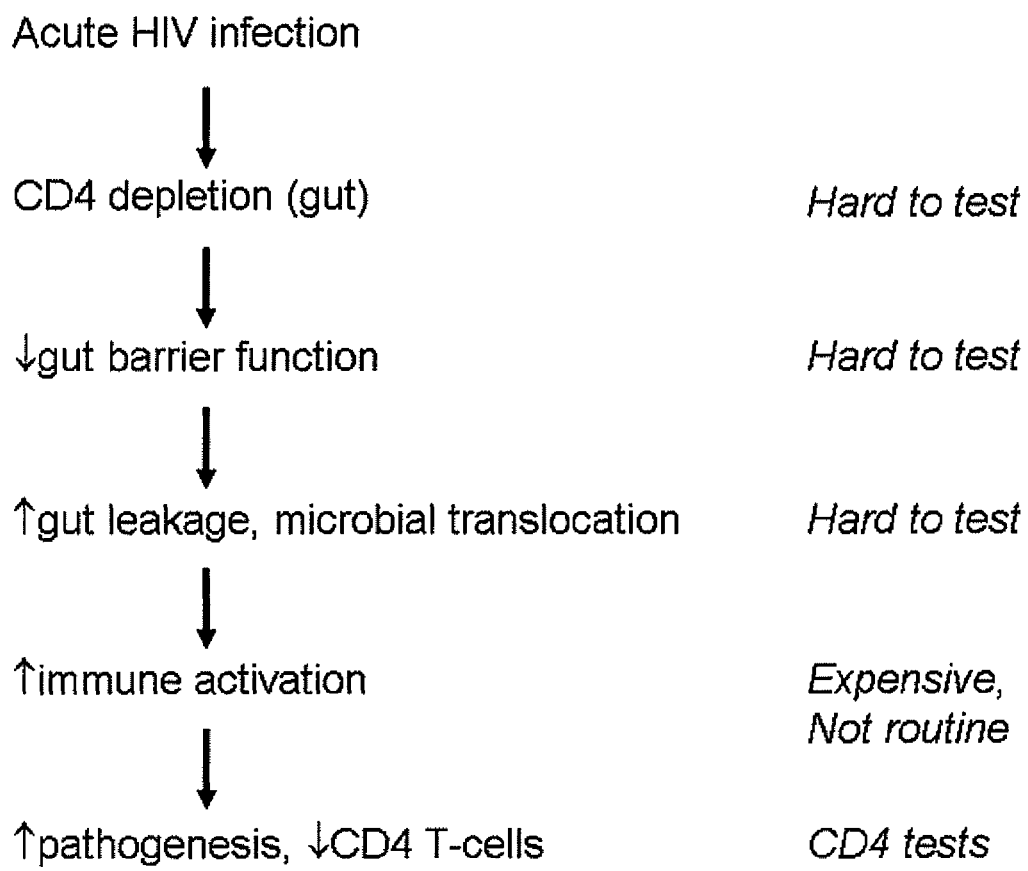

FIG. 23 provides a model outlining the pathogenic consequences of acute human immunodeficiency (HIV) infection, which leads to rapid CD4 depletion in the gut as well as the periphery, with a subsequent reduction in gut barrier function, increased leakage of gut contents and microbial translocation, leading to increased immune activation which drives pathogenesis and further reduction of CD4 T-cell levels (Brenchley et al, *Nat Med* 12: 1365-1371, 2006). There is an unmet need for simple, standardised assays that can detect one or more of these steps in the pathogenesis pathway so that appropriate interventions can be provided to patients, with only CD4 testing having been integrated into the standard of care for HIV-infected patients. Detection of CD4 depletion in the gut requires endoscopy; detection of decreased gut barrier function requires complicated sugar challenge studies or other methods; detection of gut leakage and microbial translocation can be achieved using markers such as bacterial LPS or 16sRNA in serum but results are highly variable due in part to the wide variation in gut microbiota between individuals; immune activation requires complex Flow cytometry protocols that are difficult to standardise across instruments/operators.

Figure 24:
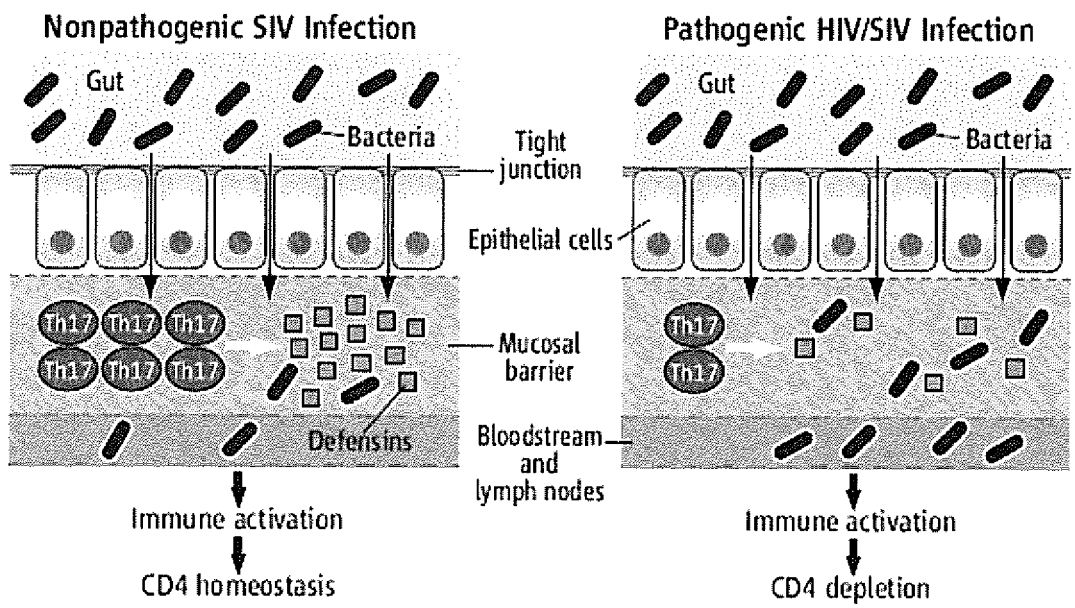

FIG. 24 is a schematic of the increase in microbial translocation due to gut leakage induced by pathogenic HIV or SIV infection, compared to normal low levels of translocation in nonpathogenic SIV infection.

Figure 25:
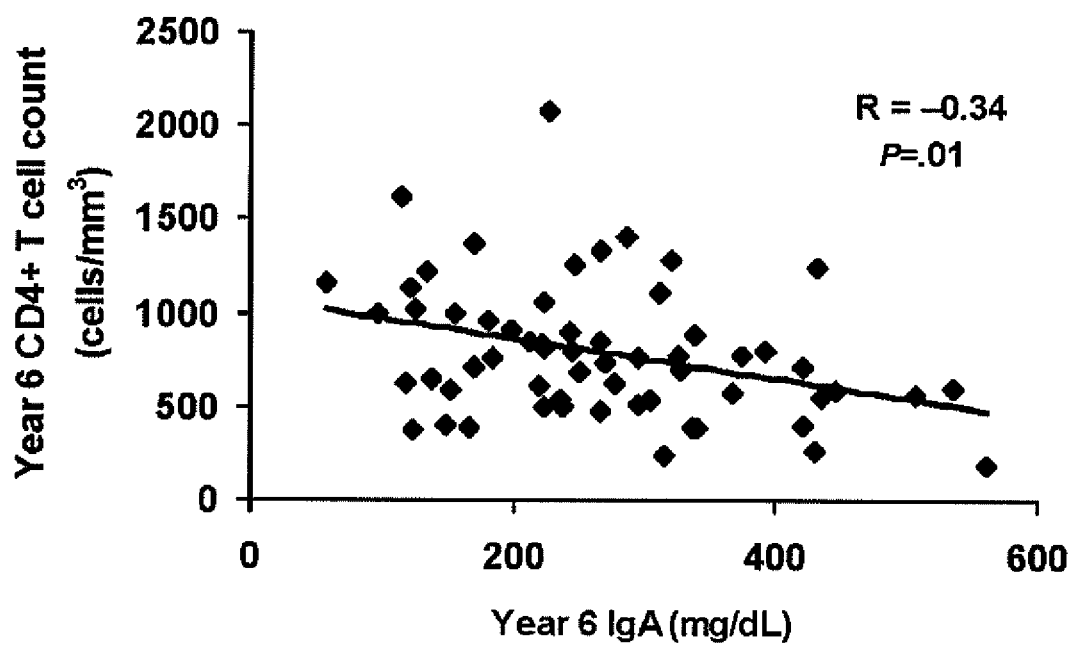

FIG. 25 illustrates one expected consequence of increased microbial translocation is the induction of increased IgA responses due to mucosal antigen exposure. French et al., *J Infect Dis.* 200(8): 1212-1215, 2009 demonstrated that indeed the total level of IgA in HIV patients after 6 years of follow up was inversely correlated with the level of CD4 T-cells in patients undergoing highly active antiretroviral therapy, suggesting that even in patients being treated with the most effective current antiviral therapies, microbial translocation contributes to pathogenesis. However these results also show that total IgA is highly variable between individuals, and does not provide a prognostic marker that can be used in management of individual patients.

Figure 26:
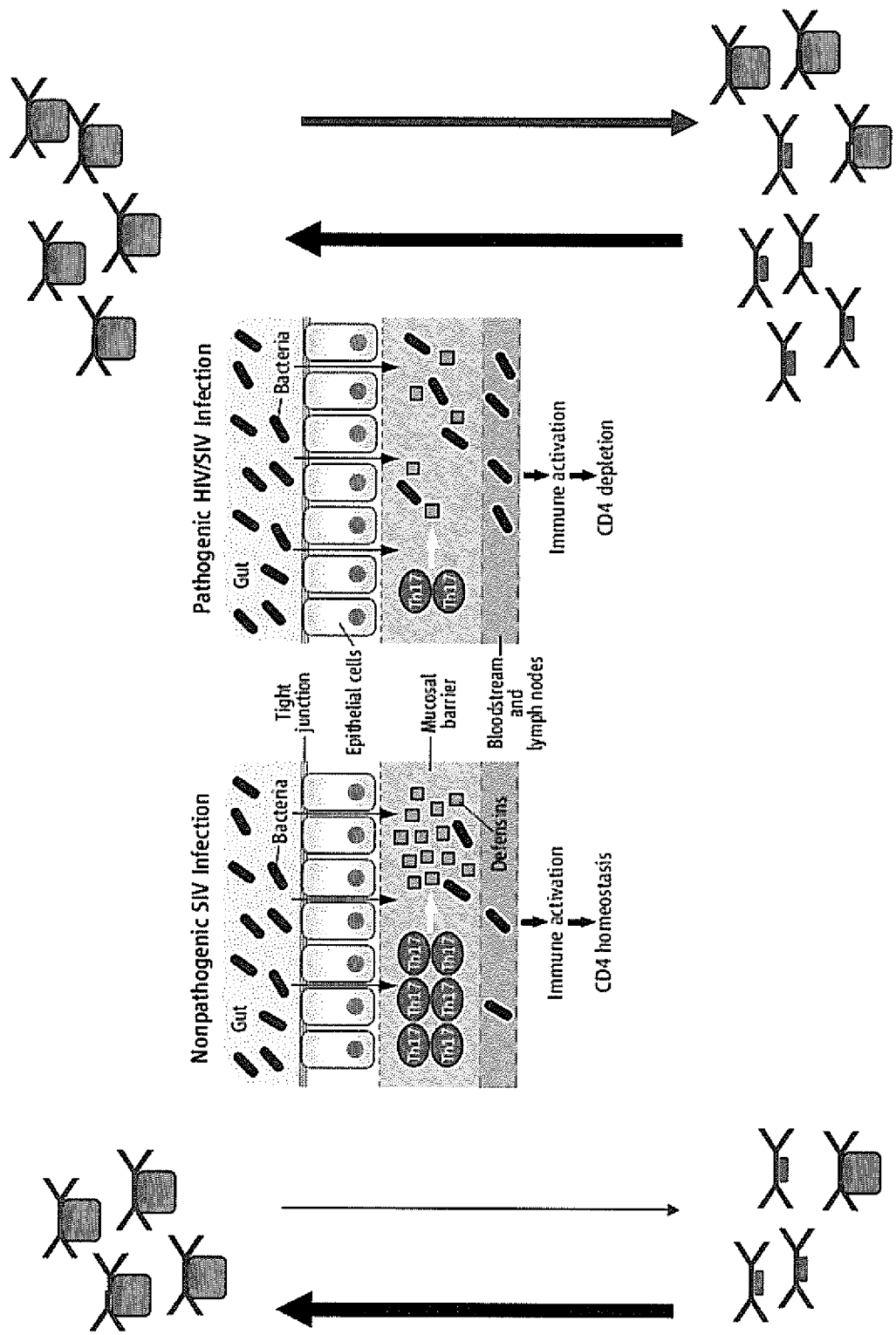

FIG. 26 provides a schematic illustration of the increase in microbial translocation due to gut leakage induced by pathogenic HIV or SIV infection, compared to normal low levels of translocation in nonpathogenic SIV infection, showing the expected effect on dimeric IgA and secretory IgA levels in the plasma compartment. Under normal conditions or nonpathogenic SIV infection, gut barrier integrity is maintained and the level of SIgA in the lumen of the gut reflects the amount of its precursor dIgA in the lamina propria. Only a minimal amount of SIgA is returned to the plasma compartment, either through active transport by M-cells in the gut, or a small amount of gut leakage. The amount of leakage or active transport can be estimated by comparing the serum/plasma concentration of SIgA to that of its precursor dIgA, giving a ratio of SIgA/dIgA. Under conditions of pathogenic HIV or SIV infection, or other physiological challenges that result in gut leakage, the total amount of dIgA is likely to be somewhat elevated and may lead to higher levels of SIgA secretion into the lumen. However a much higher proportion of SIgA will be returned to the plasma compartment due to passive leakage through the compromised gut barrier, resulting in an elevated SIgA/dIgA ratio.

Figure 27:
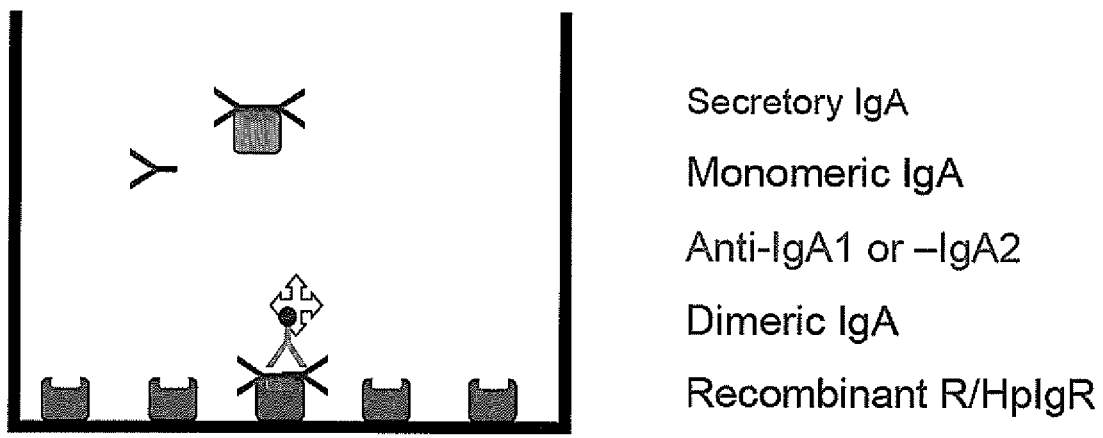

FIG. 27 provides a schematic of one of several typical assays that can be used to measure the relative amount of different IgA forms in order to estimate the SIgA/dIgA ratio. In this example, the amount of dIgA is measured by capture of dIgA using R/HpIgR, and detection using monoclonal antibodies against either IgA1, or IgA2, or against both IgA subclasses. Monomeric IgA does not bind to pIgR; SIgA does bind to R/HpIgR but with lower affinity than dIgA and can be removed by washing with 3.5 M urea if desired. SIgA is measured in the same way but using anti-SC antibody capture instead of R/HpIgR. The SIgA/dIgA ratio is then calculated as a simple ratio of the assay reactivities for SIgA and dIgA.

Figure 28:
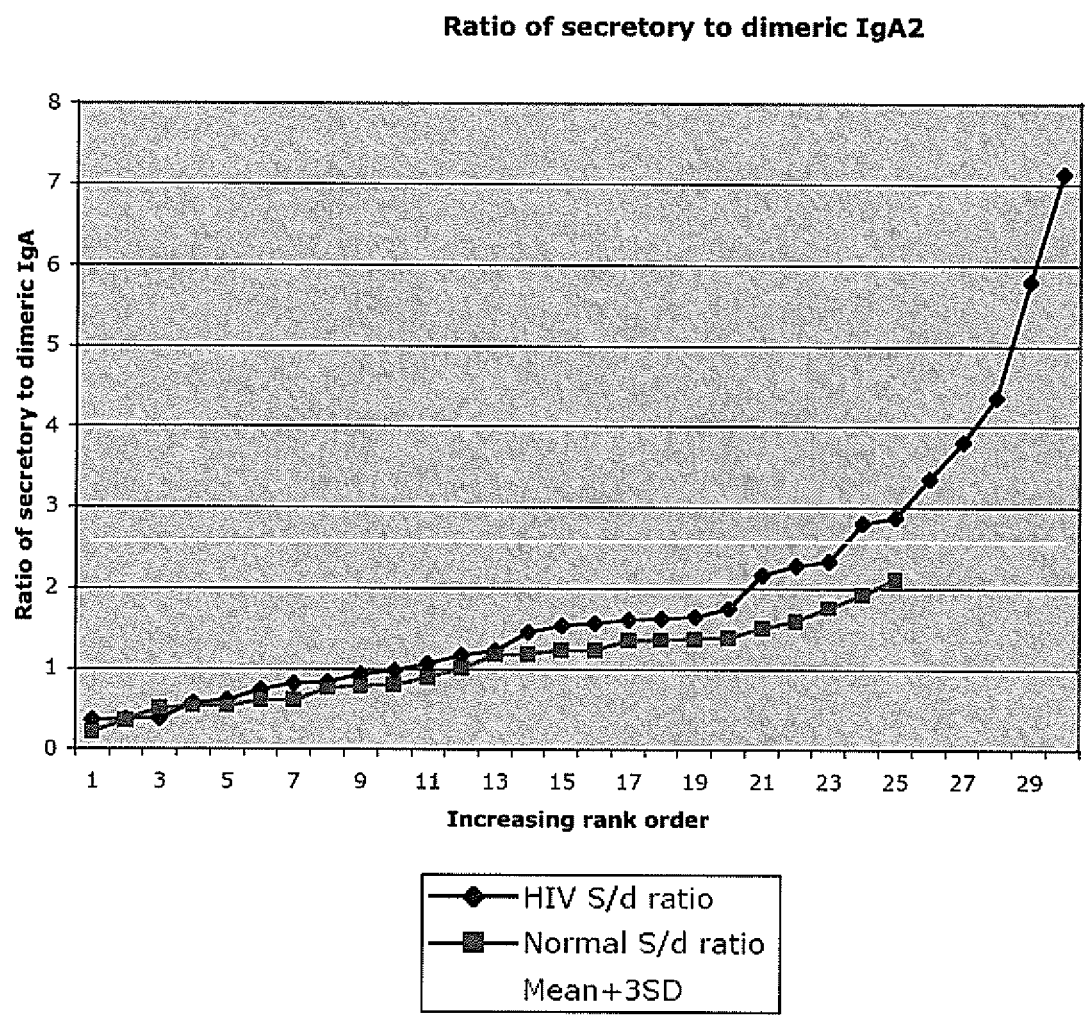

FIG. 28 provides the results of ELISA demonstrating the detection of highly elevated SIgA2/dIgA2 (S/d) ratios in a proportion of HIV-infected patients, compared to the majority of HIV-infected patients and all control subjects (magenta). The assay cutoff for elevated SIgA/dIgA was set as the mean plus 3 standard deviations of the SIgA/dIgA ratio among non-HIV control subjects, and 7/30 HIV-infected subjects showed SIgA/dIgA ratios above this cutoff. Notably, the range of SIgA/dIgA ratios among normal subjects is smaller than the range for SIgA or dIgA alone, because the role of dIgA as the precursor of SIgA provides a normalising effect for each patient.

Figure 29:
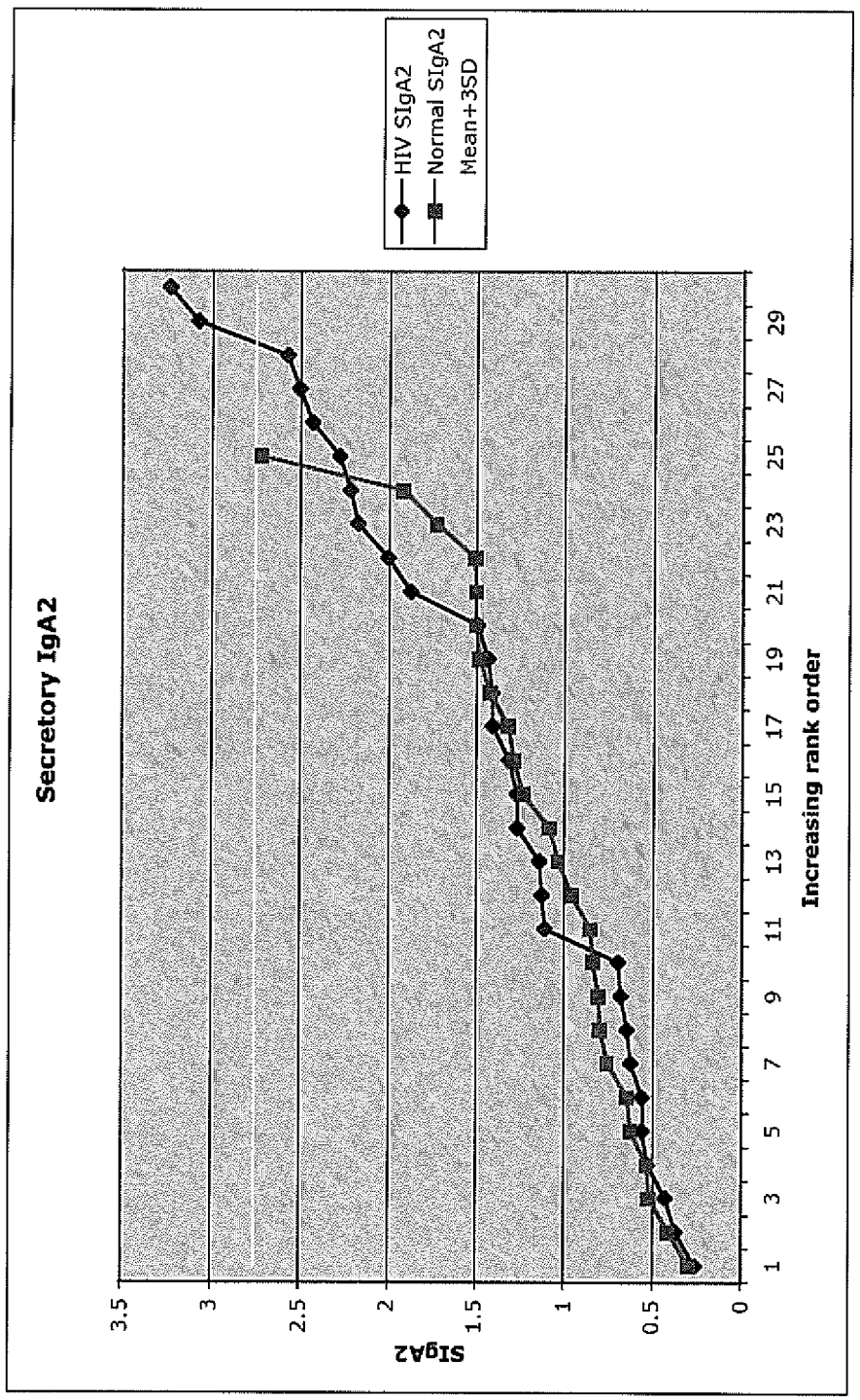

FIG. 29 provides the results of ELISA demonstrating the total amount of SIgA in patient and control sera (arbitrary units). The amount of SIgA2 in normal patients varies over an 11-fold range, but all normal controls fall within a cutoff of the mean plus 3 standard deviations. The amount of SIgA2 in HIV-infected patients varies over a slightly larger range (16-fold), but only 2/30 patients are above the cutoff range. Among the HIV-infected patients, those patients who demonstrated elevated SIgA2/dIgA2 ratios in FIG. 28 are indicated with red markers. It can be seen that these patients with elevated SIgA2/dIgA2 ratios are found throughout much of the normal range of the total SIgA2 signal, and cannot be distinguished from the normal controls on the basis of the total SIgA2 alone. This confirms the utility of using SIgA/dIgA ratios because the role of dIgA as the precursor of SIgA provides a normalising effect for each patient. The R/HpIgR system provides the utility for measuring this ratio.

Figure 30:
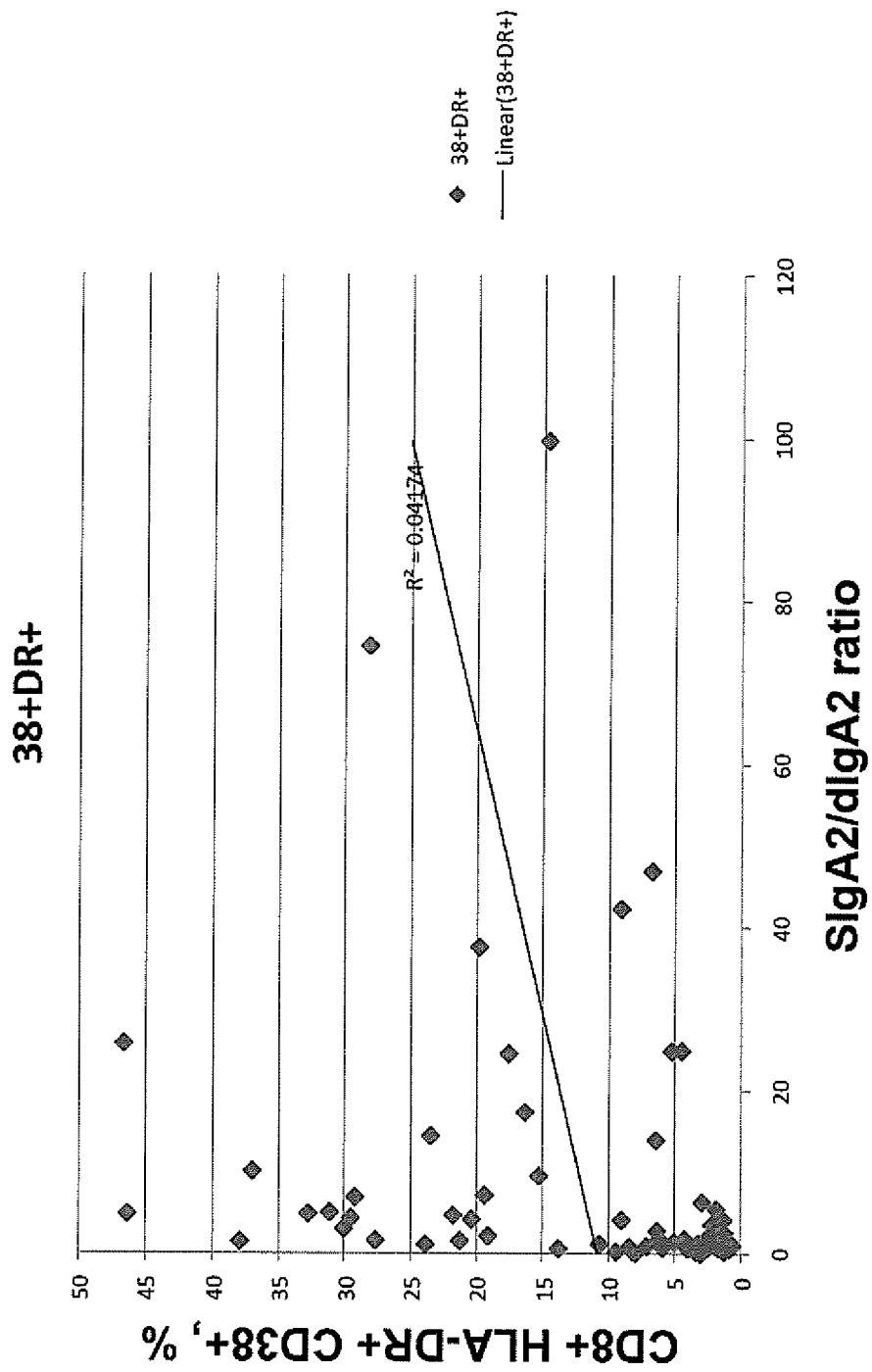

FIG. 30 illustrates the correlation of SIgA2/dIgA2 ratio versus the immune activation marker, CD8+ HLA-DR+ CD38+ T-cells, in a different HIV-infected population to that shown in FIGS. 28 and 29. While the overall correlation is low, it is apparent that patients with SIgA2/dIgA2 ratios of >4 in this experiment have elevated levels of immune activation markers ($p<0.0001$).

Figure 31:
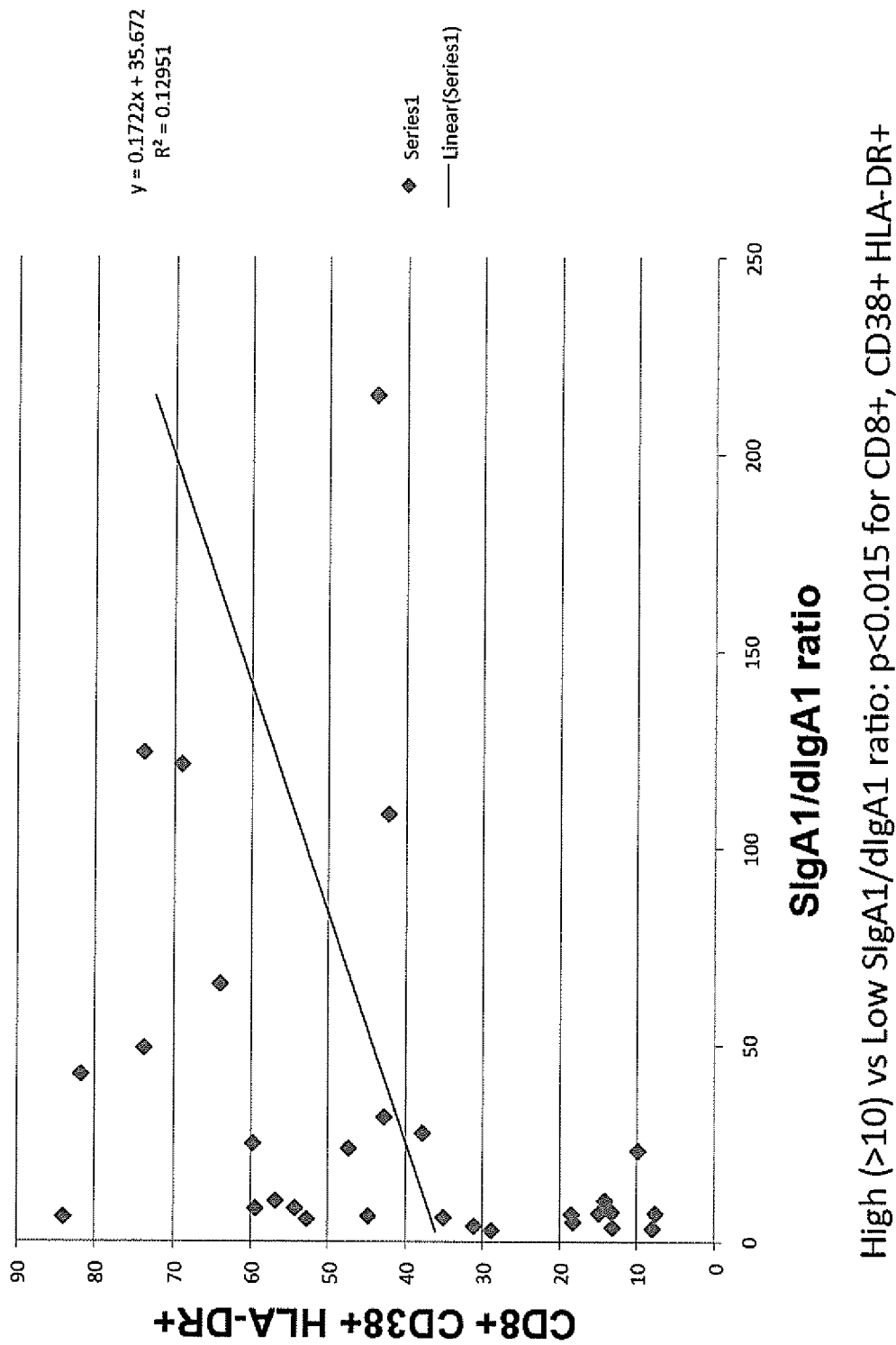

FIG. 31 illustrates the correlation of SIgA1/dIgA1 ratio versus the immune activation marker, CD8+ HLA-DR+ CD38+ T-cells, in the same population as FIG. 30. While the overall correlation is lower again than for IgA2, it is apparent that patients with SIgA1/dIgA1 ratios of >10 in this experiment have elevated levels of immune activation markers ($p<0.015$). The lower correlation for IgA1 and higher cutoff ratio (10 versus 4) for significance highlights the value of specifically measuring IgA2 because of its predominant site of synthesis in the gut, being the tissue in which leakage of SIgA is likely to be clinically relevant marker of gut leakage and immune activation.

Figure 32:
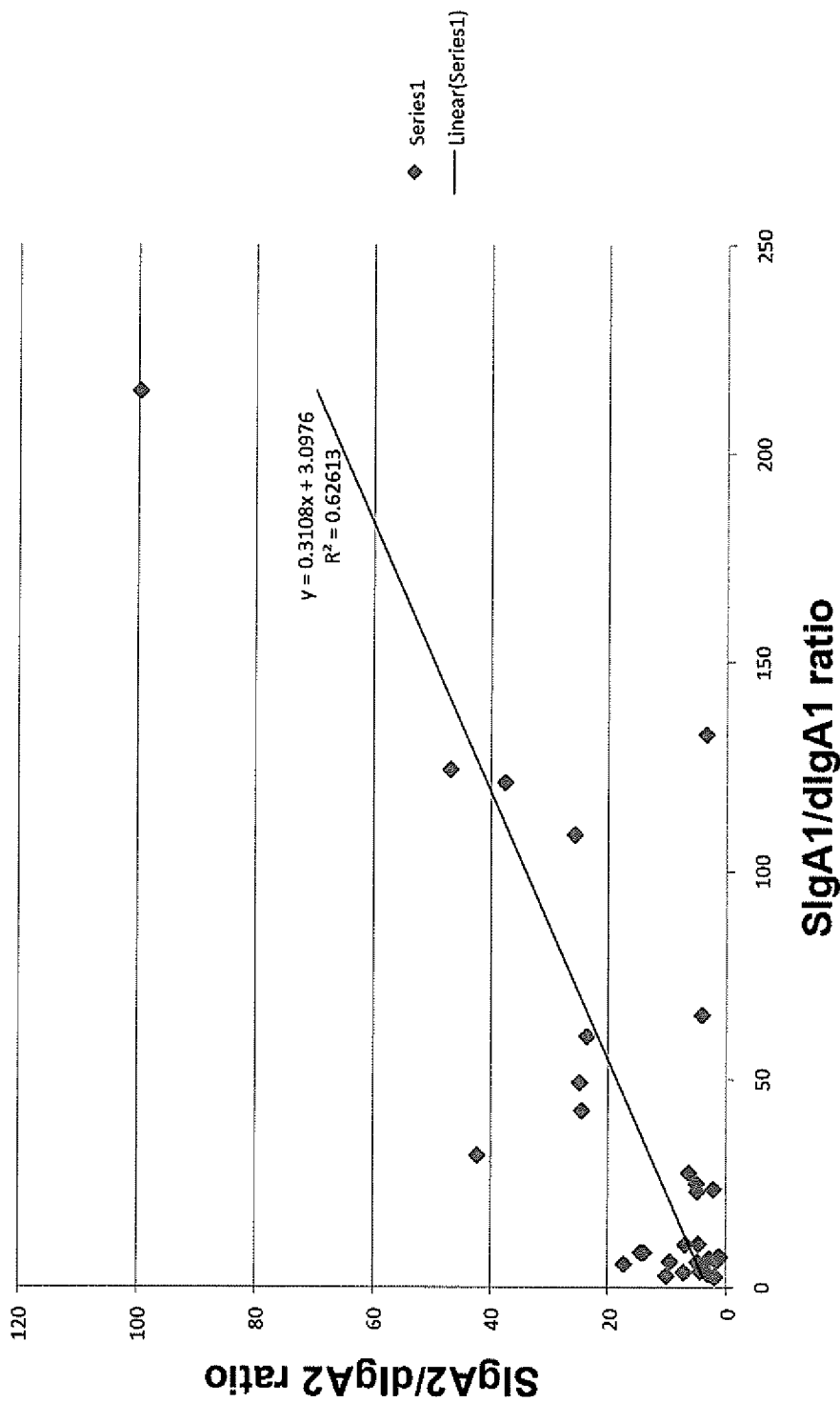

FIG. 32 illustrates the correlation of SIgA1/dIgA1 ratio versus SIgA2/dIgA2 ratio, in the same population as FIGS. 30 and 31. While SIgA1/dIgA1 ratios are significantly correlated with SIgA2/dIgA2, it is notable that there are some patients with highly elevated SIgA1/dIgA1 ratios and relatively low SIgA2/dIgA2 ratios. This suggests that there may be some value in measuring IgA1, or total IgA, in addition to IgA2 in the calculation of SIgA/dIgA ratios as a measure of gut leakage and immune activation.

FIG. 33 provides the nucleotide sequence and amino acid sequence of CHIMERA-CD4 cyto (R/HpIgR-cyto) showing rabbit sequences underlined and human sequences in black, and CD4 cyto sequences in grey.

FIG. 34 provides the nucleotide sequence and amino acid sequence of CHIMERA (R/HpIgR) showing rabbit sequence underlined and human sequence in black.

FIG. 35 provides graphical and tabulated date showing hepatitis C virus specific dIgA detection. In addition to the acute, self-limiting hepatitis A virus and hepatitis E virus which are transmitted from person to person via fecal-oral routes, there are at least three other viruses that cause viral hepatitis which is commonly chronic and leading to severe long-term disease, and where the viruses are considered to be blood-borne, namely hepatitis B, hepatitis C and hepatitis D. In this example, it can be seen that even for a chronic infection such as hepatitis C virus, HCV-specific dIgA is detectable for only a relatively short time after infection, up to around 100 days after the last blood sample that tested negative for HCV, suggesting that HCV-specific dIgA may be a marker of acute infection. While only 4 out of 5 (80%) of HCV patients had detectable HCV-specific dIgA in this assay, it will be evident to those skilled in the art that there are a variety of methods that could be used to increase the sensitivity of this assay for detection of acute-phase HCV, which will be useful in determining the best options for treating patients with antiviral drugs or interferon-containing medications. It will also be evident that since virus-specific dIgA is found in the diverse range of diseases including hepatitis A, hepatitis E, hepatitis C and tuberculosis, it is reasonable to assume that it may be detectable, and of utility in diagnostic and therapeutic protocols, for any other infectious disease.

FIG. 36 provides a graphical representation of data comparing different commercially available antibodies for binding to R/HpIgR or HpIgR. It will be apparent to those skilled in the art that there are many different monoclonal and polyclonal antibodies directed against the pIgR (also known as secretory component or SC) that may be used for the detection of bound pIgR, and thus antigen-specific or total dIgA or IgM, in a variety of assay methods. In this example, it can be seen that several commercially available antibodies can be used for this purpose, whereby serial dilutions of either recombinant expressed chimeric R/HpIgR or recombinant expressed human HpIgR was coated on polystyrene ELISA plates, and detected using serial dilutions of mouse monoclonal or sheep polyclonal antibodies, and detected with appropriate anti-species antibodies. Note that the R/HpIgR is present at higher concentrations, and so there is no titration of the assay signal in this experiment, whereas with the HpIgR which is present at lower concentrations, the titration of antibody reactivity reveals that commercial Abcam monoclonal antibody 17921 is approximately equivalent to sheep polyclonal antibody, while Abcam 17377 and 3924 appear to be less reactive, as does the Nordic Immunology monoclonal against SC. The rabbit antibody is a negative control. These and other antibodies can be selected according to their binding to either free pIgR forms, or pIgR forms already bound to dIgA or pIgM, to fit the purpose needed in detection of R/HpIgR or HpIgR or dIgA-binding variants thereof accordingly.

DESCRIPTION OF PARTICULAR EMBODIMENTS

Throughout this specification and the claims which follow, unless the context requires otherwise, the word "comprise", and variations such as "comprises" and "comprising", will be understood to imply the inclusion of a stated integer or element or method step or group of integers or elements or method steps but not the exclusion of any other integer or element or method step or group of integers or elements or method steps.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise.

Nucleotide and amino acid sequences are referred to by a sequence identifier number (SEQ ID NO:). The SEQ ID NOs: correspond numerically to the sequence identifiers <400>1 (SEQ ID NO: 1), <400>2 (SEQ ID NO:2), etc. A summary of sequence identifiers is provided in Table 1. A sequence listing is provided at the end of the specification.

As described herein, the present disclosure provides an antibody capture process comprising determining the level or presence of dimeric or polymeric IgA (dIgA) in a biological sample. The process of the present invention may be practised by detecting only the level or presence of dIgA, or it may be practised in combination with protocols to determine the level or presence of one or more further antibody forms (e.g., monomeric, dimeric, polymeric or pentameric complexes), classes (isotypes) or subclasses (e.g., dIgA1, dIgA2, SIgA2, etc.). In some embodiments, the process is practised using specific antigens that bind to dIgA molecules of interest. In other embodiments, the process may be practised to identify antigens of interest which engender dIgA responses in a subject that may be detected in a sample from a subject. In some embodiments, the process enables the development inter alia of diagnostic assays and therapeutic protocols that are useful for assessing secretory IgA responses at mucosal surfaces and associated tissues such as gut-associated lymphoid tissue (GALT).

The present process is predicated in part on the ability to detect dIgA or dIgA and IgM with high sensitivity and specificity in binding assays using a recombinant polymeric Ig receptor (pIgR). The present process employs recombinant pIgR or recombinant variants of pIgR that bind dIgA and IgM, as well as recombinant pIgR or variants of pIgR that preferentially bind dIgA and substantially fail to bind IgM.

Accordingly, the present specification provides an antibody-capture process comprising detecting or capturing a precursor to secretory dIgA (SIgA), namely dIgA. In some embodiments, the process comprises step (i) contacting a biological sample from a subject with recombinant polymeric immunoglobulin (Ig) receptor (pIgR) or an dIgA-binding variant thereof, wherein the pIgR or variant binds dIgA and IgM; or wherein the pIgR or variant binds dIgA and substantially fails to bind IgM, and wherein the pIgR substantially does not bind monomeric IgA, and step (ii) determining the level or presence of dIgA that has bound to pIgR. In some embodiments, step (ii) comprises detecting a complex between dIgA and pIgR or a complex between bound dIgA and an antigen.

Reference herein to "biological sample" includes a sample obtained from a subject comprising antibodies. The term also includes sample comprising cells expressing dIgA e.g., hybridoma cells, and samples comprising recombinant dIgA expressed from cell lines cultured in vitro. Biological samples from subjects include blood and serum samples, other bodily liquids, biopsy etc. Blood and serum samples are preferred. Reference to an "antigen" includes a protein or infection agent or part of a protein or part of an infection agent, as known in the art. Reference to R/HpIgR includes chimeric forms comprising a immunoglobulin domain from a rabbit pIgA sequence or similar dIgA-binding variant sequences derived from rat or mouse or functional (dIgA-binding) variants thereof. Thus R includes rabbit, or mouse, or rat-derived sequences.

Determining the presence or level of dIgA or pIgR or a complex between dIgA and recombinant pIgR or a complex between recombinant dIgA and an antigen may be by any convenient protocol.

A diverse range of assays are used in research, analysis, development and clinically to detect analytes of interest. Immunoassays are a particularly useful form of assay that exploits the specificity, strength and diversity of antibody-antigen type or protein-protein reactions to analyse samples and detect specific components therein. A wide range of immunoassay techniques are available, such as those described in Wild D. "*The Immunoassay Handbook*" Nature Publishing Group, 2001.

Methods of detecting antibody complexes, antigens or antibody-ligand complexes are well known in the art. For example, the enzyme-linked immunosorbent assay (ELISA) and radioimmunoassay (RIA) are routinely used in laboratories. These methods generally require some level of skill in laboratory techniques. A variety of methods have also been developed which require little skill and are rapid to perform, and which are therefore suitable for the detection of antibody to specific antigens at the point of care or analysis. In particular, immunochromatographic or dipstick enzyme-linked immunosorbent kits have been developed to assay for a number of infections agents.

Immunochromatographic devices are expressly contemplated comprising dIgA-binding reagents such as recombinant pIgR and further comprising antigens of interest identified as described herein as binding dIgA from infected subjects or subjects exhibiting mucosal immune activation.

Kits or immunochromatographic devices comprise, for example, reverse-flow or lateral-flow formats.

In an illustrative embodiment, a kit for assessing immune status in a biological sample from a subject is provided which employs one or more antigens of interest recognised by dIgA from subjects with active infections or conditions associated with mucosal immune activation, and employs a pIgR molecule or dIgA-binding variant thereof as a dIgA-binding reagent. In a preferred embodiment, the antigen is not a TB antigen.

In some embodiments, the kit comprises:
a) an immunographic device comprising a porous membrane operably connected to a sample portion, a test portion, and optionally a control portion; and further comprising a sucker portion, portion comprising a pIgR molecule or dIgA-binding variant thereof a portion comprising an antigen or agent of interest and optionally a conjugate portion; and
b) instructions for using the immunographic device to detect the presence of antigen specific dIgA antibody in the sample.

In one embodiment, the pIgR or dIgA-binding variant thereof is HpIgR or R/HpIgR or a dIgA binding variant thereof.

The subject assays may employ a wide range of suitable detection markers known in the art. In some embodiments, the detection marker may be detected using detectable characteristics of the detection marker and a wide range of detection protocols using detectable markers are well known to those of ordinary skill in the art. In some embodiments, the detection marker is directly or indirectly bound or otherwise associated with an antigen or infectious agent of interest. In other embodiments, the dIgA binding agent, such as pIgA comprises or is designed to interact with a detection marker. In some embodiments, the detection marker is connected the antigen or dIgA binding agent using binding partners known in the art such as without limitation biotin:avidin or anti-biotin antibody:biotin.

Polymeric immunoglobulin receptor (pIgR) is encoded by the PIGR gene and is expressed in mucosal epithelial cells where it facilitates uptake of dIgA and secretion of SIgA. pIgR has five immunoglobulin-like domains which bind to dIgA including to the J-chain thereof. pIgR also binds to pentameric IgM.

As determined herein it is possible to detect both dIgA and IgM with high sensitivity and specificity using recombinant human polymeric Ig receptor and parts and variants thereof (see FIG. 3). In one particular non-limiting embodiment it is shown herein that dIgA can be selectively detected using a recombinant form of the polymeric Ig receptor having at least domain 1 derived from the rabbit pIgR, for example, a chimera of rabbit (domain 1) and human (domain 2-5) pIgRs, or with all domains from rabbit pIgR. In some embodiments, the recombinant pIgR described herein are designed to bind preferentially to dIgA (plus or minus IgM), and can be used either to capture dIgA (IgM) specifically to a solid phase for reaction with an antigen of interest, in which case the pIgR does not need to have an associated detection reagent, or alternatively to detect the presence of dIgA (±IgM) bound to an antigen of interest immobilized on a solid phase, in which case the pIgR may be conveniently detected using antibodies or other reagents directed against the pIgR itself, or against epitope tags or other sites introduced into the recombinant pIgR using methods well known in the art. A further advantage of pIgR is that it shows very low background reactivity in assays, unlike typical antibody-based detection reagents.

Roe et al., *J Immunol* 162: 6046-52, 1999 describe a chimeric pIgR comprising immunoglobulin-like domain 1 (D1) derived from rabbit, and D2-5 derived from human pIgR which has preferential binding to dIgA over IgM. However, they do not disclose or suggest the use of this form or any other pIgR variant for detection or binding only of dIgA for diagnostic purposes or the advantages of the recombinant pIgA or dIgA binding variants disclosed herein. The substitution of human for rabbit (or mouse or rat) D1 provides preferential binding of dIgA, but it would be expected that substitution of any one or more of D2-D5 may also be substituted with the rabbit sequence to give a molecule that preferentially binds to dIgA and these variants are also encompassed. Accordingly, in some embodiments, any one or more of D1, D2, D3, D4 or D5 is substituted with rabbit, mouse or rat homologs.

In some embodiments, the recombinant pIgR lacks a transmembrane domain (ΔTM). In other embodiments, the recombinant pIgR lacks a cytoplasmic domain. In some embodiments, the recombinant pIgR lacks a TM domain and a cytoplasmic domain (ΔCYT). In some embodiments, recombinant pIgR comprises a substitution in the cytoplasmic domain and provides a CD4 cytoplasmic domain. Various forms of recombinant pIgR are contemplated and illustrative examples are illustrated in FIGS. 4 to 7, further described in the figure legends. The ability to design and test recombinant pIgR having a desired level of specific dIgA is illustrated in FIG. 8 and described in the legend to FIG. 8.

Phillips-Quagliata et al., *J Immunol* 165: 2544-2555, 2000 indicate that both rat and mouse bind predominantly dIgA, but that for mouse there is a form expressed on B-cells that has only a single amino acid change but binds both IgM and dIgA—to quote from page 2552:

"Although human pIgR and the T560 mouse pIgR bind both pIgA and IgM, rabbit (44) and rat (47) hepatocyte pIgR bind only pIgA well and do not translocate IgM into bile. Because mouse liver similarly translocates pIgA but not IgM into bile (48, 49), it is generally assumed that mouse hepatocyte pIgR resembles rat and rabbit pIgR and binds IgM poorly or not at all. If this is true, then the difference between the mouse hepatocyte and the T560 pIgR that makes the latter behave more like human pIgR must be explained. Given that the amino acid sequences of the mouse hepatocyte and T560 B cell pIgRs are the same except for the Val to Ala change in domain 2, the difference most likely reflects differential folding or glycosylation of the pIgR, probably the latter. It is easy to imagine that a bulky carbohydrate on hepatocyte-derived pIgR could interfere with IgM but not with IgA binding. Furthermore, it has already been shown that deglycosylation of human SC allows it to inhibit binding of biotinylated native SC to pIgA with 10 times greater efficiency than native SC itself (50), suggesting that some of the carbohydrate moieties on human pIgR may actually impede binding even of pIgA."

Accordingly, in some embodiments, a deglycosylated variant of the recombinant pIgR including R/HpIgR is used to improve binding affinity to dIgA. In some embodiments, this may be achieved by expressing the pIgR in a glycan-deficient cell line known in the art such as, for example, a glycan deficient CHO cell line.

In plural embodiments, recombinant pIgR comprises a deletion in the transmembrane domain (ΔTM) to allow for convenient secretion of the recombinant protein and ease of use as a diagnostic/prognostic/screening agent.

In some embodiments, the recombinant pIgR comprises a heterologous detection domain.

Multiple detection domains are known in the art and are encompassed.

In some embodiments, the recombinant pIgR comprises a heterologous binding domain.

Multiple binding domains are known in the art and are encompassed.

In other embodiments, the recombinant pIgR is bound to a solid support. Solid supports include plates, wells, beads, agarose particles, nitrocellulose strips, etc.

In some embodiments, recombinant pIgR is produced in glycan deficient cells such as glycan deficient CHO cells to enhance preferential binding to dIgA over IgM.

In some embodiments, the recombinant pIgR is derived from a primate such as human pIgR and comprises at least one immunoglobulin-like domain derived from a non-primate such as rabbit, mouse, rat.

In some embodiments, the recombinant pIgR comprises an amino acid sequence set out in SEQ ID NO:2, or SEQ ID NO: 4, or SEQ ID NO: 6, or SEQ ID NO: 12, or SEQ ID NO: 14, or SEQ ID NO: 16, or an dIgA-binding part thereof or and a dIgA binding variant thereof. Illustrative variants comprise at least 70% amino acid sequence identity to one of SEQ ID NO: 2, 4, 6, 12, 14 or 16 or deletion variants thereof lacking a cytoplasmic domain.

Variants include deletion, substitution and insertional variants. Illustrated herein are human derived pIgR varied by one or more immunoglobulin domains (D). Variants include "parts" which includes fragments comprising from about 50%, 60%, 70%, 80%, 85%, 90%, 95% of the reference sequence. Substitution for an equivalent domain from a lower mammal such as a rat, mouse or rabbit domain.

"Variants" of the recited amino acid sequences are also contemplated. Variant molecules are designed to retain the dIgA binding functional activity of the pre-modified recombinant pIgR or to exhibit enhanced activity. Polypeptide variants according to the invention can be identified either rationally, or via established methods of mutagenesis (see, for example, Watson, J. D. et al., "*Molecular Biology of the Gene*", Fourth Edition, Benjamin/Cummings, Menlo Park, California, 1987). Random mutagenesis approaches require no a priori information about the sequence that is to be mutated. This approach has the advantage that it assesses the desirability of a particular mutant based on its function, and thus does not require an understanding of how or why the resultant mutant protein has adopted a particular conformation. Indeed, the random mutation of target gene sequences has been one approach used to obtain mutant proteins having desired characteristics (Leatherbarrow R., *J. Prot. Eng.*, 1:7-16, 1986; Knowles J. R., *Science*, 236:1252-1258, 1987; Shaw W. V., *Biochem. J.*, 246:1-17, 1987; Gerit J. A., *Chem. Rev.*, 87:1079-1105, 1987). Alternatively, where a particular sequence alteration is desired, methods of site-directed mutagenesis can be employed. Thus, such methods may be used to selectively alter only those amino acids of the protein that are believed to be important (Craik C. S., *Science*, 228:291-297, 1985; Cronin et al., *Biochem.*, 27: 4572-4579, 1988; Wilks et al., *Science*, 242:1541-1544, 1988). Illustrative amino acids affect glycosylation of the recombinant pIgR. Polypeptides, resulting from rational or established methods of mutagenesis or from combinatorial chemistries, may comprise conservative amino acid substitutions. It is well understood in the art that some amino acids may be changed to others with broadly similar properties without changing the nature of the activity of the polypeptide (conservative substitutions, see Table 3).

Variant pIgR polypeptides comprises at least 50% sequence identity to herein amino acid sequence at least over the immunoglobulin-like domain region.

The terms and "sequence identity" as used herein refer to the extent that sequences are identical or functionally or structurally similar on an amino acid-by-amino acid basis over a window of comparison. Thus, a "percentage of sequence identity", for example, is calculated by comparing two optimally aligned sequences over the window of comparison, determining the number of positions at which the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity which counts as identical, substitutions involving conservative substitutions.

Preferably, the percentage similarity between a particular sequence and a reference sequence (nucleotide or amino acid) is at least about 60% or at least about 70% or at least about 80% or at least about 90% or at least about 95% or above such as at least about 96%, 97%, 98%, 99% or greater. Percentage similarities or identities between 60% and 100% are also contemplated such as 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In another embodiment there is provided recombinant pIgR encoded by the sequence of nucleotides set out in SEQ ID NO:1, SEQ ID NO:3, SEQ ID NO:5, SEQ ID NO:11, SEQ ID NO:13 or SEQ ID NO:15, or a dIgA-binding and optionally IgM-non binding variant thereof having at least 60% nucleotide sequence identity thereto or at least 60% nucleotide sequence identity to deletion variants thereof lacking a cytoplasmic domain.

In some convenient embodiments, the recombinant pIgR is a human recombinant pIgR variant comprising at least one immunoglobulin-like domain derived from a rabbit.

In some embodiments, (human) pIgR that binds pIgM and dIgA is employed. In some embodiments, IgG and/or IgM, are depleted using known protocols, and, if IgM is depleted then the human pIgR is selective for dIgA among what is left in the sample. In some embodiments, for diagnosis of many infections it may be preferable to detect both dIgA and pIgM—certainly IgA plus IgM is reported in the literature for hepatitis E and as illustrated herein there are some samples for hepatitis A or hepatitis E in which either IgM or dIgA are much stronger, suggesting that their combined detection is useful. While this could be achieved using a mixture, for example, of anti-IgM and the R/HpIgR, it may more conveniently be achieved with a mixture of HpIgR and R/HpIgR (so that the IgM does not outcompete the dIgA), or with HpIgR alone if it is present in excess over the sum of IgM and dIgA. It is proposed to be preferable to use two variations of the same reagent rather than one antibody plus a recombinant protein. In particular, pIgR is more thermally stable than antibody which is an advantage for test production.

The use of recombinant pIgR is also highly advantageous not least because the reagent displays low background (at least 50% less background compared to antibody based reagents) in binding assays unlike most antibody based binding agents. In addition, recombinant pIgR displays high thermal stability. For example, lyophilised recombinant pIgR retained 50% activity at 60° C. and 100% activity at 45° C. after three weeks prior to reconstitution, which compares favourably to the rapid loss of activity for dried anti-IgM antibody under the same conditions.

In embodiments, where substantially only dIgA (or IgM) is to be detected, recombinant human pIgR or dIgA and IgM binding variants may be employed as the binding reagent, but specifically detection of bound dIgA (either dIgA1 or dIgA2) is achieved using anti-IgA1/IgA2, in this embodiment, the presence of IgM is not a problem.

In some embodiments the process is for use in a method of assessing conditions or infections of a mucosal surface or associated tissues, or immunity thereto. Illustrative applications to specific antigens are described in the Figures and Figure legends for FIGS. 10 to 22 inclusive and these general protocols are expressly contemplated herein as well as routine variations thereto.

Illustrative mucosal surfaces include the upper and lower respiratory tracts, the gut and gut-associated lymphoid tissue, the genital tract and the liver.

Illustrative infections include without limitation those mediated by bacteria, viruses, parasites and other infectious organisms. In certain embodiments, infectious agents include, HIV, leprosy, syphilis, hepatitis (e.g., HEV, HAV, HCV) dengue virus, measles, rubella etc.

Illustrative conditions include diseases of organs such as the respiratory tract, lungs, gut, genital tract and liver. Gut conditions include ulcerative colitis, Crohn's disease, IBS, leaky gut syndrome etc.

Reference to "subject" includes humans and a wide range of mammalian or other animals including wild and domesticated animals, pets, pests and potential vehicles for emerging infectious diseases. In relation to subjects, these may have an infection, they may have had exposure to infection or they have had exposure to an infectious agent.

In one embodiment, FIG. 10 is a schematic of one preferred experimental approach for detecting the presence of antigen-specific dIgA in a sample such as human serum or plasma. Recombinant R/HpIgR-cyto is immobilised on the ELISA plate, and incubated with serum or other samples. Dimeric IgA is captured on the solid phase, and after washing to remove other sample components (such as IgA and IgG that are not captured, left), the presence of antigen-specific dIgA is detected by sequential addition of antigen that is, for example, either biotinylated, or reacted with a biotinylated monoclonal antibody against the antigen, and streptavidin-HRP. In this way, any antigen that is immobilised by reaction with antigen-specific dIgA will give a signal through the biotin-streptavidin interaction or an equivalent reagent.

In one embodiment, FIG. 11 is a schematic of one preferred experimental approach for detecting the presence of hepatitis A virus-specific dIgA in serum (right), compared to detection of HAV-specific IgM using the standard method of anti-IgM capture (left).

In one embodiment, FIG. 16 is a schematic of a second preferred method for detection of antigen-specific dIgA (or IgM), in which antigen is coated directly onto the ELISA plate (in this case, hepatitis E virus (HEV) antigen). Serum samples are applied to the plate and antigen-specific antibodies, including IgM and dIgA, bind to the antigens and are then detected with either anti-IgM HRP, or R/HpIgR and anti-human SC HRP. After final washing, signal is generated with TMB substrate or equivalent reagent.

In another embodiment, FIG. 23 provides a model outlining the pathogenic consequences of acute human immunodeficiency (HIV) infection, which leads to rapid CD4 depletion in the gut as well as the periphery, with a subsequent reduction in gut barrier function, increased leakage of gut contents and microbial translocation, leading to increased immune activation which drives pathogenesis and further reduction of CD4 T-cell levels (Brenchley et al, *Nat Med* 12: 1365-1371, 2006). There is an unmet need for simple, standardised assays that can detect one or more of these steps in the pathogenesis pathway so that appropriate interventions can be provided to patients, with only CD4 testing having been integrated into the standard of care for HIV-infected patients. Detection of CD4 depletion in the gut requires endoscopy; detection of decreased gut barrier function requires complicated sugar challenge studies or other methods; detection of gut leakage and microbial translocation can be achieved using markers such as bacterial LPS or 16sRNA in serum but results are highly variable due in part to the wide variation in gut microbiota between individuals; immune activation requires complex Flow cytometry protocols that are difficult to standardise across instruments/operators.

FIG. 24 provides a schematic illustration of the increase in microbial translocation due to gut leakage induced by pathogenic HIV or SIV infection, compared to normal low levels of translocation in nonpathogenic SIV infection.

FIG. 25 illustrates that one expected consequence of increased microbial translocation is the induction of increased IgA responses due to mucosal antigen exposure. M. French et al Journal of Infectious Diseases 200; 2009 demonstrated that indeed the total level of IgA in HIV patients after 6 years of follow up was inversely correlated with the level of CD4 T-cells in patients undergoing highly active antiretroviral therapy, suggesting that even in patients being treated with the most effective current antiviral therapies, microbial translocation contributes to pathogenesis. However these results also show that total IgA is highly variable between individuals, and does not provide a prognostic marker that can be used in management of individual patients.

FIG. 26 provides a schematic of the increase in microbial translocation due to gut leakage induced by pathogenic HIV or SIV infection, compared to normal low levels of translocation in nonpathogenic SIV infection, showing the expected effect on dimeric IgA and secretory IgA levels in the plasma compartment. Under normal conditions or non-pathogenic SIV infection, gut barrier integrity is maintained and the level of SIgA in the lumen of the gut reflects the amount of its precursor dIgA in the lamina propria. Only a minimal amount of SIgA is returned to the plasma compartment, either through active transport by M-cells in the gut, or a small amount of gut leakage. The amount of leakage or active transport can be estimated by comparing the serum/plasma concentration of SIgA to that of its precursor dIgA, giving a ratio of SIgA/dIgA. Under conditions of pathogenic HIV or SIV infection, or other physiological challenges that result in gut leakage, the total amount of dIgA is likely to be somewhat elevated and may lead to higher levels of SIgA secretion into the lumen. However a much higher proportion of SIgA will be returned to the plasma compartment due to passive leakage through the compromised gut barrier, resulting in an elevated SIgA/dIgA ratio.

In another embodiment, the present specification provides a process for assessing gut wall integrity. In some embodiments, and as discussed herein, this assessment provides a prognostic marker for HIV infected patients. In some embodiments, the process comprises determining the relative levels or a ratio of SIgA and dIgA in a sample from a human subject. In some embodiments, the process comprises the step of (i) contacting a biological sample with recombinant polymeric immunoglobulin (Ig) receptor (pIgR) or an dIgA-binding variant thereof, wherein the pIgR or variant binds dIgA and IgM; or wherein the pIgR or variant binds dIgA and substantially fails to bind IgM, and wherein the pIgR substantially does not bind monomeric IgA or secretory IgA and step (ii) determining the level or presence of dIgA that has bound to pIgR. In some embodiments, step (ii) comprises detecting a complex between dIgA and pIgR or a complex between bound dIgA and an antigen essentially as described herein. In another expression of this embodiment, the specification contemplates a process of determining the dIgA/SIgA ratio for use in assessing HIV infected subjects.

Secretory IgA (SIgA) is normally found in only trace amounts in plasma, but in patients with compromised gut barrier integrity, it is proposed herein that a larger proportion of SIgA will leak across the gut barrier and enter the plasma. The normal concentration of SIgA will differ between individual patients, because patients have widely varying levels of the SIgA precursor, dIgA. It is therefore useful to simultaneously measure the concentration of both dIgA and SIgA, with the ratio of SIgA to dIgA in the individual patient providing a measure of gut integrity/leakage.

FIG. 27 provides a schematic of one of several typical assays that can be used to measure the relative amount of different IgA forms in order to estimate the SIgA/dIgA ratio. In this example, the amount of dIgA is measured by capture of dIgA using R/HpIgR, and detection using monoclonal antibodies against either IgA1, or IgA2, or against both IgA subclasses. Monomeric IgA does not bind to pIgR; SIgA does bind to R/HpIgR but with lower affinity than dIgA and can be removed by washing with 3.5 M urea if desired. SIgA is measured in the same way but using anti-SC antibody capture instead of R/HpIgR. The SIgA/dIgA ratio is then calculated as a simple ratio of the assay reactivities for SIgA and dIgA.

As shown in the Examples, a proportion of patients infected with HIV exhibit an elevated level of SIgA compared to dIgA in patient plasma, consistent with elevated immune activation markers in these patients. In further embodiments, gut leakage can be determined by examining the individual IgA isotypes, because IgA2 (dIgA2, SIgA2) represents around 50% of IgA produced in the gut mucosa, but only around 10% of IgA in other tissues, and thus the ratio of SIgA2 to dIgA2 is likely to provide a very sensitive measurement of gut leakage in an individual patient.

Accordingly, in some embodiments, the process comprises measuring the levels of SIgA2 and dIgA2 and determining the ratio of SIgA2 to dIgA2 wherein the ratio relative to a control is indicative of the presence or absence or degree of gut leakage. In some embodiments, this ratio provides marker for HIV infected patients thereby potentially facilitating improved management of HIV infection in a subject. These assays are simple and have potential for high throughput as potential for incorporation into quantitative point of care devices.

Because the reaction between pIgR and dIgA is highly conserved across not only mammals but all vertebrate species, it is proposed that this process will have utility for detection of dIgA, and IgM when desirable, in a wide variety of species, providing a convenient and universal reagent for detection of immune activation or dIgA and/or IgM responses in species such as bats and other wild or domesticated animals for which there may be no available anti-immunoglobulin reagents. This will be useful in diagnosis of diseases of agricultural interest in domesticated animals, and for the diagnosis of disease and detection of host reservoir species for emerging infectious diseases.

The present invention enables the use of the specific interaction between the recombinant expressed forms of pIgR and dIgA (plus or minus IgM), allowing pIgR to be used for specific binding or detection of dIgA (plus or minus IgM) to solid surfaces or other assay components as desired.

In an embodiment, the herein described process and/or recombinant pIgR or variants thereof as described herein are sub-licensed for use in antigen screening or antibody selection and purification.

Treatment protocols are contemplated based upon the results of diagnosis or prognosis testing as described herein.

In some embodiments, the process further comprises: (a) generating data using a process as described herein; (b) transforming the data into computer-readable form; and (c) operating a computer to execute an algorithm, wherein the algorithm determines closeness-of-fit between the computer-readable data and data indicating a diagnosis of a disease or condition. In some embodiments, the algorithm comprises an artificial intelligence program, such as a fuzzy logic, cluster analysis or neural network. The subject methods may also be used in a personalized or a population medicine approach in the management of pathology platforms.

The present disclosure provides a computer program and hardware for diagnosis in a subject once off, over time or in response to treatment or other affectors. Values are assigned to complex levels which are stored in a machine readable storage medium. A computer program product is one able to convert such values to code and store the code in a computer readable medium and optionally capable of assessing the relationship between the stored data and incoming data and optionally a knowledge database to assess a potential TB status and/or pneumonia.

The present specification therefore provides a web-based system where data on levels of complex are provided by a client server to a central processor which analyses and compares to a control and optionally considers other information such as patient age, sex, weight and other medical conditions and then provides a diagnostic report.

The assay may, therefore, be in the form of a kit or computer-based system which comprises the reagents necessary to form and detect the herein described antibody complexes and the computer hardware and/or software including an algorithm to facilitate determination and transmission of reports to a clinician.

The present invention contemplates a method of allowing a user to determine the status of a subject with respect to TB, the method including:
(a) receiving data from the conduct of the process as herein described from the user via a communications network;
(b) processing the subject data via multivariate analysis to provide a diagnostic index value;
(c) determining the status of the subject in accordance with the index value in comparison with predetermined values; and
(d) transferring an indication of the status of the subject to the user via the communications network.

Conveniently, the method generally further includes:
(a) having the user determine the data using a remote end station; and
(b) transferring the data from the end station to the base station via the communications network.

As used herein, the term "binds specifically," and the like when referring to an antigen-binding molecule refers to a binding reaction which is determinative of the presence of an antigen in the presence of a heterogeneous population of proteins and other biologics. Thus, under designated immunoassay conditions, the specified antigen-binding molecules bind to a particular antigen and do not bind in a significant amount to other proteins or antigens present in the sample. Specific binding to an antigen under such conditions may require an antigen-binding molecule that is selected for its specificity for a particular antigen. For example, antigen-binding molecules can be raised to a selected protein antigen, which bind to that antigen but not to other proteins present in a sample. A variety of immunoassay formats may be used to select antigen-binding molecules specifically immuno-interactive with a particular protein. For example, solid-phase ELISA immunoassays are routinely used to select monoclonal antibodies specifically immuno-interactive with a protein. See Harlow and Lane (1988) Antibodies, A Laboratory Manual, Cold Spring Harbor Publications, New York, for a description of immunoassay formats and conditions that can be used to determine specific immunoreactivity.

For example, specific recognition is provided by a primary antibody (polyclonal or monoclonal) and a secondary detection system is used to detect presence (or binding) of the primary antibody. Detectable labels can be conjugated to the secondary antibody, such as a fluorescent label, a radio-label, or an enzyme (e.g., alkaline phosphatase, horseradish peroxidase) which produces a quantifiable, e.g., colored, product. In another suitable method, the primary antibody itself can be detectably labeled. For example, a protein-specific monoclonal antibody, can be used both as an immunoadsorbent and as an enzyme-labeled probe to detect and quantify complexes formed in the present process or kit.

The amount of such protein present in a sample can be calculated by reference to the amount present in a standard or reference preparation using a linear regression computer algorithm (see Lacobilli et al., (1988) *Breast Cancer Research and Treatment* 11:19-30). In other embodiments, two different monoclonal antibodies to the protein of interest can be employed, one as the immunoadsorbent and the other as an enzyme-labeled probe.

Assays illustrated in the Examples are done in ELISA format with a single antigen per well, per single antibody form or class or isotype. However there are well known methods where they could be combined into a single assay for example using Luminex beads or similar where multiple individual antigens are coated on beads having different intensity of fluorescent label that can be discriminated in an instrument, and the amount of antibody binding to antigen on each bead can be separately measured from the single sample. Similarly the Luminex beads can be coated with antibody or other reagents to capture the individual antibody forms or isotypes from a sample, and then labelled antigen (or antigens) is added and the different isotype reactivities are assessed. The same can be done in micro-arrays or other arrays. Having established useful parameters in ELISA, it is then routine to transfer these findings to multiplex formats. In lateral flow and other point of care devices, where the sample flows across a membrane, it is easy to have the separate antigens present on the membrane as separate stripes or spots, and then detect the antibodies of one or more isotypes together; or else have different capture antibodies for the antibody isotypes, and then detect the (labelled) antigen binding to each of the immobilized antibody stripes or spots. The latter method (isotype capture, detection of labelled antigen bound by the immobilised patient antibody) is a most preferred approach.

Additionally, recent developments in the field of protein capture arrays permit the simultaneous detection and/or quantification of a large number of proteins. For example, low-density protein arrays on filter membranes, such as the universal protein array system (Ge (2000) *Nucleic Acids Res.* 28(2):e3) allow imaging of arrayed antigens using standard ELISA techniques and a scanning charge-coupled device (CCD) detector. Immuno-sensor arrays have also been developed that enable the simultaneous detection of clinical analytes. It is now possible using protein arrays, to profile protein expression in bodily fluids, such as in sera of healthy or diseased subjects, as well as in subjects pre- and post-drug treatment.

Protein capture arrays typically comprise a plurality of protein-capture agents each of which defines a spatially distinct feature of the array. The protein-capture agent can be any molecule or complex of molecules which has the ability to bind a protein and immobilize it to the site of the protein-capture agent on the array. The protein-capture agent may be a protein whose natural function in a cell is to specifically bind another protein, such as an antibody or a receptor. Alternatively, the protein-capture agent may instead be a partially or wholly synthetic or recombinant protein which specifically binds a protein. Alternatively, the protein-capture agent may be a protein which has been selected in vitro from a mutagenized, randomized, or completely random and synthetic library by its binding affinity to a specific protein or peptide target. The selection method used may optionally have been a display method such as ribosome display or phage display, as known in the art. Alternatively, the protein-capture agent obtained via in vitro selection may be a DNA or RNA aptamer which specifically binds a protein target (see, e.g., Potyrailo et al., (1998) *Anal. Chem.* 70:3419-3425; Cohen et al. (1998) *Proc. Natl. Acad Sci. USA* 95:14272-14277; Fukuda, et al. (1997) *Nucleic Acids Symp. Ser.* 37:237-238; available from SomaLogic). For example, aptamers are selected from libraries of oligonucleotides by the Selex™ process and their interaction with protein can be enhanced by covalent attachment, through incorporation of brominated deoxyuridine and UV-activated crosslinking (photoaptamers). Aptamers have the advantages of ease of production by automated oligonucleotide synthesis and the stability and robustness of DNA; universal fluorescent protein stains can be used to detect binding. Alternatively, the in vitro selected protein-capture agent may be a polypeptide (e.g., an antigen) (see, e.g., Roberts and Szostak (1997) *Proc. Natl. Acad Sci. USA* 94:12297-12302).

An alternative to an array of capture molecules is one made through 'molecular imprinting' technology, in which peptides (e.g., from the C-terminal regions of proteins) are used as templates to generate structurally complementary, sequence-specific cavities in a polymerisable matrix; the cavities can then specifically capture (denatured) proteins which have the appropriate primary amino acid sequence (e.g., available from ProteinPrint™ and Aspira Biosystems).

Exemplary protein capture arrays include arrays comprising spatially addressed TB antigens or antibody binding agents, which can facilitate extensive parallel analysis of numerous antigens and antibodies. Such arrays have been shown to have the required properties of specificity and acceptable background, and some are available commercially (e.g., BD Biosciences, Clontech, BioRad and Sigma). Various methods for the preparation of arrays have been reported (see, e.g., Lopez et al. (2003) *J. Chromatogr. B* 787:19-27; Cahill (2000) *Trends in Biotechnology* 7:47-51; U.S. Pat. App. Pub. 2002/0055186; U.S. Pat. App. Pub. 2003/0003599; PCT publication WO 03/062444; PCT publication WO 03/077851; PCT publication WO 02/59601; PCT publication WO 02/39120; PCT publication WO 01/79849; PCT publication WO 99/39210).

Immunoglobulin antigen-binding molecules are made either by conventional immunization (e.g., polyclonal sera and hybridomas), or as recombinant fragments, usually expressed in *E. coli*, after selection from phage display or ribosome display libraries (e.g., available from Cambridge Antibody Technology, BioInvent, Affitech and Biosite). Alternatively, 'combibodies' comprising non-covalent associations of VH and VL domains, can be produced in a matrix format created from combinations of diabody-producing bacterial clones (e.g., available from Domantis). Exemplary antigen-binding molecules for use as protein-capture agents include monoclonal antibodies, polyclonal antibodies, Fv, Fab, Fab' and F(ab')$_2$ immunoglobulin fragments, synthetic stabilized Fv fragments, e.g., single chain Fv fragments (scFv), disulfide stabilized Fv fragments (dsFv), single variable region domains (dAbs) minibodies, combibodies and multivalent antibodies such as diabodies and multi-scFv, single domains from camelids or engineered human equivalents.

Individual spatially distinct protein-capture agents are typically attached to a support surface, which is generally planar or contoured. Common physical supports include glass slides, silicon, microwells, nitrocellulose or PVDF membranes, and magnetic and other microbeads.

While microdrops of protein delivered onto planar surfaces are widely used, related alternative architectures include CD centrifugation devices based on developments in microfluidics (e.g., available from Gyros) and specialized chip designs, such as engineered microchannels in a plate (e.g., The Living Chip™, available from Biotrove) and tiny 3D posts on a silicon surface (e.g., available from Zyomyx).

Particles in suspension can also be used as the basis of arrays, providing they are coded for identification; systems include color coding for microbeads (e.g., available from Luminex, Bio-Rad and Nanomics Biosystems) and semiconductor nanocrystals (e.g., QDots™, available from Quantum Dots), and barcoding for beads (UltraPlex™, available from Smartbeads) and multimetal microrods (Nanobarcodes™ particles, available from Surromed). Beads can also be assembled into planar arrays on semiconductor chips (e.g., available from LEAPS technology and BioArray Solutions). Where particles are used, individual protein-capture agents are typically attached to an individual particle to provide the spatial definition or separation of the array. The particles may then be assayed separately, but in parallel, in a compartmentalized way, for example in the wells of a microtiter plate or in separate test tubes.

In operation, a protein sample (see, e.g., U.S. Pat. App. Pub. 2002/0055186), is delivered to a protein-capture array under conditions suitable for protein or peptide binding, and the array is washed to remove unbound or non-specifically bound components of the sample from the array. Next, the presence or amount of protein or peptide bound to each feature of the array is detected using a suitable detection system. The amount of protein bound to a feature of the array may be determined relative to the amount of a second protein bound to a second feature of the array. In certain embodiments, the amount of the second or subsequent protein in the sample is already known or known to be invariant.

In an illustrative example, fluorescence labeling can be used for detecting protein bound to the array. The same instrumentation as used for reading DNA microarrays is applicable to protein-capture arrays. For differential display, capture arrays (e.g. antibody arrays) can be probed with fluorescently labeled proteins from or are labeled with different fluorophores (e.g., Cy-3 and Cy-5) and mixed, such that the color acts as a readout for changes in target abundance. Fluorescent readout sensitivity can be amplified 10-100 fold by tyramide signal amplification (TSA) (e.g., available from PerkinElmer Lifesciences). Planar waveguide technology (e.g., available from Zeptosens) enables ultrasensitive fluorescence detection, with the additional advantage of no washing procedures. High sensitivity can also be achieved with suspension beads and particles, using phycoerythrin as label (e.g., available from Luminex) or the properties of semiconductor nanocrystals (e.g., available from Quantum Dot). Fluorescence resonance energy transfer has been adapted to detect binding of unlabelled ligands, which may be useful on arrays (e.g., available from Affibody). Several alternative readouts have been developed, including adaptations of surface plasmon resonance (e.g., available from HTS Biosystems and Intrinsic Bioprobes), rolling circle DNA amplification (e.g., available from Molecular Staging), mass spectrometry (e.g., available from Sense Proteomic, Ciphergen, Intrinsic and Bioprobes), resonance light scattering (e.g., available from Genicon Sciences) and atomic force microscopy (e.g., available from BioForce Laboratories). A microfluidics system for automated sample incubation with arrays on glass slides and washing has been co-developed by NextGen and Perkin Elmer Life Sciences.

In certain embodiments, the techniques used for detection of dIgA or other pre-selected products will include internal or external standards to permit quantitative or semi-quantitative determination of those products, to thereby enable a valid comparison of the level or functional activity of these expression products in a biological sample with the corresponding expression products in a reference sample or samples. Such standards can be determined by the skilled practitioner using standard protocols. In specific examples, absolute values for the level or functional activity of individual expression products are determined. Controls may include—individual and population control and samples from diagnostic tests—an earlier time point.

In specific embodiments, the diagnostic method is implemented using a system as disclosed, for example, in International Publication No. WO 02/090579 and in copending PCT Application No. PCT/AU03/01517 filed Nov. 14, 2003, comprising at least one end station coupled to a base station. The base station is typically coupled to one or more databases comprising predetermined data from a number of individuals representing the level TB antigen specific antibodies and their isotype structure (dimeric/polymeric) or subclass, when the predetermined data was collected. In operation, the base station is adapted to receive from the end station, typically via a communications network, subject data representing a measured or normalized level of at least one antibody type in a biological sample obtained from a test subject and to compare the subject data to the predetermined data stored in the database(s). Comparing the subject and predetermined data allows the base station to determine the status of the subject in accordance with the results of the comparison. Thus, the base station attempts to identify individuals having similar parameter values to the test subject and once the status has been determined on the basis of that identification, the base station provides an indication of the diagnosis to the end station. In an embodiment, recombinant pIgR is sub-licensed for use in TB antigen screening or TB serological diagnosis.

Each embodiment in this specification is to be applied mutatis mutandis to every other embodiment unless expressly stated otherwise.

Functionally equivalent methods and kits employing such methods and kits are clearly within the scope of the invention as described herein.

The present invention is further described by the following non-limiting Examples.

Example 1

ELISA Shows Preferential Binding of Chimeric pIgR to dIgA Over IgM, but Strong Binding of Human pIgR to IgM As shown in FIG. 8, an ELISA is performed comparing the binding of HpIgR and R/HpIgR to human IgM and dIgA indicating preferential binding of Chimeric pIgR to dIgA over IgM, but strong binding of human pIgR to IgM. HpIgR or R/HpIgR were immobilised on 96-well Nunc Immulon plates overnight at 4° C. Dilutions of purified human IgM or dIgA in PBS were bound to the immobilised pIgR forms overnight. After washing, the captured IgM or dIgA were detected using anti-IgM or anti-IgA conjugated to horseradish peroxidase (HRP) and colorimetric substrate TMB. The results demonstrate that HpIgR shows preferential binding to IgM (magenta) as well as binding to dIgA (green), whereas R/HpIgR shows greatly reduced binding to IgM (yellow) but retains strong binding to dIgA (blue).

Example 2

ELISA Shows Detection of Immobilised dIgA Using R/HpIgR with Negligible Background An ELISA was performed comparing the detection of immobilised dIgA using R/HpIgR. Dilutions of purified dIgA or no dIgA (mock) were immobilised on 96-well Nunc Immulon plates that were previously coated with anti-IgA, so that the dIgA was bound to the plate by antibody-antigen interaction rather than passive absorption. The dIgA was detected using R/HpIgR ("tailless") or no pIgR ("mock"), anti-secretory component and anti-mouse HRP and TMB substrate. The results (see FIG. 9) demonstrate R/HpIgR is able to detect dIgA at the lowest concentration tested (31 ng/ml) with strong signal in ELISA with negligible background.

Example 3

ELISA Showing Effective Depletion of Ha V-Specific IgM in IgM Capture

An ELISA was conducted demonstrating the detection of HAV-specific IgM in IgM capture, using serial dilutions of serum from a patient with acute HAV infection (Accurun HAV panel sample 121). The serum sample is either untouched before dilution (untouched, purple) or substantially depleted of IgM using Capture-Select IgM (BAC) (red). The results (see FIG. 12) show that this IgM depletion method reduces the level of HAV-specific IgM in the sample by around 256-fold compared to untouched serum.

Example 4

ELISA Shows Detection of Hepatitis a Virus-Specific dIgA Compared to IgM in an Individual Patient, with or without Depletion of IgM An ELISA was conducted demonstrating the detection of HAV-specific dIgA in R/HpIgR capture, using serial dilutions of serum from a patient with acute HAV infection (Accurun HAV panel sample 121). The serum sample is either untouched before dilution (untouched, purple) or substantially depleted of IgM using Capture-Select IgM (BAC) (red). The results show firstly the strong signal that is obtained demonstrating the detection of HAV-specific dIgA, and secondly that this signal is specific for dIgA not IgM because the IgM depletion method did not substantially reduce the level of HAV-specific reactivity compared to untouched serum, in contrast to the results shown in FIG. 12 for IgM detection.

Example 5

R/HpIgR Capture of Antigen-Specific dIgA for the Diagnosis of Acute HAV Infection An ELISA was conducted demonstrating the detection of HAV-specific dIgA in R/HpIgR capture, using serial dilutions of serum from a patient with acute HAV infection (Accurun HAV panel sample 121). The serum sample is either untouched before dilution (untouched, purple) or substantially depleted of IgM using Capture-Select IgM (BAC) (red). The results (see FIG. 13) show firstly the strong signal that is obtained demonstrating the detection of HAV-specific dIgA, and secondly that this signal is specific for dIgA not IgM because the IgM depletion method did not substantially reduce the level of HAV-specific reactivity compared to untouched serum, in contrast to the results shown in FIG. 12 for IgM detection.

An ELISA was performed demonstrating the detection of HAV-specific dIgA in R/HpIgR capture, using sera from patients with or without acute HAV infection (Accurun HAV panel, positive (POS), low positive (LOW POS), or negative (NEG)). The results (FIG. 14) show the strong detection of HAV-specific dIgA in all POS samples and in one of two LOW POS samples, with minimal background reactivity in NEG samples, demonstrating the utility of R/HpIgR capture of antigen-specific dIgA for the diagnosis of acute HAV infection.

Example 6

R/HpIgR Capture and Utility of HpIgR Capture for Diagnosis of Acute HEV Infection An ELISA was conducted demonstrating the detection of hepatitis E virus (HEV)-specific dIgA in R/HpIgR capture or HpIgR capture, using sera from patients with or without acute HEV infection. On the left of FIG. 15, the ELISA OD of individual samples is shown, demonstrating the utility of R/HpIgR capture of antigen-specific dIgA for the diagnosis of acute HEV infection, with lower but still significant utility of HpIgR capture for this purpose, and negligible background reactivity in either example. On the right of FIG. 15, the reactivity of serial dilutions of each serum sample is shown, confirming the utility of R/HpIgR capture and lower utility of HpIgR capture for diagnosis of acute HEV infection. It is likely that the lower utility of HpIgR capture in these examples is due to the much higher overall concentration of IgM in serum versus dIgA, resulting in only a low proportion of the IgM captured by HpIgR being specific for HEV.

Example 7

Detection of Antigen-Specific dIgA or IgM Illustrated Using HEV Infected Patients Comparison of HEV-specific dIgA versus HEV-specific IgM. Both methods are able to detect all HEV-infected patients with strong ELISA signals (FIG. 17), compared to extremely low background for control (HEV-negative) patients in the dIgA assay, and low background in the IgM assay. Notably, some samples show higher levels of dIgA compared to IgM (sample J13, J7), while others show higher levels of IgM compared to dIgA (J4, J11). This demonstrates that the dIgA and IgM responses in patients are independent, and suggests that a combination of both IgM and dIgA detection may be useful in some desirable assay formats. FIG. 17 illustrates that the dIgA assay involved essentially no background while the commercial IgM assay which is highly optimised gives low but detectable background.

Comparison of HEV-specific dIgA versus HEV-specific IgM is conducted using sera that are either untouched, or substantially depleted of IgM using Capture-Select IgM, and then serially diluted. The results (FIG. 18) confirm that the IgM assay is specific for IgM, because the reactivity is ablated by IgM depletion, whereas the dIgA assay is predominantly specific for dIgA and not IgM, because the reactivity is only slightly affected by IgM depletion.

Comparison of HEV-specific dIgA versus HEV-specific IgM is conducted using sera that are either untouched, or substantially depleted of IgM using Capture-Select IgM. The results (FIG. 19) confirm that the IgM assay is specific for IgM, because the reactivity is ablated by IgM depletion, whereas the dIgA assay is predominantly specific for dIgA and not IgM, because the reactivity is only slightly affected by IgM depletion.

Comparison of HEV-specific dIgA versus HEV-specific IgM is conducted using sera that are either untouched, or substantially depleted of IgM using Capture-Select IgM. The results (FIG. 20) confirm that the IgM assay is specific for IgM, because the reactivity is ablated by IgM depletion, whereas the dIgA assay is predominantly specific for dIgA and not IgM, because the reactivity is only slightly affected by IgM depletion. The reduction in dIgA activity following IgM depletion is statistically significant when using a paired T-test to compare samples before and after depletion, but is not significant when using a Mann-Whitney test to compare the overall sample sets before and after depletion.

Example 8

R/HpIgR Capture and Detection of Mouse dIgA

An ELISA is conducted demonstrating that the R/HpIgR can be used in both capture (A) and detection (B) of mouse dimeric IgA, with negligible background reactivity to monomeric (human) IgA. FIG. 21A. Dilutions of purified mouse IgA monoclonal antibody 3H1 (anti-HAV) or purified monomeric human IgA were coated on plates and detected with R/HpIgR and anti-SC antibodies. B. R/HpIgR was coated on plates and dilutions of purified mouse IgA monoclonal antibody 3H1 or purified monomeric human IgA were allowed to bind overnight, then detected with anti-mouse IgA or anti-human IgA. The binding of IgA from diverse species to human or rabbit pIgR is known in the art, and this demonstrates that the novel pIgR strategy described herein has utility for diagnosis of infection in other species.

An ELISA is conducted demonstrating that the R/HpIgR is equally effective for detection of mouse dimeric IgA and human dimeric IgA, with negligible background reactivity to monomeric human IgA. FIG. 22A. Dilutions of purified mouse IgA monoclonal antibody 3H1 (anti-HAV) or purified dimeric or monomeric human IgA were coated on plates and detected with R/HpIgR and anti-SC antibodies.

Example 9

Assessment of HIV Pathogenesis and Illustration of Utility of SIgA/dIgA Ratios in HIV-Infected Subjects A schematic of one of several typical assays (see FIG. 27) that can be used to measure the relative amount of different IgA forms in order to estimate the SIgA/dIgA ratio. In this example, the amount of dIgA is measured by capture of dIgA using R/HpIgR, and detection using monoclonal antibodies against either IgA1, or IgA2, or against both IgA subclasses. Monomeric IgA does not bind to pIgR; SIgA does bind to R/HpIgR but with lower affinity than dIgA and can be removed by washing with 3.5 M urea if desired. SIgA is measured in the same way but using anti-SC antibody capture instead of R/HpIgR. The SIgA/dIgA ratio is then calculated as a simple ratio of the assay reactivities for SIgA and dIgA.

An ELISA is conducted demonstrating the detection of highly elevated SIgA2/dIgA2 (S/d) ratios in a proportion of HIV-infected patients, compared to the majority of HIV-infected patients and all control subjects (magenta). The assay cutoff for elevated SIgA/dIgA was set as the mean plus 3 standard deviations of the SIgA/dIgA ratio among non-HIV control subjects, and 7/30 HIV-infected subjects showed SIgA/dIgA ratios above this cutoff. Notably, the range of SIgA/dIgA ratios among normal subjects is smaller than the range for SIgA or dIgA alone, because the role of dIgA as the precursor of SIgA provides a normalising effect for each patient.

An ELISA is conducted demonstrating the total amount of SIgA in patient and control sera (arbitrary units). The amount of SIgA2 in normal patients varies over an 11-fold range, but all normal controls fall within a cutoff of the mean plus 3 standard deviations. The amount of SIgA2 in HIV-infected patients varies over a slightly larger range (16-fold), but only 2/30 patients are above the cutoff range (see FIG. 29). Among the HIV-infected patients, those patients who demonstrated elevated SIgA2/dIgA2 ratios in FIG. 28 are indicated with red markers (diamonds at ranks 11, 16, 19, 23, 24, 28 and 30). It can be seen that these patients with elevated SIgA2/dIgA2 ratios are found throughout much of the normal range of the total SIgA2 signal, and cannot be distinguished from the normal controls on the basis of the total SIgA2 alone. This confirms the utility of using SIgA/dIgA ratios because the role of dIgA as the precursor of SIgA provides a normalising effect for each patient. The R/HpIgR system provides the utility for measuring this ratio.

FIG. 30 illustrates a correlation of SIgA2/dIgA2 ratio versus the immune activation marker, CD8+ HLA-DR+ CD38+ T-cells, in a different HIV-infected population to that shown in FIGS. 28 and 29. While the overall correlation is low, it is apparent that patients with SIgA2/dIgA2 ratios of >4 in this experiment have elevated levels of immune activation markers (p<0.0001).

FIG. 31 illustrates a correlation of SIgA1/dIgA1 ratio versus the immune activation marker, CD8+ HLA-DR+ CD38+ T-cells, in the same population as FIG. 30. While the overall correlation is lower again than for IgA2, it is apparent that patients with SIgA1/dIgA1 ratios of >10 in this experiment have elevated levels of immune activation markers (p<0.015). The lower correlation for IgA1 and higher cutoff ratio (10 versus 4) for significance highlights the value of specifically measuring IgA2 because of its predominant site of synthesis in the gut, being the tissue in which leakage of SIgA is likely to be clinically relevant marker of gut leakage and immune activation.

FIG. 32 illustrates a correlation of SIgA1/dIgA1 ratio versus SIgA2/dIgA2 ratio, in the same population as FIGS. 30 and 31. While SIgA1/dIgA1 ratios are significantly correlated with SIgA2/dIgA2, it is notable that there are some patients with highly elevated SIgA1/dIgA1 ratios and relatively low SIgA2/dIgA2 ratios. This suggests that there may be some value in measuring IgA1, or total IgA, in addition to IgA2 in the calculation of SIgA/dIgA ratios as a measure of gut leakage and immune activation.

The disclosure of every patent, patent application, and publication cited herein is hereby incorporated herein by reference in its entirety.

Many modifications will be apparent to those skilled in the art without departing from the scope of the present invention.

TABLE 1

Summary of sequence identifiers

| SEQUENCE ID NO: | DESCRIPTION |
|---|---|
| 1 | Nucleotide sequence of human pIgR |
| 2 | Amino acid sequence of human pIgR |
| 3 | Nucleotide sequence of rabbit pIgR |
| 4 | Amino acid sequence of rabbit pIgR |
| 5 | Nucleotide sequence of chimeric human/rabbit pIgR |
| 6 | Amino acid sequence of chimeric human/rabbit pIgR |
| 7 | Nucleotide sequence of N-terminal rabbit domain 1 chimeric human/rabbit pIgR |
| 8 | Amino acid sequence of N-terminal rabbit domain 1 chimeric human/rabbit pIgR |
| 9 | Nucleotide sequence of C-terminal human domains 2-4 of chimeric human/rabbit pIgR |
| 10 | Amino acid sequence of C-terminal human domains 2-4 of chimeric human/rabbit pIgR |
| 11 | Nucleotide sequence of human pIgR with cytoplasmic domain of CD4 |
| 12 | Amino acid sequence of human pIgR with cytoplasmic domain of CD4 |
| 13 | Nucleotide sequence of rabbit pIgR cytoplasmic domain with cytoplasmic domain of CD4 |
| 14 | Amino acid sequence of rabbit pIgR with cytoplasmic domain of CD4 |
| 15 | Nucleotide sequence of chimeric human/rabbit pIgR with cytoplasmic domain of CD4 |
| 16 | Amino acid sequence of chimeric human/rabbit pIgR with cytoplasmic domain of CD4 |
| 17 | Nucleotide sequence of N-terminal rabbit domain 1 of chimeric human/rabbit pIgR with cytoplasmic domain of CD4 |
| 18 | Amino acid sequence N-terminal rabbit domain 1 of chimeric human/rabbit pIgR with cytoplasmic domain of CD4 |
| 19 | Nucleotide sequence of C-terminal human domains 2-4 of chimeric human/rabbit pIgR with cytoplasmic domain of CD4 |
| 20 | Amino acid sequence of C-terminal human domains 2-4 of chimeric human/rabbit pIgR with cytoplasmic domain of CD4 |

TABLE 2

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |

TABLE 2-continued

Amino acid sub-classification

| Sub-classes | Amino acids |
|---|---|
| Aromatic Residues that influence chain orientation | Tryptophan, Tyrosine, Phenylalanine Glycine and Proline |

TABLE 3

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Brenchley et al. (2006) *Nat Med* 12(12): 1365-1371
Cahill (2000) *Trends in Biotechnology* 7:47-51
Cohen (2008) *Science*
Cohen et al. (1998) *Proc. Natl. Acad Sci. USA* 95:14272-14277
Crago et al. (1984) *J Immunol* 132(1): 16-18
Craik C. S. (1985) *Science,* 228:291-297
Cronin et al., *Biochem.* (1988) 27: 4572-4579
French et al. (2009) *J Infect Dis.* 200(8): 1212-1215
Fukuda, et al. (1997) *Nucleic Acids Symp. Ser.* 37:237-238
Ge (2000) *Nucleic Acids Res.* 28(2):e3
Gerit J. A. (1987) *Chem. Rev.,* 87:1079-1105
Harlow and Lane (1988) "*Antibodies: A Laboratory Manual*" Cold Spring Harbor Laboratory
He et al. (2007) *Immunity* 26(6): 812-826
Kaetzel and Bruno (2011) *Mucosal immune defense: Immunoglobulin A*
Knowles J. R. (1987) *Science,* 236:1252-1258
Lacobilli et al., (1988) *Breast Cancer Research and Treatment* 11:19-30
Leatherbarrow R. (1986) *J Prot. Eng.,* 1:7-16
Lopez et al. (2003) *J. Chromatogr. B* 787:19-27
Nilssen et al. (2004) *Gut* 53:487-493
Phillips-Quagliata et al. (2000) *J Immunol* 165: 2544-2555
Potyrailo et al., (1998) *Anal. Chem.* 70:3419-3425
Roberts and Szostak (1997) *Proc. Natl. Acad Sci. USA* 94:12297-12302
Roe et al. (1999) *J Immunol* 162: 6046-52
Sambrook (2001) *Molecular Cloning: A Laboratory Manual,* 3rd Edition, CSHLP, CSH, NY
Shaw W. V. (1987) *Biochem. J.,* 246:1-17
Watson, J. D. et al. (1987) "*Molecular Biology of the Gene*", Fourth Edition, Benjamin/Cummings, Menlo Park, Calif.
Wild D. (2001) "*The Immunoassay Handbook*" Nature Publishing Group
Wilks et al. (1988) *Science,* 242:1541-1544
Woof and Russell (2011) *Mucosal Immunology* 4: 590-597
Zhang et al. (2008) *Nephrol Dial Transplant* 23(1): 207-212

The invention claimed is:

1. A method for assessing levels of a polymeric Ig Receptor (pIgR)-dimeric IgA antibody (dIgA) complex; the method comprising: contacting a biological sample from a subject comprising antibodies with a pIgR comprising in order from N-terminus to C-terminus a rabbit pIgR domain 1 and human pIgR domains 2 to 5, wherein the pIgR binds to dIgA, and assessing the level of the pIgR-dIgA complex, wherein the pIgR does not comprise a transmembrane domain, wherein the pIgR is bound to a solid support, and wherein an elevated level of pIgR-dIgA relative to a reference sample is used to diagnose a subject as having an acute infection selected from the group consisting of hepatitis A virus (HAV), hepatitis C virus (HCV), hepatitis E virus (HEV), and human immunodeficiency virus (HIV), and/or wherein the level of pIgR-dIgA is used to monitor an infection or condition selected from the group consisting of ulcerative colitis, HIV, IBS, leaky gut syndrome, leprosy, syphilis, HAV, HCV, HEV, dengue virus, measles, and rubella.

2. The method of claim 1, wherein the biological sample is a blood, plasma or serum sample.

3. The method of claim 1, wherein the pIgR does not comprise a cytoplasmic domain.

4. The method of claim 1, wherein the pIgR is recombinantly produced in a glycan deficient cell.

5. The method of claim 1, further comprising, contacting the biological sample with an anti-Secretory Component (SC) binding agent wherein the anti-SC binding agent binds Secretory IgA (SIgA) and forms a SIgA-binding agent complex.

6. The method of claim 1, further comprising, contacting a sample comprising the pIgR-dIgA complex with a denaturing solution to remove any SIgA from the complex and measuring the ratio of SigA and dIgA in the biological sample.

7. The method of claim 6, wherein the level or ratio of SiGa2 to dIgA2 and/or SIgA1 to dIgA1 are determined.

8. A method for determining gut wall integrity in a subject, the method comprising:
(i) contacting a biological sample obtained from the subject with a polymeric Ig Receptor (pIgR) comprising in order from N-terminus to C-terminus a rabbit pIgR domain 1 and human pIgR domains 2 to 5, wherein the pIgR that binds to dimeric IgA antibody (dIgA) and forms a pIgR-dIgA complex, wherein the pIgR does not comprise a transmembrane domain, (ii) contacting the biological sample with a specific anti-Secretory IgA (SIgA) binding agent or anti-Secretory Component (SC) binding agent which binds to SiGa and forms an SigA-binding agent complex, and (iii) measuring a ratio of SigA2 of (ii) to dIgA2 of (i) and measuring a ratio of SIgA1 of (ii) to dIgA1 of (ii) wherein a ratio of SIgA2 to dIgA2 of >4 or a ratio of SIgA1 to dIgA1>10 is indicative of gut leakage and immune activation.

9. A method for detecting the presence of antigen-specific dimeric IgA antibody (dIgA) in a subject, the method comprising contacting a biological sample comprising antibodies obtained from a subject with a polymeric Ig Receptor (pIgR) comprising in order from N-terminus to C-terminus a rabbit pIgR domain 1 and human pIgR domaing 2 to 5, wherein the pIgR binds to dIgA, and measuring the level of antigen-specific dIgA bound to the pIgR, wherein the pIgR does not comprise a transmembrane domain, wherein the pIgR is bound to a solid support, wherein the subject has a condition selected from the group consisting of HIV, leprosy, syphilis, hepatitis, dengue virus, measles, and rubella, and wherein detection of the level of antigen-specific dIgA bound to the pIgR facilitates the selection of treatment for the condition.

* * * * *

SEQUENCE LISTING

```
<160> NUMBER OF SEQ ID NOS: 20

<210> SEQ ID NO 1
<211> LENGTH: 1920
<212> TYPE: DNA
<213> ORGANISM: Homo sapiens

<400> SEQUENCE: 1
atgctgctct tcgtgctcac ctgcctgctg gcggtcttcc cagccatctc cacgaagagt      60
cccatatttg gtcccgagga ggtgaatagt gtggaaggta actcagtgtc catcacgtgc     120
tactacccac ccacctctgt caaccggcac acccggaagt actggtgccg gcagggagct     180
agaggtggct gcataaccct catctcctcg gagggctacg tctccagcaa atatgcaggc     240
agggctaacc tcaccaactt cccggagaac ggcacatttg tggtgaacat tgcccagctg     300
agccaggatg actccgggcg ctacaagtgt ggcctgggca tcaatagccg aggcctgtcc     360
tttgatgtca gcctggaggt cagccagggt cctgggctcc taaatgacac taaagtctac     420
acagtggacc tgggcagaac ggtgaccatc aactgccctt tcaagactga gaatgctcaa     480
aagaggaagt ccttgtacaa gcagatagcc ctgtaccctg tgctggtcat cgactccagt     540
```

```
ggttatgtaa atcccaacta tacaggaaga atacgccttg atattcaggg tactggccag    600
ttactgttca gcgttgtcat caaccaactc aggctcagcg atgctgggca gtatctctgc    660
caggctgggg atgattccaa tagtaataag aagaatgctg acctccaagt gctaaagccc    720
gagcccgagc tggtttatga agacctgagg ggctcagtga ccttccactg tgccctgggc    780
cctgaggtgg caaacgtggc caaatttctg tgccgacaga gcagtgggga aaactgtgac    840
gtggtcgtca cacccctggg gaagagggcc ccagcctttg agggcaggat cctgctcaac    900
ccccaggaca aggatggctc attcagtgtg gtgatcacag gcctgaggaa ggaggatgca    960
gggcgctacc tgtgtggagc ccattcggat ggtcagctgc aggaaggctc gcctatccag   1020
gcctggcaac tcttcgtcaa tgaggagtcc acgattcccc gcagcccac tgtggtgaag    1080 ggggtggcag gaggctctgt ggccgtgctc tgccctaca accgtaagga agcaaaagc     1140 atcaagtact ggtgtctctg gaagggggcc cagaatggcc gctgcccct gctggtggac    1200 agcgaggggt gggttaaggc ccagtacgag ggccgcctct ccctgctgga ggagccaggc   1260
aacggcacct tcactgtcat cctcaaccag ctcaccagcc gggacgccgg cttctactgg   1320
tgtctgacca acggcgatac tctctggagg accaccgtgg agatcaagat tatcgaagga   1380
gaaccaaacc tcaaggtacc agggaatgtc acggctgtgc tgggagagac tctcaaggtc   1440
ccctgtcact ttccatgcaa attctcctcg tacgagaaat actggtgcaa gtggaataac   1500
acgggctgcc aggccctgcc cagccaagac gaaggcccca gcaaggcctt cgtgaactgt   1560
gacgagaaca gccggcttgt ctccctgacc ctgaacctgg tgaccagggc tgatgagggc   1620
tggtactggt gtggagtgaa gcagggccac ttctatggag agactgcagc cgtctatgtg   1680
gcagttgaag agaggaaggc agcggggtcc cgcgatgtca gcctagcgaa ggcagacgct   1740
gctcctgatg agaaggtgct agactctggt tttcgggaga ttgagaacaa gccattcag    1800 gatcccaggc tttttgcaga ggaaaaggcg gtggcagata caagagatca gccgatggg    1860 agcagagcat ctgtggattc cggcagctct gaggaacaag gtggaagctc agaaggtga    1920
```

<210> SEQ ID NO 2
<211> LENGTH: 639
<212> TYPE: PRT
<213> ORGANISM: Homo sapiens

<400> SEQUENCE: 2

```
Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
```

-continued

```
            130                 135                 140
Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
                180                 185                 190

Leu Asp Ile Gln Gly Thr Gly Gln Leu Leu Phe Ser Val Val Ile Asn
                195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
                260                 265                 270

Gln Ser Ser Gly Glu Asn Cys Asp Val Val Val Asn Thr Leu Gly Lys
                275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
                340                 345                 350

Pro Arg Ser Pro Thr Val Val Lys Gly Val Ala Gly Gly Ser Val Ala
                355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
                420                 425                 430

Ser Arg Asp Ala Gly Phe Tyr Trp Cys Leu Thr Asn Gly Asp Thr Leu
                435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
                500                 505                 510

Pro Ser Lys Ala Phe Val Asn Cys Asp Glu Asn Ser Arg Leu Val Ser
                515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560
```

```
Ala Val Glu Glu Arg Lys Ala Ala Gly Ser Arg Asp Val Ser Leu Ala
            565                 570                 575

Lys Ala Asp Ala Ala Pro Asp Glu Lys Val Leu Asp Ser Gly Phe Arg
        580                 585                 590

Glu Ile Glu Asn Lys Ala Ile Gln Asp Pro Arg Leu Phe Ala Glu Glu
    595                 600                 605

Lys Ala Val Ala Asp Thr Arg Asp Gln Ala Asp Gly Ser Arg Ala Ser
610                 615                 620

Val Asp Ser Gly Ser Ser Glu Glu Gln Gly Gly Ser Ser Arg Arg
625                 630                 635

<210> SEQ ID NO 3
<211> LENGTH: 1947
<212> TYPE: DNA
<213> ORGANISM: RABBIT

<400> SEQUENCE: 3
atggctctct tcttgctcac ctgcctgctg gctgtctttt cagcggccac ggcacaaagc      60
tccttattgg gtcccagctc catatttggt cccggggagg tgaatgtttt ggaaggcgac     120
tcggtgtcca tcacatgcta ctacccaaca acctccgtca cccggcacag ccggaagttc     180
tggtgccggg aagaggagag cggccgctgc gtgacgcttg cctcgaccgg ctacacgtcc     240
caggaatact ccgggagagg caagctcacc gacttccctg ataaagggga gtttgtggtg     300
actgttgacc aactcaccca gaacgactca gggagctaca gtgtggcgt gggagtcaac      360 ggccgtggcc tggacttcgg tgtcaacgtg ctggtcagcc agaagccaga gcctgatgac     420
gttgtttaca acaatatga gagttataca gtaaccatca cctgccctt cacatatgcg       480 actaggcaac taaagaagtc cttttacaag gtggaagacg ggaacttgt actcatcatt      540 gattccagca gtaaggaggc aaaggacccc aggtataagg cagaataac gttgcagatc      600 caaagtacca cagcaaaaga attcacagtc accatcaagc atttgcagct caatgatgct     660
gggcagtatg tctgccagag tggaagcgac cccactgctg aagaacagaa cgttgaccctc    720 cgactgctaa ctcctggtct gctctatgga aacctgggg gctcggtgac cttttgaatgt     780 gccctggact ctgaagacgc aaacgcggta gcatccttgc gccaggttag ggtggcaat     840 gtggtcattg acagccaggg gacaatagat ccagccttcg agggcaggat cctgttcacc     900
aaggctgaga cggccactt cagtgtagtg atcgcaggcc tgaggaagga agacacaggg      960
aactatctgt gcggagtcca gtccaatggt cagtctgggg atgggcccac ccagcttcgg   1020
caactcttcg tcaatgaaga gatcgacgtg tcccgcagcc cctgtgtt gaagggcttt     1080 ccaggaggct ccgtgaccat acgctgcccc tacaacccga agagaagcga cagccacctg   1140
cagctgtatc tctgggaagg gagtcaaacc cgccatctgc tggtggacag cggcgagggg   1200
ctggttcaga aagactacac aggcaggctg gccctgttcg aagagcctgg caatggcacc   1260
ttctcagtcg tcctcaacca gctcactgcc gaggatgaag gcttctactg tgtgtgtcagc   1320 gatgacgatg agtccctgac gacttcggtg aagctccaga tcgttgacgg agaaccaagc   1380
cccacgatcg acaagttcac tgctgtgcag ggagagcctg ttgagatcac ctgccacttc   1440
ccatgcaaat acttctcctc cgagaagtac tggtgcaagt ggaatgacca tggctgcgag   1500
gacctgccca ctaagctcag ctccagcggc gaccttgtga atgcaacaa caacctggtc   1560 ctcacccctga ccttggactc ggtcagcgaa gatgacgagg ctggtactg tgtgtggcgcg   1620 aaagacgggc acgagtttga agaggttgcg gccgtcaggg tggagctgac agagccagcc   1680
```

```
aaggtagctg tcgagccagc caaggtacct gtcgacccag ccaaggcagc ccccgcgcct   1740
gctgaggaga aggccaaggc gcggtgccca gtgcccagga gaaggcagtg gtacccattg   1800
tcaaggaagc tgagaacaag ttgtccagaa cctcggctcc ttgcggagga ggtagcagtg   1860
cagagtgcgg aagacccagc cagtgggagc agagcgtctg tggatgccag cagtgcttcg   1920
ggacaaagcg ggagtgccaa aaggtga                                      1947
```

<210> SEQ ID NO 4
<211> LENGTH: 648
<212> TYPE: PRT
<213> ORGANISM: RABBIT

<400> SEQUENCE: 4

Met Ala Leu Phe Leu Leu Thr Cys Leu Leu Ala Val Phe Ser Ala Ala
1               5                   10                  15

Thr Ala Gln Ser Ser Leu Leu Gly Pro Ser Ser Ile Phe Gly Pro Gly
                20                  25                  30

Glu Val Asn Val Leu Glu Gly Asp Ser Val Ser Ile Thr Cys Tyr Tyr
            35                  40                  45

Pro Thr Thr Ser Val Thr Arg His Ser Arg Lys Phe Trp Cys Arg Glu
        50                  55                  60

Glu Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
            100                 105                 110

Tyr Lys Cys Gly Val Gly Val Asn Gly Arg Gly Leu Asp Phe Gly Val
        115                 120                 125

Asn Val Leu Val Ser Gln Lys Pro Glu Pro Asp Asp Val Val Tyr Lys
    130                 135                 140

Gln Tyr Glu Ser Tyr Thr Val Thr Ile Thr Cys Pro Phe Thr Tyr Ala
145                 150                 155                 160

Thr Arg Gln Leu Lys Lys Ser Phe Tyr Lys Val Glu Asp Gly Glu Leu
                165                 170                 175

Val Leu Ile Ile Asp Ser Ser Lys Glu Ala Lys Asp Pro Arg Tyr
            180                 185                 190

Lys Gly Arg Ile Thr Leu Gln Ile Gln Ser Thr Thr Ala Lys Glu Phe
        195                 200                 205

Thr Val Thr Ile Lys His Leu Gln Leu Asn Asp Ala Gly Gln Tyr Val
    210                 215                 220

Cys Gln Ser Gly Ser Asp Pro Thr Ala Glu Glu Gln Asn Val Asp Leu
225                 230                 235                 240

Arg Leu Leu Thr Pro Gly Leu Leu Tyr Gly Asn Leu Gly Gly Ser Val
                245                 250                 255

Thr Phe Glu Cys Ala Leu Asp Ser Glu Asp Ala Asn Ala Val Ala Ser
            260                 265                 270

Leu Arg Gln Val Arg Gly Gly Asn Val Val Ile Asp Ser Gln Gly Thr
        275                 280                 285

Ile Asp Pro Ala Phe Glu Gly Arg Ile Leu Phe Thr Lys Ala Glu Asn
    290                 295                 300

Gly His Phe Ser Val Val Ile Ala Gly Leu Arg Lys Glu Asp Thr Gly
305                 310                 315                 320

```
Asn Tyr Leu Cys Gly Val Gln Ser Asn Gly Gln Ser Gly Asp Gly Pro
                325                 330                 335
Thr Gln Leu Arg Gln Leu Phe Val Asn Glu Glu Ile Asp Val Ser Arg
            340                 345                 350
Ser Pro Pro Val Leu Lys Gly Phe Pro Gly Gly Ser Val Thr Ile Arg
        355                 360                 365
Cys Pro Tyr Asn Pro Lys Arg Ser Asp Ser His Leu Gln Leu Tyr Leu
    370                 375                 380
Trp Glu Gly Ser Gln Thr Arg His Leu Leu Val Asp Ser Gly Glu Gly
385                 390                 395                 400
Leu Val Gln Lys Asp Tyr Thr Gly Arg Leu Ala Leu Phe Glu Glu Pro
                405                 410                 415
Gly Asn Gly Thr Phe Ser Val Val Leu Asn Gln Leu Thr Ala Glu Asp
            420                 425                 430
Glu Gly Phe Tyr Trp Cys Val Ser Asp Asp Glu Ser Leu Thr Thr
        435                 440                 445
Ser Val Lys Leu Gln Ile Val Asp Gly Glu Pro Ser Pro Thr Ile Asp
    450                 455                 460
Lys Phe Thr Ala Val Gln Gly Glu Pro Val Glu Ile Thr Cys His Phe
465                 470                 475                 480
Pro Cys Lys Tyr Phe Ser Ser Glu Lys Tyr Trp Cys Lys Trp Asn Asp
                485                 490                 495
His Gly Cys Glu Asp Leu Pro Thr Lys Leu Ser Ser Gly Asp Leu
            500                 505                 510
Val Lys Cys Asn Asn Asn Leu Val Leu Thr Leu Thr Leu Asp Ser Val
        515                 520                 525
Ser Glu Asp Asp Glu Gly Trp Tyr Trp Cys Gly Ala Lys Asp Gly His
    530                 535                 540
Glu Phe Glu Glu Val Ala Ala Val Arg Val Glu Leu Thr Glu Pro Ala
545                 550                 555                 560
Lys Val Ala Val Glu Pro Ala Lys Val Pro Val Asp Pro Ala Lys Ala
                565                 570                 575
Ala Pro Ala Pro Ala Glu Glu Lys Ala Lys Ala Arg Cys Pro Val Pro
            580                 585                 590
Arg Arg Arg Gln Trp Tyr Pro Leu Ser Arg Lys Leu Arg Thr Ser Cys
        595                 600                 605
Pro Glu Pro Arg Leu Leu Ala Glu Val Ala Val Gln Ser Ala Glu
    610                 615                 620
Asp Pro Ala Ser Gly Ser Arg Ala Ser Val Asp Ala Ser Ser Ala Ser
625                 630                 635                 640
Gly Gln Ser Gly Ser Ala Lys Arg
                645

<210> SEQ ID NO 5
<211> LENGTH: 1935
<212> TYPE: DNA
<213> ORGANISM: Artificial Sequence
<220> FEATURE:
<223> OTHER INFORMATION: CHIMERA (R/HpIgR)

<400> SEQUENCE: 5
atggctctct tcttgctcac ctgcctgctg ctgtcttttt cagcggccac ggcacaaagc      60
tccttattgg gtcccagctc catatttggt cccggggagg tgaatgtttt ggaaggcgac     120
tcggtgtcca tcacatgcta ctacccaaca acctccgtca cccggcacag ccggaagttc     180
```

-continued

```
tggtgccggg aagaggagag cggccgctgc gtgacgcttg cctcgaccgg ctacacgtcc      240
caggaatact ccgggagagg caagctcacc gacttccctg ataaagggga gtttgtggtg      300
actgttgacc aactcaccca gaacgactca gggagctaca agtgtggcgt gggagtcaac      360
ggccgtggcc tggacttcgg tgtcaacgtg ctggtcagcc agaagccaga gctcctaaat      420
gacactaaag tctacacagt ggacctgggc agaacggtga ccatcaactg ccctttcaag      480
actgagaatg ctcaaaagag gaagtccttg tacaagcaga taggcctgta ccctgtgctg      540
gtcatcgact ccagtggtta tgtaaatccc aactatacag gaagaatacg ccttgatatt      600
cagggtactg ccagttact gttcagcgtt gtcatcaacc aactcaggct cagcgatgct      660
gggcagtatc tctgccaggc tggggatgat ccaatagta ataagaagaa tgctgacctc      720
caagtgctaa agcccgagcc cgagctggtt tatgaagacc tgagggctc agtgaccttc      780 cactgtgccc tgggccctga ggtggcaaac gtggccaaat ttctgtgccg acagagcagt      840
ggggaaaact gtgacgtggt cgtcaacacc ctggggaaga gggccccagc ctttgagggc      900
aggatcctgc tcaacccca ggacaaggat ggctcattca gtgtggtgat cacaggcctg      960
aggaaggagg atgcagggcg ctacctgtgt ggagcccatt cggatggtca gctgcaggaa      1020
ggctcgccta tccaggcctg caactcttc gtcaatgagg agtccacgat cccccgcagc      1080
cccactgtgg tgaaggggt ggcaggaggc tctgtggccg tgctctgccc ctacaaccgt      1140
aaggaaagca aaagcatcaa gtactggtgt ctctgggaag gggcccagaa tggccgctgc      1200
cccctgctgg tggacagcga ggggtgggtt aaggcccagt acgagggccg cctctccctg      1260
ctggaggagc caggcaacgg caccttcact gtcatcctca accagctcac cagccgggac      1320
gccggcttct actggtgtct gaccaacggc gatactctct ggaggaccac cgtggagatc      1380
aagattatcg aaggagaacc aaacctcaag gtaccaggga atgtcacggc tgtgctggga      1440
gagactctca aggtcccctg tcactttcca tgcaaattct cctcgtacga gaaatactgg      1500
tgcaagtgga ataacacggg ctgccaggcc ctgcccagcc aagacgaagg ccccagcaag      1560
gccttcgtga actgtgacga gaacagccgg cttgtctccc tgaccctgaa cctggtgacc      1620
agggctgatg agggctggta ctggtgtgga gtgaagcagg gccacttcta tggagagact      1680
gcagccgtct atgtggcagt tgaagagagg aaggcagcgg ggtcccgcga tgtcagccta      1740
gcgaaggcag acgctgctcc tgatgagaag gtgctagact ctggttttcg ggagattgag      1800
aacaaagcca ttcaggatcc caggcttttt gcagaggaaa aggcggtggc agatacaaga      1860
gatcaagccg atgggagcag agcatctgtg gattccggca gctctgagga caaggtgga      1920 agctccagaa ggtga                                                      1935
```

<210> SEQ ID NO 6
<211> LENGTH: 644
<212> TYPE: PRT
<213> ORGANISM: Artificial Sequence
<220> FEATURE:
<223> OTHER INFORMATION: CHIMERA (R/HpIgR)

<400> SEQUENCE: 6

```
Met Ala Leu Phe Leu Leu Thr Cys Leu Leu Ala Val Phe Ser Ala Ala
1               5                   10                  15

Thr Ala Gln Ser Ser Leu Leu Gly Pro Ser Ser Ile Phe Gly Pro Gly
                20                  25                  30

Glu Val Asn Val Leu Glu Gly Asp Ser Val Ser Ile Thr Cys Tyr Tyr
            35                  40                  45
```

-continued

```
Pro Thr Thr Ser Val Thr Arg His Ser Arg Lys Phe Trp Cys Arg Glu
 50                  55                  60
Glu Glu Ser Gly Arg Cys Val Thr Leu Ala Ser Thr Gly Tyr Thr Ser
 65                  70                  75                  80
Gln Glu Tyr Ser Gly Arg Gly Lys Leu Thr Asp Phe Pro Asp Lys Gly
                 85                  90                  95
Glu Phe Val Val Thr Val Asp Gln Leu Thr Gln Asn Asp Ser Gly Ser
            100                 105                 110
Tyr Lys Cys Gly Val Gly Val Asn Gly Arg Gly Leu Asp Phe Gly Val
        115                 120                 125
Asn Val Leu Val Ser Gln Lys Pro Glu Leu Leu Asn Asp Thr Lys Val
130                 135                 140
Tyr Thr Val Asp Leu Gly Arg Thr Val Thr Ile Asn Cys Pro Phe Lys
145                 150                 155                 160
Thr Glu Asn Ala Gln Lys Arg Lys Ser Leu Tyr Lys Gln Ile Gly Leu
                165                 170                 175
Tyr Pro Val Leu Val Ile Asp Ser Ser Gly Tyr Val Asn Pro Asn Tyr
            180                 185                 190
Thr Gly Arg Ile Arg Leu Asp Ile Gln Gly Thr Gly Gln Leu Leu Phe
        195                 200                 205
Ser Val Val Ile Asn Gln Leu Arg Leu Ser Asp Ala Gly Gln Tyr Leu
210                 215                 220
Cys Gln Ala Gly Asp Asp Ser Asn Ser Asn Lys Lys Asn Ala Asp Leu
225                 230                 235                 240
Gln Val Leu Lys Pro Glu Pro Glu Leu Val Tyr Glu Asp Leu Arg Gly
                245                 250                 255
Ser Val Thr Phe His Cys Ala Leu Gly Pro Glu Val Ala Asn Val Ala
            260                 265                 270
Lys Phe Leu Cys Arg Gln Ser Ser Gly Glu Asn Cys Asp Val Val Val
        275                 280                 285
Asn Thr Leu Gly Lys Arg Ala Pro Ala Phe Glu Gly Arg Ile Leu Leu
290                 295                 300
Asn Pro Gln Asp Lys Asp Gly Ser Phe Ser Val Val Ile Thr Gly Leu
305                 310                 315                 320
Arg Lys Glu Asp Ala Gly Arg Tyr Leu Cys Gly Ala His Ser Asp Gly
                325                 330                 335
Gln Leu Gln Glu Gly Ser Pro Ile Gln Ala Trp Gln Leu Phe Val Asn
            340                 345                 350
Glu Glu Ser Thr Ile Pro Arg Ser Pro Thr Val Val Lys Gly Val Ala
        355                 360                 365
Gly Gly Ser Val Ala Val Leu Cys Pro Tyr Asn Arg Lys Glu Ser Lys
370                 375                 380
Ser Ile Lys Tyr Trp Cys Leu Trp Glu Gly Ala Gln Asn Gly Arg Cys
385                 390                 395                 400
Pro Leu Leu Val Asp Ser Glu Gly Trp Val Lys Ala Gln Tyr Glu Gly
                405                 410                 415
Arg Leu Ser Leu Leu Glu Glu Pro Gly Asn Gly Thr Phe Thr Val Ile
            420                 425                 430
Leu Asn Gln Leu Thr Ser Arg Asp Ala Gly Phe Tyr Trp Cys Leu Thr
        435                 440                 445
Asn Gly Asp Thr Leu Trp Arg Thr Thr Val Glu Ile Lys Ile Ile Glu
450                 455                 460
Gly Glu Pro Asn Leu Lys Val Pro Gly Asn Val Thr Ala Val Leu Gly
```

```
465                 470                 475                 480
Glu Thr Leu Lys Val Pro Cys His Phe Pro Cys Lys Phe Ser Ser Tyr
                485                 490                 495
Glu Lys Tyr Trp Cys Lys Trp Asn Asn Thr Gly Cys Gln Ala Leu Pro
                500                 505                 510
Ser Gln Asp Glu Gly Pro Ser Lys Ala Phe Val Asn Cys Asp Glu Asn
                515                 520                 525
Ser Arg Leu Val Ser Leu Thr Leu Asn Leu Val Thr Arg Ala Asp Glu
                530                 535                 540
Gly Trp Tyr Trp Cys Gly Val Lys Gln Gly His Phe Tyr Gly Glu Thr
545                 550                 555                 560
Ala Ala Val Tyr Val Ala Val Glu Glu Arg Lys Ala Ala Gly Ser Arg
                565                 570                 575
Asp Val Ser Leu Ala Lys Ala Asp Ala Ala Pro Asp Glu Lys Val Leu
                580                 585                 590
Asp Ser Gly Phe Arg Glu Ile Glu Asn Lys Ala Ile Gln Asp Pro Arg
                595                 600                 605
Leu Phe Ala Glu Glu Lys Ala Val Ala Asp Thr Arg Asp Gln Ala Asp
                610                 615                 620
Gly Ser Arg Ala Ser Val Asp Ser Gly Ser Ser Glu Glu Gln Gly Gly
625                 630                 635                 640
Ser Ser Arg Arg

<210> SEQ ID NO 7
<211> LENGTH: 411
<212> TYPE: DNA
<213> ORGANISM: Artificial Sequence
<220> FEATURE:
<223> OTHER INFORMATION: CHIMERA (R/HpIgR)

<400> SEQUENCE: 7
atggctctct tcttgctcac ctgcctgctg gctgtctttt cagcggccac ggcacaaagc      60
tccttattgg gtcccagctc catatttggt cccggggagg tgaatgtttt ggaaggcgac     120
tcggtgtcca tcacatgcta ctacccaaca acctccgtca cccggcacag ccggaagttc     180
tggtgccggg aagaggagag cggccgctgc gtgacgcttg cctcgaccgg ctacacgtcc     240
caggaatact ccgggagagg caagctcacc gacttccctg ataaagggga gtttgtggtg     300
actgttgacc aactcaccca gaacgactca gggagctaca agtgtggcgt gggagtcaac     360
ggccgtggcc tggacttcgg tgtcaacgtg ctggtcagcc agaagccaga g             411

<210> SEQ ID NO 8
<211> LENGTH: 137
<212> TYPE: PRT
<213> ORGANISM: Artificial Sequence
<220> FEATURE:
<223> OTHER INFORMATION: CHIMERA (R/HpIgR)

<400> SEQUENCE: 8

Met Ala Leu Phe Leu Leu Thr Cys Leu Leu Ala Val Phe Ser Ala Ala
1               5                   10                  15
Thr Ala Gln Ser Ser Leu Leu Gly Pro Ser Ser Ile Phe Gly Pro Gly
                20                  25                  30
Glu Val Asn Val Leu Glu Gly Asp Ser Val Ser Ile Thr Cys Tyr Tyr
                35                  40                  45
Pro Thr Thr Ser Val Thr Arg His Ser Arg Lys Phe Trp Cys Arg Glu
                50                  55                  60
```

Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
                100                 105                 110

Tyr Lys Cys Gly Val Gly Val Asn Gly Arg Gly Leu Asp Phe Gly Val
        115                 120                 125

Asn Val Leu Val Ser Gln Lys Pro Glu
    130                 135

<210> SEQ ID NO 9
<211> LENGTH: 1524
<212> TYPE: DNA
<213> ORGANISM: Artificial Sequence
<220> FEATURE:
<223> OTHER INFORMATION: CHIMERA (R/HpIgR)

<400> SEQUENCE: 9

| | | | | | |
|---|---|---|---|---|---|
| ctcctaaatg | acactaaagt | ctacacagtg | gacctgggca | gaacggtgac | catcaactgc | 60 |
| cctttcaaga | ctgagaatgc | tcaaaagagg | aagtccttgt | acaagcagat | aggcctgtac | 120 |
| cctgtgctgg | tcatcgactc | cagtggttat | gtaaatccca | actatacagg | aagaatacgc | 180 |
| cttgatattc | agggtactgg | ccagttactg | ttcagcgttg | tcatcaacca | actcaggctc | 240 |
| agcgatgctg | ggcagtatct | ctgccaggct | ggggatgatt | ccaatagtaa | taagaagaat | 300 |
| gctgacctcc | aagtgctaaa | gcccgagccc | gagctggttt | atgaagacct | gaggggctca | 360 |
| gtgaccttcc | actgtgccct | gggccctgag | gtggcaaacg | tggccaaatt | tctgtgccga | 420 |
| cagagcagtg | gggaaaactg | tgacgtggtc | gtcaacaccc | tggggaagag | ggccccagcc | 480 |
| tttgagggca | ggatcctgct | caaccccag | gacaaggatg | gctcattcag | tgtggtgatc | 540 |
| acaggcctga | ggaaggagga | tgcagggcgc | tacctgtgtg | gagcccattc | ggatggtcag | 600 |
| ctgcaggaag | gctcgcctat | ccaggcctgg | caactcttcg | tcaatgagga | gtccacgatt | 660 |
| ccccgcagcc | ccactgtggt | gaaggggtg | gcaggaggct | ctgtggccgt | gctctgcccc | 720 |
| tacaaccgta | aggaaagcaa | aagcatcaag | tactggtgtc | tctgggaagg | ggcccagaat | 780 |
| ggccgctgcc | ccctgctggt | ggacagcgag | gggtgggtta | aggcccagta | cgagggccgc | 840 |
| ctctccctgc | tggaggagcc | aggcaacggc | accttcactg | tcatcctcaa | ccagctcacc | 900 |
| agccgggacg | ccggcttcta | ctggtgtctg | accaacggcg | atactctctg | gaggaccacc | 960 |
| gtggagatca | agattatcga | aggagaacca | aacctcaagg | taccagggaa | tgtcacggct | 1020 |
| gtgctgggag | agactctcaa | ggtcccctgt | cactttccat | gcaaattctc | ctcgtacgag | 1080 |
| aaatactggt | gcaagtggaa | taacacgggc | tgccaggccc | tgcccagcca | agacgaaggc | 1140 |
| cccagcaagg | ccttcgtgaa | ctgtgacgag | aacagccggc | ttgtctccct | gaccctgaac | 1200 |
| ctggtgacca | gggctgatga | gggctggtac | tggtgtggag | tgaagcaggg | ccacttctat | 1260 |
| ggagagactg | cagccgtcta | tgtggcagtt | gaagagagga | aggcagcggg | gtcccgcgat | 1320 |
| gtcagcctag | cgaaggcaga | cgctgctcct | gatgagaagg | tgctagactc | tggttttcgg | 1380 |
| gagattgaga | caaagccat | tcaggatccc | aggcttttg | cagaggaaaa | ggcggtggca | 1440 |
| gatacaagag | atcaagccga | tgggagcaga | gcatctgtgg | attccggcag | ctctgaggaa | 1500 |
| caaggtggaa | gctccagaag | gtga | | | | 1524 |

<210> SEQ ID NO 10
<211> LENGTH: 507
<212> TYPE: PRT
<213> ORGANISM: Artificial Sequence
<220> FEATURE:
<223> OTHER INFORMATION: CHIMERA (R/HpIgR)

<400> SEQUENCE: 10

Leu Leu Asn Asp Thr Lys Val Tyr Thr Val Asp Leu Gly Arg Thr Val
1               5                   10                  15

Thr Ile Asn Cys Pro Phe Lys Thr Glu Asn Ala Gln Lys Arg Lys Ser
            20                  25                  30

Leu Tyr Lys Gln Ile Gly Leu Tyr Pro Val Leu Val Ile Asp Ser Ser
        35                  40                  45

Gly Tyr Val Asn Pro Asn Tyr Thr Gly Arg Ile Arg Leu Asp Ile Gln
    50                  55                  60

Gly Thr Gly Gln Leu Leu Phe Ser Val Val Ile Asn Gln Leu Arg Leu
65                  70                  75                  80

Ser Asp Ala Gly Gln Tyr Leu Cys Gln Ala Gly Asp Asp Ser Asn Ser
                85                  90                  95

Asn Lys Lys Asn Ala Asp Leu Gln Val Leu Lys Pro Glu Pro Glu Leu
            100                 105                 110

Val Tyr Glu Asp Leu Arg Gly Ser Val Thr Phe His Cys Ala Leu Gly
        115                 120                 125

Pro Glu Val Ala Asn Val Ala Lys Phe Leu Cys Arg Gln Ser Ser Gly
    130                 135                 140

Glu Asn Cys Asp Val Val Val Asn Thr Leu Gly Lys Arg Ala Pro Ala
145                 150                 155                 160

Phe Glu Gly Arg Ile Leu Leu Asn Pro Gln Asp Lys Asp Gly Ser Phe
                165                 170                 175

Ser Val Val Ile Thr Gly Leu Arg Lys Glu Asp Ala Gly Arg Tyr Leu
            180                 185                 190

Cys Gly Ala His Ser Asp Gly Gln Leu Gln Glu Gly Ser Pro Ile Gln
        195                 200                 205

Ala Trp Gln Leu Phe Val Asn Glu Glu Ser Thr Ile Pro Arg Ser Pro
    210                 215                 220

Thr Val Val Lys Gly Val Ala Gly Gly Ser Val Ala Val Leu Cys Pro
225                 230                 235                 240

Tyr Asn Arg Lys Glu Ser Lys Ser Ile Lys Tyr Trp Cys Leu Trp Glu
                245                 250                 255

Gly Ala Gln Asn Gly Arg Cys Pro Leu Leu Val Asp Ser Glu Gly Trp
            260                 265                 270

Val Lys Ala Gln Tyr Glu Gly Arg Leu Ser Leu Leu Glu Glu Pro Gly
        275                 280                 285

Asn Gly Thr Phe Thr Val Ile Leu Asn Gln Leu Thr Ser Arg Asp Ala
    290                 295                 300

Gly Phe Tyr Trp Cys Leu Thr Asn Gly Asp Thr Leu Trp Arg Thr Thr
305                 310                 315                 320

Val Glu Ile Lys Ile Ile Glu Gly Glu Pro Asn Leu Lys Val Pro Gly
                325                 330                 335

Asn Val Thr Ala Val Leu Gly Glu Thr Leu Lys Val Pro Cys His Phe
            340                 345                 350

Pro Cys Lys Phe Ser Ser Tyr Glu Lys Tyr Trp Cys Lys Trp Asn Asn
        355                 360                 365

Thr Gly Cys Gln Ala Leu Pro Ser Gln Asp Glu Gly Pro Ser Lys Ala

```
                     370                 375                 380
Phe Val Asn Cys Asp Glu Asn Ser Arg Leu Val Ser Leu Thr Leu Asn
385                 390                 395                 400

Leu Val Thr Arg Ala Asp Glu Gly Trp Tyr Trp Cys Gly Val Lys Gln
                405                 410                 415

Gly His Phe Tyr Gly Glu Thr Ala Ala Val Tyr Val Ala Val Glu Glu
                420                 425                 430

Arg Lys Ala Ala Gly Ser Arg Asp Val Ser Leu Ala Lys Ala Asp Ala
                435                 440                 445

Ala Pro Asp Glu Lys Val Leu Asp Ser Gly Phe Arg Glu Ile Glu Asn
                450                 455                 460

Lys Ala Ile Gln Asp Pro Arg Leu Phe Ala Glu Lys Ala Val Ala
465                 470                 475                 480

Asp Thr Arg Asp Gln Ala Asp Gly Ser Arg Ala Ser Val Asp Ser Gly
                485                 490                 495

Ser Ser Glu Glu Gln Gly Gly Ser Ser Arg Arg
                500                 505
```

<210> SEQ ID NO 11
<211> LENGTH: 2031
<212> TYPE: DNA
<213> ORGANISM: Artificial Sequence
<220> FEATURE:
<223> OTHER INFORMATION: HUMAN pIgR-CD4 cyto (HpIgR-cyto)

<400> SEQUENCE: 11

| | | | | | |
|---|---|---|---|---|---|
| atgctgctct | tcgtgctcac | ctgcctgctg | gcggtcttcc | cagccatctc | cacgaagagt | 60 |
| cccatatttg | gtcccgagga | ggtgaatagt | gtggaaggta | actcagtgtc | catcacgtgc | 120 |
| tactacccca | ccacctctgt | caaccggcac | acccggaagt | actggtgccg | gcagggagct | 180 |
| agaggtggct | gcataaccct | catctcctcg | gagggctacg | tctccagcaa | atatgcaggc | 240 |
| agggctaacc | tcaccaactt | cccggagaac | ggcacatttg | tggtgaacat | tgcccagctg | 300 |
| agccaggatg | actccgggcg | ctacaagtgt | ggcctgggca | tcaatagccg | aggcctgtcc | 360 |
| tttgatgtca | gcctggaggt | cagccagggt | cctgggctcc | taaatgacac | taaagtctac | 420 |
| acagtggacc | tgggcagaac | ggtgaccatc | aactgcccct | tcaagactga | aatgctcaa | 480 |
| aagaggaagt | ccttgtacaa | gcagataggc | ctgtaccctg | tgctggtcat | cgactccagt | 540 |
| ggttatgtaa | atcccaacta | tacaggaaga | atacgccttg | atattcaggg | tactggccag | 600 |
| ttactgttca | gcgttgtcat | caaccactc | aggctcagcg | atgctgggca | gtatctctgc | 660 |
| caggctgggg | atgattccaa | tagtaataag | aagaatgctg | acctccaagt | gctaaagccc | 720 |
| gagcccgagc | tggtttatga | agacctgagg | ggctcagtga | ccttccactg | tgccctgggc | 780 |
| cctgaggtgg | caaacgtggc | caaatttctg | tgccgacaga | gcagtgggga | aaactgtgac | 840 |
| gtggtcgtca | acaccctggg | gaagagggcc | ccagcctttg | agggcaggat | cctgctcaac | 900 |
| cccccaggaca | aggatggctc | attcagtgtg | gtgatcacag | gcctgaggaa | ggaggatgca | 960 |
| gggcgctacc | tgtgtggagc | ccattcggat | ggtcagctgc | aggaaggctc | gcctatccag | 1020 |
| gcctggcaac | tcttcgtcaa | tgaggagtcc | acgattcccc | gcagccccac | tgtggtgaag | 1080 |
| ggggtggcag | gaggctctgt | ggccgtgctc | tgcccctaca | accgtaagga | agcaaaagc | 1140 |
| atcaagtact | ggtgtctctg | gaagggggcc | cagaatggcc | gctgccccct | gctggtggac | 1200 |
| agcgagggggt | gggttaaggc | ccagtacgag | ggccgcctct | ccctgctgga | ggagccaggc | 1260 |
| aacggcacct | tcactgtcat | cctcaaccag | ctcaccagcc | gggacgccgg | cttctactgg | 1320 |

```
tgtctgacca acggcgatac tctctggagg accaccgtgg agatcaagat tatcgaagga   1380
gaaccaaacc tcaaggtacc agggaatgtc acggctgtgc tgggagagac tctcaaggtc   1440
ccctgtcact ttccatgcaa attctcctcg tacgagaaat actggtgcaa gtggaataac   1500
acgggctgcc aggccctgcc cagccaagac gaaggcccca gcaaggcctt cgtgaactgt   1560
gacgagaaca gccggcttgt ctccctgacc ctgaacctgg tgaccagggc tgatgagggc   1620
tggtactggt gtggagtgaa gcagggccac ttctatggag agactgcagc cgtctatgtg   1680
gcagttgaag agaggaaggc agcggggtcc cgcgatgtca gcctagcgaa ggcagacgct   1740
gctcctgatg agaaggtgct agactctggt tttcgggaga ttgagaacaa agccattcag   1800
gatcccaggc tttttgcaga ggaaaaggcg gtggcagata caagagatca gccgatggg   1860 agcagagcat ctgtggattc cggcagctct gaggaacaag gtggaagctc agaaggtgc   1920 cggcaccgaa ggcgccaagc agagcggatg tctcagatca agagactcct cagtgagaag   1980
aagacctgcc agtgccctca ccggtttcag aagacatgta gccccatttg a          2031
```

<210> SEQ ID NO 12
<211> LENGTH: 676
<212> TYPE: PRT
<213> ORGANISM: Artificial Sequence
<220> FEATURE:
<223> OTHER INFORMATION: HUMAN pIgR-CD4 cyto (HpIgR-cyto)

<400> SEQUENCE: 12

```
Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240
```

```
Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
                340                 345                 350

Pro Arg Ser Pro Thr Val Val Lys Gly Val Ala Gly Ser Val Ala
            355                 360                 365

Val Leu Cys Pro Tyr Asn Arg Lys Glu Ser Lys Ser Ile Lys Tyr Trp
        370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620

Val Asp Ser Gly Ser Ser Glu Glu Gln Gly Gly Ser Ser Arg Arg Cys
625                 630                 635                 640

Arg His Arg Arg Arg Gln Ala Glu Arg Met Ser Gln Ile Lys Arg Leu
                645                 650                 655
```

```
Leu Ser Glu Lys Lys Thr Cys Gln Cys Pro His Arg Phe Gln Lys Thr
            660                 665                 670

Cys Ser Pro Ile
        675

<210> SEQ ID NO 13
<211> LENGTH: 2058
<212> TYPE: DNA
<213> ORGANISM: Artificial Sequence
<220> FEATURE:
<223> OTHER INFORMATION: RABBIT pIgR-CD4 cyto (RpIgR-cyto)

<400> SEQUENCE: 13
atggctctct tcttgctcac ctgcctgctg gctgtctttt cagcggccac ggcacaaagc      60
tccttattgg gtcccagctc catatttggt cccggggagg tgaatgtttt ggaaggcgac     120
tcggtgtcca tcacatgcta ctacccaaca acctccgtca cccggcacag ccggaagttc     180
tggtgccggg aagaggagag cggccgctgc gtgacgcttg cctcgaccgg ctacacgtcc     240
caggaatact ccgggagagg caagctcacc gacttccctg ataaagggga gtttgtggtg     300
actgttgacc aactcaccca gaacgactca gggagctaca gtgtggcgt gggagtcaac      360 ggccgtggcc tggacttcgg tgtcaacgtg ctggtcagcc agaagccaga gcctgatgac     420
gttgtttaca acaatatga gagttataca gtaaccatca cctgcccttt cacatatgcg     480
actaggcaac taaagaagtc cttttacaag gtggaagacg ggaacttgt actcatcatt      540 gattccagca gtaaggaggc aaaggacccc aggtataagg cagaataac gttgcagatc      600 caaagtacca cagcaaaaga attcacagtc accatcaagc atttgcagct caatgatgct     660
gggcagtatg tctgccagag tggaagcgac cccactgctg aagaacagaa cgttgacctc     720
cgactgctaa ctcctggtct gctctatgga aacctggggg gctcggtgac ctttgaatgt     780
gccctggact ctgaagacgc aaacgcggta gcatccttgc gccaggttag gggtggcaat     840
gtggtcattg acagccaggg gacaatagat ccagccttcg agggcaggat cctgttcacc     900
aaggctgaga acggccactt cagtgtagtg atcgcaggcc tgaggaagga agacacaggg     960
aactatctgt gcggagtcca gtccaatggt cagtctgggg atgggcccac ccagcttcgg    1020
caactcttcg tcaatgaaga gatcgacgtg tcccgcagcc cctgtgtt gaagggcttt      1080 ccaggaggct ccgtgaccat cgctgcccc tacaacccga gagaagcga cagccacctg      1140 cagctgtatc tctgggaagg gagtcaaacc cgccatctgc tggtggacag cggcgagggg    1200
ctggttcaga aagactacac aggcaggctg gccctgttcg aagagcctgg caatggcacc    1260
ttctcagtcg tcctcaacca gctcactgcc gaggatgaag gcttctactg gtgtgtcagc    1320
gatgacgatg agtccctgac gacttcggtg aagctccaga tcgttgacgg agaaccaagc    1380
cccacgatcg acaagttcac tgctgtgcag ggagagcctg ttgagatcac ctgccacttc    1440
ccatgcaaat acttctcctc cgagaagtac tggtgcaagt ggaatgacca tggctgcgag    1500
gacctgccca ctaagctcag ctccagcggc gaccttgtga atgcaacaa caacctggtc     1560 ctcacccctg ccttggactc ggtcagcgaa gatgacgagg gctggtactg gtgtggcgcg    1620
aaagacgggc acgagtttga agaggttgcg gccgtcaggg tggagctgac agagccagcc    1680
aaggtagctg tcgagccagc caaggtacct gtcgacccag ccaaggcagc cccgcgcct    1740 gctgaggaga aggccaaggc gcggtgccca gtgcccagga aaggcagtg gtacccattg     1800 tcaaggaagc tgagaacaag ttgtccagaa cctcggctcc ttgcgaggag ggtagcagtg    1860
cagagtgcgg aagacccagc cagtgggagc agagcgtctg tggatgccag cagtgcttcg    1920
```

```
ggacaaagcg ggagtgccaa aaggtgccgg caccgaaggc gccaagcaga gcggatgtct   1980
cagatcaaga gactcctcag tgagaagaag acctgccagt gccctcaccg gtttcagaag   2040
acatgtagcc ccatttga                                                 2058
```

<210> SEQ ID NO 14
<211> LENGTH: 685
<212> TYPE: PRT
<213> ORGANISM: Artificial Sequence
<220> FEATURE:
<223> OTHER INFORMATION: RABBIT pIgR-CD4 cyto (RpIgR-cyto)

<400> SEQUENCE: 14

```
Met Ala Leu Phe Leu Leu Thr Cys Leu Leu Ala Val Phe Ser Ala
1               5                   10                  15

Thr Ala Gln Ser Ser Leu Leu Gly Pro Ser Ser Ile Phe Gly Pro Gly
                20                  25                  30

Glu Val Asn Val Leu Glu Gly Asp Ser Val Ser Ile Thr Cys Tyr Tyr
                35                  40                  45

Pro Thr Thr Ser Val Thr Arg His Ser Arg Lys Phe Trp Cys Arg Glu
    50                  55                  60

Glu Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
                100                 105                 110

Tyr Lys Cys Gly Val Gly Val Asn Gly Arg Gly Leu Asp Phe Gly Val
                115                 120                 125

Asn Val Leu Val Ser Gln Lys Pro Glu Pro Asp Val Val Tyr Lys
        130                 135                 140

Gln Tyr Glu Ser Tyr Thr Val Thr Ile Thr Cys Pro Phe Thr Tyr Ala
145                 150                 155                 160

Thr Arg Gln Leu Lys Lys Ser Phe Tyr Lys Val Glu Asp Gly Glu Leu
                165                 170                 175

Val Leu Ile Ile Asp Ser Ser Lys Glu Ala Lys Asp Pro Arg Tyr
        180                 185                 190

Lys Gly Arg Ile Thr Leu Gln Ile Gln Ser Thr Thr Ala Lys Glu Phe
        195                 200                 205

Thr Val Thr Ile Lys His Leu Gln Leu Asn Asp Ala Gly Gln Tyr Val
    210                 215                 220

Cys Gln Ser Gly Ser Asp Pro Thr Ala Glu Glu Gln Asn Val Asp Leu
225                 230                 235                 240

Arg Leu Leu Thr Pro Gly Leu Leu Tyr Gly Asn Leu Gly Gly Ser Val
                245                 250                 255

Thr Phe Glu Cys Ala Leu Asp Ser Glu Asp Ala Asn Ala Val Ala Ser
                260                 265                 270

Leu Arg Gln Val Arg Gly Gly Asn Val Val Ile Asp Ser Gln Gly Thr
        275                 280                 285

Ile Asp Pro Ala Phe Glu Gly Arg Ile Leu Phe Thr Lys Ala Glu Asn
    290                 295                 300

Gly His Phe Ser Val Val Ile Ala Gly Leu Arg Lys Glu Asp Thr Gly
305                 310                 315                 320

Asn Tyr Leu Cys Gly Val Gln Ser Asn Gly Gln Ser Gly Asp Gly Pro
                325                 330                 335
```

Thr Gln Leu Arg Gln Leu Phe Val Asn Glu Glu Ile Asp Val Ser Arg
            340                 345                 350

Ser Pro Pro Val Leu Lys Gly Phe Pro Gly Gly Ser Val Thr Ile Arg
            355                 360                 365

Cys Pro Tyr Asn Pro Lys Arg Ser Asp Ser His Leu Gln Leu Tyr Leu
            370                 375                 380

Trp Glu Gly Ser Gln Thr Arg His Leu Leu Val Asp Ser Gly Glu Gly
385                 390                 395                 400

Leu Val Gln Lys Asp Tyr Thr Gly Arg Leu Ala Leu Phe Glu Glu Pro
            405                 410                 415

Gly Asn Gly Thr Phe Ser Val Val Leu Asn Gln Leu Thr Ala Glu Asp
            420                 425                 430

Glu Gly Phe Tyr Trp Cys Val Ser Asp Asp Glu Ser Leu Thr Thr
            435                 440                 445

Ser Val Lys Leu Gln Ile Val Asp Gly Glu Pro Ser Pro Thr Ile Asp
            450                 455                 460

Lys Phe Thr Ala Val Gln Gly Glu Pro Val Glu Ile Thr Cys His Phe
465                 470                 475                 480

Pro Cys Lys Tyr Phe Ser Ser Glu Lys Tyr Trp Cys Lys Trp Asn Asp
            485                 490                 495

His Gly Cys Glu Asp Leu Pro Thr Lys Leu Ser Ser Gly Asp Leu
            500                 505                 510

Val Lys Cys Asn Asn Asn Leu Val Leu Thr Leu Thr Leu Asp Ser Val
            515                 520                 525

Ser Glu Asp Asp Glu Gly Trp Tyr Trp Cys Gly Ala Lys Asp Gly His
            530                 535                 540

Glu Phe Glu Glu Val Ala Ala Val Arg Val Glu Leu Thr Glu Pro Ala
545                 550                 555                 560

Lys Val Ala Val Glu Pro Ala Lys Val Pro Val Asp Pro Ala Lys Ala
            565                 570                 575

Ala Pro Ala Pro Ala Glu Glu Lys Ala Lys Ala Arg Cys Pro Val Pro
            580                 585                 590

Arg Arg Arg Gln Trp Tyr Pro Leu Ser Arg Lys Leu Arg Thr Ser Cys
            595                 600                 605

Pro Glu Pro Arg Leu Leu Ala Glu Glu Val Ala Val Gln Ser Ala Glu
            610                 615                 620

Asp Pro Ala Ser Gly Ser Arg Ala Ser Val Asp Ala Ser Ser Ala Ser
625                 630                 635                 640

Gly Gln Ser Gly Ser Ala Lys Arg Cys Arg His Arg Arg Gln Ala
            645                 650                 655

Glu Arg Met Ser Gln Ile Lys Arg Leu Leu Ser Glu Lys Lys Thr Cys
            660                 665                 670

Gln Cys Pro His Arg Phe Gln Lys Thr Cys Ser Pro Ile
            675                 680                 685

<210> SEQ ID NO 15
<211> LENGTH: 2046
<212> TYPE: DNA
<213> ORGANISM: Artificial Sequence
<220> FEATURE:
<223> OTHER INFORMATION: CHIMERA-CD4 cyto (R/HpIgR-cyto)

<400> SEQUENCE: 15
atggctctct tcttgctcac ctgcctgctg gctgtctttt cagcggccac ggcacaaagc     60

```
tccttattgg gtcccagctc catatttggt cccggggagg tgaatgtttt ggaaggcgac    120
tcggtgtcca tcacatgcta ctacccaaca acctccgtca cccggcacag ccggaagttc    180
tggtgccggg aagaggagag cggccgctgc gtgacgcttg cctcgaccgg ctacacgtcc    240
caggaatact ccgggagagg caagctcacc gacttccctg ataaagggga gtttgtggtg    300
actgttgacc aactcaccca gaacgactca gggagctaca agtgtggcgt gggagtcaac    360
ggccgtggcc tggacttcgg tgtcaacgtg ctggtcagcc agaagccaga gctcctaaat    420
gacactaaag tctacacagt ggacctgggc agaacggtga ccatcaactg ccctttcaag    480
actgagaatg ctcaaaagag gaagtccttg tacaagcaga taggcctgta ccctgtgctg    540
gtcatcgact ccagtggtta tgtaaatccc aactatacag aagaatacg ccttgatatt    600 cagggtactg gccagttact gttcagcgtt gtcatcaacc aactcaggct cagcgatgct    660
gggcagtatc tctgccaggc tggggatgat tccaatagta ataagaagaa tgctgacctc    720
caagtgctaa gcccgagcc cgagctggtt tatgaagacc tgaggggctc agtgaccttc    780
cactgtgccc tgggccctga ggtggcaaac gtggccaaat ttctgtgccg acagagcagt    840
ggggaaaact gtgacgtggt cgtcaacacc ctggggaaga gggccccagc ctttgagggc    900
aggatcctgc tcaaccccca ggacaaggat ggctcattca gtgtggtgat cacaggcctg    960
aggaaggagg atgcagggcg ctacctgtgt ggagcccatt cggatggtca gctgcaggaa    1020
ggctcgccta tccaggcctg gcaactcttc gtcaatgagg agtccacgat tccccgcagc    1080
cccactgtgg tgaaggggt ggcaggaggc tctgtggccg tgctctgccc ctacaaccgt    1140
aaggaaagca aaagcatcaa gtactggtgt ctctgggaag gggcccagaa tggccgctgc    1200
cccctgctgg tggacagcga ggggtgggtt aaggcccagt acgagggccg cctctccctg    1260
ctggaggagc aggcaacgg caccttcact gtcatcctca accagctcac cagccgggac    1320
gccggcttct actggtgtct gaccaacggc gatactctct ggaggaccac cgtggagatc    1380
aagattatcg aaggagaacc aaacctcaag gtaccaggga atgtcacggc tgtgctggga    1440
gagactctca aggtccccctg tcactttcca tgcaaattct cctcgtacga gaaatactgg    1500
tgcaagtgga ataacacggg ctgccaggcc ctgcccagcc aagacgaagg ccccagcaag    1560
gccttcgtga actgtgacga gaacagccgg cttgtctccc tgaccctgaa cctggtgacc    1620
agggctgatg agggctggta ctggtgtgga gtgaagcagg gccacttcta tggagagact    1680
gcagccgtct atgtggcagt tgaagagagg aaggcagcgg ggtcccgcga tgtcagccta    1740
gcgaaggcag acgctgctcc tgatgagaag gtgctagact ctggttttcg ggagattgag    1800
aacaaagcca ttcaggatcc caggcttttt gcagaggaaa aggcggtggc agatacaaga    1860
gatcaagccg atgggagcag agcatctgtg gattccggca gctctgagga acaaggtgga    1920
agctccagaa ggtgccggca ccgaaggcgc caagcagagc ggatgtctca gatcaagaga    1980
ctcctcagtg agaagaagac ctgccagtgc cctcaccggt ttcagaagac atgtagcccc    2040
atttga                                                              2046
```

<210> SEQ ID NO 16
<211> LENGTH: 681
<212> TYPE: PRT
<213> ORGANISM: Artificial Sequence
<220> FEATURE:
<223> OTHER INFORMATION: CHIMERA-CD4 cyto (R/HpIgR-cyto)

<400> SEQUENCE: 16

Met Ala Leu Phe Leu Leu Thr Cys Leu Leu Ala Val Phe Ser Ala Ala

```
 1               5                   10                  15
Thr Ala Gln Ser Ser Leu Leu Gly Pro Ser Ser Ile Phe Gly Pro Gly
             20                  25                  30
Glu Val Asn Val Leu Glu Gly Asp Ser Val Ser Ile Thr Cys Tyr Tyr
             35                  40                  45
Pro Thr Thr Ser Val Thr Arg His Ser Arg Lys Phe Trp Cys Arg Glu
 50                  55                  60
Glu Glu Ser Gly Arg Cys Val Thr Leu Ala Ser Thr Gly Tyr Thr Ser
 65                  70                  75                  80
Gln Glu Tyr Ser Gly Arg Gly Lys Leu Thr Asp Phe Pro Asp Lys Gly
             85                  90                  95
Glu Phe Val Val Thr Val Asp Gln Leu Thr Gln Asn Asp Ser Gly Ser
             100                 105                 110
Tyr Lys Cys Gly Val Gly Val Asn Gly Arg Gly Leu Asp Phe Gly Val
             115                 120                 125
Asn Val Leu Val Ser Gln Lys Pro Glu Leu Leu Asn Asp Thr Lys Val
 130                 135                 140
Tyr Thr Val Asp Leu Gly Arg Thr Val Thr Ile Asn Cys Pro Phe Lys
 145                 150                 155                 160
Thr Glu Asn Ala Gln Lys Arg Lys Ser Leu Tyr Lys Gln Ile Gly Leu
             165                 170                 175
Tyr Pro Val Leu Val Ile Asp Ser Ser Gly Tyr Val Asn Pro Asn Tyr
             180                 185                 190
Thr Gly Arg Ile Arg Leu Asp Ile Gln Gly Thr Gly Gln Leu Leu Phe
             195                 200                 205
Ser Val Val Ile Asn Gln Leu Arg Leu Ser Asp Ala Gly Gln Tyr Leu
 210                 215                 220
Cys Gln Ala Gly Asp Asp Ser Asn Ser Asn Lys Lys Asn Ala Asp Leu
 225                 230                 235                 240
Gln Val Leu Lys Pro Glu Pro Glu Leu Val Tyr Glu Asp Leu Arg Gly
             245                 250                 255
Ser Val Thr Phe His Cys Ala Leu Gly Pro Glu Val Ala Asn Val Ala
             260                 265                 270
Lys Phe Leu Cys Arg Gln Ser Ser Gly Glu Asn Cys Asp Val Val Val
             275                 280                 285
Asn Thr Leu Gly Lys Arg Ala Pro Ala Phe Glu Gly Arg Ile Leu Leu
 290                 295                 300
Asn Pro Gln Asp Lys Asp Gly Ser Phe Ser Val Val Ile Thr Gly Leu
 305                 310                 315                 320
Arg Lys Glu Asp Ala Gly Arg Tyr Leu Cys Gly Ala His Ser Asp Gly
             325                 330                 335
Gln Leu Gln Glu Gly Ser Pro Ile Gln Ala Trp Gln Leu Phe Val Asn
             340                 345                 350
Glu Glu Ser Thr Ile Pro Arg Ser Pro Thr Val Val Lys Gly Val Ala
             355                 360                 365
Gly Gly Ser Val Ala Val Leu Cys Pro Tyr Asn Arg Lys Glu Ser Lys
             370                 375                 380
Ser Ile Lys Tyr Trp Cys Leu Trp Glu Gly Ala Gln Asn Gly Arg Cys
 385                 390                 395                 400
Pro Leu Leu Val Asp Ser Glu Gly Trp Val Lys Ala Gln Tyr Glu Gly
             405                 410                 415
Arg Leu Ser Leu Leu Glu Glu Pro Gly Asn Gly Thr Phe Thr Val Ile
             420                 425                 430
```

```
Leu Asn Gln Leu Thr Ser Arg Asp Ala Gly Phe Tyr Trp Cys Leu Thr
        435                 440                 445

Asn Gly Asp Thr Leu Trp Arg Thr Thr Val Glu Ile Lys Ile Ile Glu
    450                 455                 460

Gly Glu Pro Asn Leu Lys Val Pro Gly Asn Val Thr Ala Val Leu Gly
465                 470                 475                 480

Glu Thr Leu Lys Val Pro Cys His Phe Pro Cys Lys Phe Ser Ser Tyr
                485                 490                 495

Glu Lys Tyr Trp Cys Lys Trp Asn Asn Thr Gly Cys Gln Ala Leu Pro
            500                 505                 510

Ser Gln Asp Glu Gly Pro Ser Lys Ala Phe Val Asn Cys Asp Glu Asn
        515                 520                 525

Ser Arg Leu Val Ser Leu Thr Leu Asn Leu Val Thr Arg Ala Asp Glu
    530                 535                 540

Gly Trp Tyr Trp Cys Gly Val Lys Gln Gly His Phe Tyr Gly Glu Thr
545                 550                 555                 560

Ala Ala Val Tyr Val Ala Val Glu Glu Arg Lys Ala Ala Gly Ser Arg
                565                 570                 575

Asp Val Ser Leu Ala Lys Ala Asp Ala Ala Pro Asp Glu Lys Val Leu
            580                 585                 590

Asp Ser Gly Phe Arg Glu Ile Glu Asn Lys Ala Ile Gln Asp Pro Arg
        595                 600                 605

Leu Phe Ala Glu Glu Lys Ala Val Ala Asp Thr Arg Asp Gln Ala Asp
    610                 615                 620

Gly Ser Arg Ala Ser Val Asp Ser Gly Ser Ser Glu Glu Gln Gly Gly
625                 630                 635                 640

Ser Ser Arg Arg Cys Arg His Arg Arg Gln Ala Glu Arg Met Ser
                645                 650                 655

Gln Ile Lys Arg Leu Leu Ser Glu Lys Lys Thr Cys Gln Cys Pro His
            660                 665                 670

Arg Phe Gln Lys Thr Cys Ser Pro Ile
        675                 680

<210> SEQ ID NO 17
<211> LENGTH: 411
<212> TYPE: DNA
<213> ORGANISM: Artificial Sequence
<220> FEATURE:
<223> OTHER INFORMATION: CHIMERA-CD4 cyto (R/HpIgR-cyto)

<400> SEQUENCE: 17
atggctctct tcttgctcac ctgcctgctg ctgtcttttt cagcggccac ggcacaaagc      60
tccttattgg gtcccagctc catatttggt cccggggagg tgaatgtttt ggaaggcgac     120
tcggtgtcca tcacatgcta ctacccaaca acctccgtca cccggcacag ccggaagttc     180
tggtgccggg aagaggagag cggccgctgc gtgacgcttg cctcgaccgg ctacacgtcc     240
caggaatact ccgggagagg caagctcacc gacttccctg ataaagggga gtttgtggtg     300
actgttgacc aactcaccca gaacgactca gggagctaca gtgtggcgt gggagtcaac     360 ggccgtggcc tggacttcgg tgtcaacgtg ctggtcagcc agaagccaga g             411

<210> SEQ ID NO 18
<211> LENGTH: 137
<212> TYPE: PRT
<213> ORGANISM: Artificial Sequence
<220> FEATURE:
```

<223> OTHER INFORMATION: CHIMERA-CD4 cyto (R/HpIgR-cyto)

<400> SEQUENCE: 18

```
Met Ala Leu Phe Leu Leu Thr Cys Leu Leu Ala Val Phe Ser Ala Ala
1               5                   10                  15

Thr Ala Gln Ser Ser Leu Leu Gly Pro Ser Ser Ile Phe Gly Pro Gly
            20                  25                  30

Glu Val Asn Val Leu Glu Gly Asp Ser Val Ser Ile Thr Cys Tyr Tyr
        35                  40                  45

Pro Thr Thr Ser Val Thr Arg His Ser Arg Lys Phe Trp Cys Arg Glu
    50                  55                  60

Glu Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
            100                 105                 110

Tyr Lys Cys Gly Val Gly Val Asn Gly Arg Gly Leu Asp Phe Gly Val
        115                 120                 125

Asn Val Leu Val Ser Gln Lys Pro Glu
    130                 135
```

<210> SEQ ID NO 19
<211> LENGTH: 1635
<212> TYPE: DNA
<213> ORGANISM: Artificial Sequence
<220> FEATURE:
<223> OTHER INFORMATION: CHIMERA-CD4 cyto (R/HpIgR-cyto)

<400> SEQUENCE: 19

| | | | | | |
|---|---|---|---|---|---|
| ctcctaaatg | acactaaagt | ctacacagtg | gacctgggca | gaacggtgac | catcaactgc | 60 |
| cctttcaaga | ctgagaatgc | tcaaaagagg | aagtccttgt | acaagcagat | aggcctgtac | 120 |
| cctgtgctgg | tcatcgactc | cagtggttat | gtaaatccca | actatacagg | aagaatacgc | 180 |
| cttgatattc | agggtactgg | ccagttactg | ttcagcgttg | tcatcaacca | actcaggctc | 240 |
| agcgatgctg | gcagtatctc | tgccaggctg | ggggatgatt | ccaatagtaa | taagaagaat | 300 |
| gctgacctcc | aagtgctaaa | gcccgagccc | gagctggttt | atgaagacct | gaggggctca | 360 |
| gtgaccttcc | actgtgccct | gggccctgag | gtggcaaacg | tggccaaatt | tctgtgccga | 420 |
| cagagcagtg | gggaaaactg | tgacgtggtc | gtcaacaccc | tggggaagag | gccccagccc | 480 |
| tttgagggca | ggatcctgct | caaccccag | gacaaggatg | gctcattcag | tgtggtgatc | 540 |
| acaggcctga | ggaaggagga | tgcagggcgc | tacctgtgtg | gagcccattc | ggatggtcag | 600 |
| ctgcaggaag | gctcgcctat | ccaggcctgg | caactcttcg | tcaatgagga | gtccacgatt | 660 |
| ccccgcagcc | ccactgtggg | aaggggggtg | gcaggaggct | ctgtggccgt | gctctgcccc | 720 |
| tacaaccgta | aggaaagcaa | aagcatcaag | tactggtgtc | tctgggaagg | ggcccagaat | 780 |
| ggccgctgcc | ccctgctggt | ggacagcgag | gggtgggtta | aggcccagta | cgagggccgc | 840 |
| ctctcccctgc | tggaggagcc | aggcaacgga | accttcactg | tcatcctcaa | ccagctcacc | 900 |
| agccgggacg | ccggcttcta | ctggtgtctg | accaacggcg | atactctctg | gaggaccacc | 960 |
| gtggagatca | agattatcga | aggagaacca | aacctcaagg | taccagggaa | tgtcacggct | 1020 |
| gtgctgggag | agactctcaa | ggtccccctgt | cactttccat | gcaaattctc | ctcgtacgag | 1080 |
| aaatactggt | gcaagtggaa | taacacgggc | tgccaggccc | tgcccagcca | agacgaaggc | 1140 |

```
cccagcaagg ccttcgtgaa ctgtgacgag aacagccggc ttgtctccct gaccctgaac    1200
ctggtgacca gggctgatga gggctggtac tggtgtggag tgaagcaggg ccacttctat    1260
ggagagactg cagccgtcta tgtggcagtt gaagagagga aggcagcggg gtcccgcgat    1320
gtcagcctag cgaaggcaga cgctgctcct gatgagaagg tgctagactc tggttttcgg    1380
gagattgaga acaaagccat tcaggatccc aggcttttg cagaggaaaa ggcggtggca    1440
gatacaagag atcaagccga tgggagcaga gcatctgtgg attccggcag ctctgaggaa    1500
caaggtggaa gctccagaag gtgccggcac cgaaggcgcc aagcagagcg atgtctcag    1560 atcaagagac tcctcagtga agaagacc tgccagtgcc ctcaccggtt tcagaagaca    1620
tgtagcccca tttga    1635
```

<210> SEQ ID NO 20
<211> LENGTH: 544
<212> TYPE: PRT
<213> ORGANISM: Artificial Sequence
<220> FEATURE:
<223> OTHER INFORMATION: CHIMERA-CD4 cyto (R/HpIgR-cyto)

<400> SEQUENCE: 20

```
Leu Leu Asn Asp Thr Lys Val Tyr Thr Val Asp Leu Gly Arg Thr Val
1               5                   10                  15

Thr Ile Asn Cys Pro Phe Lys Thr Glu Asn Ala Gln Lys Arg Lys Ser
            20                  25                  30

Leu Tyr Lys Gln Ile Gly Leu Tyr Pro Val Leu Val Ile Asp Ser Ser
        35                  40                  45

Gly Tyr Val Asn Pro Asn Tyr Thr Gly Arg Ile Arg Leu Asp Ile Gln
    50                  55                  60

Gly Thr Gly Gln Leu Leu Phe Ser Val Val Ile Asn Gln Leu Arg Leu
65                  70                  75                  80

Ser Asp Ala Gly Gln Tyr Leu Cys Gln Ala Gly Asp Asp Ser Asn Ser
                85                  90                  95

Asn Lys Lys Asn Ala Asp Leu Gln Val Leu Lys Pro Glu Pro Glu Leu
            100                 105                 110

Val Tyr Glu Asp Leu Arg Gly Ser Val Thr Phe His Cys Ala Leu Gly
        115                 120                 125

Pro Glu Val Ala Asn Val Ala Lys Phe Leu Cys Arg Gln Ser Ser Gly
    130                 135                 140

Glu Asn Cys Asp Val Val Val Asn Thr Leu Gly Lys Arg Ala Pro Ala
145                 150                 155                 160

Phe Glu Gly Arg Ile Leu Leu Asn Pro Gln Asp Lys Asp Gly Ser Phe
                165                 170                 175

Ser Val Val Ile Thr Gly Leu Arg Lys Glu Asp Ala Gly Arg Tyr Leu
            180                 185                 190

Cys Gly Ala His Ser Asp Gly Gln Leu Gln Glu Gly Ser Pro Ile Gln
        195                 200                 205

Ala Trp Gln Leu Phe Val Asn Glu Glu Ser Thr Ile Pro Arg Ser Pro
    210                 215                 220

Thr Val Val Lys Gly Val Ala Gly Ser Val Ala Val Leu Cys Pro
225                 230                 235                 240

Tyr Asn Arg Lys Glu Ser Lys Ser Ile Lys Tyr Trp Cys Leu Trp Glu
                245                 250                 255

Gly Ala Gln Asn Gly Arg Cys Pro Leu Leu Val Asp Ser Glu Gly Trp
            260                 265                 270
```

-continued

```
Val Lys Ala Gln Tyr Glu Gly Arg Leu Ser Leu Leu Glu Glu Pro Gly
        275                 280                 285

Asn Gly Thr Phe Thr Val Ile Leu Asn Gln Leu Thr Ser Arg Asp Ala
    290                 295                 300

Gly Phe Tyr Trp Cys Leu Thr Asn Gly Asp Thr Leu Trp Arg Thr Thr
305                 310                 315                 320

Val Glu Ile Lys Ile Ile Glu Gly Glu Pro Asn Leu Lys Val Pro Gly
            325                 330                 335

Asn Val Thr Ala Val Leu Gly Glu Thr Leu Lys Val Pro Cys His Phe
            340                 345                 350

Pro Cys Lys Phe Ser Ser Tyr Glu Lys Tyr Trp Cys Lys Trp Asn Asn
        355                 360                 365

Thr Gly Cys Gln Ala Leu Pro Ser Gln Asp Glu Gly Pro Ser Lys Ala
    370                 375                 380

Phe Val Asn Cys Asp Glu Asn Ser Arg Leu Val Ser Leu Thr Leu Asn
385                 390                 395                 400

Leu Val Thr Arg Ala Asp Glu Gly Trp Tyr Trp Cys Gly Val Lys Gln
                405                 410                 415

Gly His Phe Tyr Gly Glu Thr Ala Ala Val Tyr Val Ala Val Glu Glu
            420                 425                 430

Arg Lys Ala Ala Gly Ser Arg Asp Val Ser Leu Ala Lys Ala Asp Ala
        435                 440                 445

Ala Pro Asp Glu Lys Val Leu Asp Ser Gly Phe Arg Glu Ile Glu Asn
    450                 455                 460

Lys Ala Ile Gln Asp Pro Arg Leu Phe Ala Glu Glu Lys Ala Val Ala
465                 470                 475                 480

Asp Thr Arg Asp Gln Ala Asp Gly Ser Arg Ala Ser Val Asp Ser Gly
                485                 490                 495

Ser Ser Glu Glu Gln Gly Gly Ser Ser Arg Arg Cys Arg His Arg Arg
            500                 505                 510

Arg Gln Ala Glu Arg Met Ser Gln Ile Lys Arg Leu Leu Ser Glu Lys
        515                 520                 525

Lys Thr Cys Gln Cys Pro His Arg Phe Gln Lys Thr Cys Ser Pro Ile
    530                 535                 540
```